US012780940B2

(12) United States Patent
Chung et al.

(10) Patent No.: US 12,780,940 B2
(45) Date of Patent: Nov. 3, 2026

(54) PROTEIN COMPRISING ANTIBODY FOR TARGETING ONCOGENIC PROTEIN OR SINGLE CHAIN FRAGMENT VARIABLE THEREOF AND CANCER CELL PENETRATING PEPTIDE, AND USE OF THE SAME

(71) Applicant: NIBEC CO., LTD., Chungcheongbuk-do (KR)

(72) Inventors: Chong-Pyoung Chung, Seoul (KR); Yoon Jeong Park, Seoul (KR); Jue-Yeon Lee, Gyeonggi-do (KR); Deog Il Kim, Gyeonggi-do (KR); Eui Kyun Jeong, Seoul (KR)

(73) Assignee: NIBEC CO., LTD, Chungcheongbuk-Do (KR)

( * ) Notice: Subject to any disclaimer, the term of this patent is extended or adjusted under 35 U.S.C. 154(b) by 798 days.

(21) Appl. No.: 18/006,387

(22) PCT Filed: Aug. 12, 2021

(86) PCT No.: PCT/KR2021/010749
§ 371 (c)(1),
(2) Date: Jan. 22, 2023

(87) PCT Pub. No.: WO2022/035262
PCT Pub. Date: Feb. 17, 2022

(65) Prior Publication Data

US 2023/0279143 A1 Sep. 7, 2023

(30) Foreign Application Priority Data

Aug. 13, 2020 (KR) ........................ 10-2020-0101760

(51) Int. Cl.

| | |
|---|---|
| ***A61P 35/00*** | (2006.01) |
| ***C07K 16/32*** | (2006.01) |
| ***C12N 15/70*** | (2006.01) |
| *A61K 38/00* | (2006.01) |

(52) U.S. Cl.
CPC .............. *C07K 16/32* (2013.01); *A61P 35/00* (2018.01); *C12N 15/70* (2013.01); *A61K 38/00* (2013.01); *C07K 2317/622* (2013.01); *C07K 2319/10* (2013.01); *C12N 2800/101* (2013.01)

(58) Field of Classification Search
CPC ................................ A61P 35/00; C12N 15/70
See application file for complete search history.

(56) References Cited

U.S. PATENT DOCUMENTS

| | | | | |
|---|---|---|---|---|
| 9,849,190 | B2 * | 12/2017 | Park | C12Y 301/13 |
| 2008/0207484 | A1 | 8/2008 | Loeb et al. | |
| 2010/0048676 | A1 | 2/2010 | Chang | |
| 2019/0144566 | A1 * | 5/2019 | Kim | C07K 16/30 424/450 |

FOREIGN PATENT DOCUMENTS

| | | | |
|---|---|---|---|
| JP | 2016164156 | A | 9/2016 |
| KR | 1020140039347 | A | 4/2014 |
| KR | 1020150034746 | A | 4/2015 |
| KR | 1020160064726 | A | 6/2016 |
| KR | 102067675 | B1 | 1/2020 |
| KR | 20200026121 | A | 3/2020 |
| WO | 2019126240 | A1 | 6/2019 |
| WO | 2020046001 | A1 | 3/2020 |

OTHER PUBLICATIONS

Lim et al. (PLoS One, 8(6): 1-11, 2013, IDS).*
Duan, Z., et al., "Cell-penetrating peptide conjugates to enhance the antitumor effect of paclitaxel on drug-resistant lung cancer", Drug Delivery, 2017, pp. 752-764, vol. 24, No. 1, Publisher: Taylor & Francis.
Notice of Allowance issued on Jul. 25, 2024 for Japanese Patent Application 2023-533207.
English Translation of Notice of Allowance issued on Jul. 25, 2024 for Japanese Patent Application 2023-533207.
Asrorov, A.M., et al., "Advances on Tumor-Targeting Delivery of Cytotoxic Proteins", ACS Pharmacol. Transl. Sci., 2019, DOI: 10.1021/acsptsci.9b00087, Publisher: ACS Publications.
Search Report issued on Sep. 13, 2024 for the European Patent Application 21856268.4.
Notice of Allowance issued on Oct. 28, 2024 for Korean Patent Application 10-2021-0106810.
English Translation of Notice of Allowance issued on Oct. 28, 2024 for Korean Patent Application 10-2021-0106810.
Shin, S-M, et al., "Direct targeting of oncogenic RAS mutants with a tumor-specific cytosol-penetrating antibody inhibits RAS mutant-driven tumor growth", Science Advances, 2020, vol. 6: eaay2174, 18 pages.
Bayoudh, L., et al., "Trastuzumab (herceptine) in medical therapy of breast cancer", La Tunsie Medicale, 2012, pp. 6-12, vol. 90, No. 01.
Boudadi, K., et al., "Resistance to Novel Antiandrogen Therapies in Metastatic Castration-Resistant Prostate Cancer", Clinical Medicine Insights Oncology, 2016, pp. 1-9; doi: 10.4137/CMO.S34534, vol. 10, No. S1.

(Continued)

*Primary Examiner* — Nelson B Moseley, II
*Assistant Examiner* — Dennis J Sullivan
(74) *Attorney, Agent, or Firm* — HULTQUIST, PLLC; Steven J. Hultquist

(57) ABSTRACT

The present invention relates to: an antibody targeting a mutation of KRAS, which is an intracellular tumor-inducing protein, or a fusion protein in which a cancer-cell-penetrating peptide is connected, by means of a gene expression method or a chemical bonding method, to a single strand variable fragment of the antibody; and a tumor treatment use thereof. The fusion protein thus produced has the benefit of maximizing the anti-tumor or anti-cancer effect of the antibody targeting an intracellular tumor-inducing protein or a tumor-inducing mutant protein, or the single strand variable fragment of the antibody, by effectively invading a tumor cell.

15 Claims, 14 Drawing Sheets

Specification includes a Sequence Listing.

(56) References Cited

OTHER PUBLICATIONS

Chen, CD., et al., "Molecular determinants of resistance to antiandrogen therapy", Nature Medicine, 2004, pp. 33-39, vol. 10, No. 1.
Cox, A.D., et al., "Drugging the undruggable RAS: Mission Possible? ", Nature Reviews Drug Discovery, 2014, doi:10.1038/nrd4389, Publisher: Macmillan Publishers Limited.
Jemal, A., et al., "Annual Report to the Nation on the Status of Cancer, 1975-2001, with a Special Feature Regarding Survival", Cancer, 2004, DOI 10.1002/cncr.20288, vol. 101, No. 1, Publisher: American Cancer Society.
Kober, L., et al., "Optimized Signal Peptides for the Development of High Expressing CHO Cell Lines", Biotechnology and Bioengineering, 2913, pp. 1164-1173, vol. 110, No. 4, Publisher: Wiley Periodicals, Inc.
Lim, K.J., et al., "A Cancer Specific Cell-Penetrating Peptide, BR2, for the Efficient Delivery of an scFv into Cancer Cells", PLOS ONE, 2013, pp. e66084; doi:10.1371/journal.pone.0066084, vol. 8, No. 6, Publisher: www.plosone.org.
Oflazoglu, E., et al., "Evolution of anti-CD20monoclonal antibody therapeutics in oncology", mABs, 2010, pp. 14-19; DOI:10.4161/mabs.2.1.10789, vol. 2, No. 1.
Pylayeva-Gupta, Y., et al., "RAS oncogenes: weaving a tumorigenic web", Nature Reviews/Cancer, 2011, pp. 761-774, vol. 11, No. 11, Publisher: Macmillan Publishers Limited.
Rini, B.I., et al., "Hormone-refractory Prostate Cancer", Current Treatment Options in Oncology, 2002, pp. 437-446, vol. 3.
Sella, A., et al., "Paclitaxel, Estramustine and Carboplatin Combination Chemotherapy after Initial Docetaxel-Based Chemotherapy in Castration-Resistant Prostate Cancer", Oncology, 2009, pp. 442-446, vol. 76, Publisher: Karger.
Yagoda, A., et al., "Cytotoxic-Chemotherapy for Advanced Hormone-Resistant Prostate Cancer", Cancer Supplement, 1993, pp. 1098-1109, vol. 71, No. 3.
Zhang, L., et al., "Interrogating Androgen Receptor Function in Recurrent Prostate Cancer", Cancer Research, 2003, pp. 4552-4560, vol. 63.
Zhang, J., et al., "Pro-oncogenic and anti-oncogenic pathways: opportunities and challenges of cancer therapy", Future Oncol., 2010, pp. 587-603, vol. 6, No. 4, Publisher: Future Medicine Ltd.
Office Action issued on Jan. 31, 2024 for the Japanese Patent Application No. 2023-533207.
English translation of Office Action issued on Jan. 31, 2024 for the Japanese Patent Application No. 2023-533207.
Van De Wijngaart, D. J., et al., "Inhibition of Androgen Receptor Functions by Gelsolin FxxFF Peptide Delivered by Transfection, Cell-Penetrating Peptides, and Lentiviral Infection", The Prostate, 2011, pp. 241-253, vol. 71, Publisher: Wiley-Liss, Inc.

* cited by examiner

1. KRAS scFv (SEQ ID NO: 1)
2. KRAS scFv-CGGGGG-H4K (SEQ ID NO: 68 )
3. KRAS scFv-CGGGGG-H4P (SEQ ID NO: 69 )
4. KRAS scFv-CGGGGG-LMWP (SEQ ID NO: 70)
5. KRAS scFv-CGGGGG-hBD3-3 (SEQ ID NO: 71)
6. KRAS scFv-CGGGGGSSGGGGG-H4K (SEQ ID NO: 72 )
7. KRAS scFv-CGGGGGSSGGGGG-H4P (SEQ ID NO: 73 )
8. KRAS scFv-CGGGGGSSGGGGG-LMPW (SEQ ID NO: 74 )
9. KRAS scFv-CGGGGGSSGGGGG-hBD3-3 (SEQ ID NO: 75 )

PROTEIN COMPRISING ANTIBODY FOR TARGETING ONCOGENIC PROTEIN OR SINGLE CHAIN FRAGMENT VARIABLE THEREOF AND CANCER CELL PENETRATING PEPTIDE, AND USE OF THE SAME

CROSS-REFERENCE TO RELATED APPLICATIONS

This is a U.S. national phase under the provisions of 35 U.S.C. § 371 of International Patent Application No. PCT/KR2021/010749 filed Aug. 12, 2021, and claims priority under 35 U.S.C. § 119 of Korean Patent Application No. 10-2020-0101760 filed Aug. 13, 2020. The disclosures of such patent applications are hereby incorporated herein by reference in their respective entireties, for all purposes.

REFERENCE TO SEQUENCE LISTING

This application includes an electronically submitted sequence listing in .txt format. The .txt file contains a sequence listing entitled "661_UpdatedSeqListing_ST25.txt" created on Apr. 15, 2026 and is 187,050 bytes in size. The sequence listing contained in this .txt file is part of the specification and is hereby incorporated by reference herein in its entirety.

TECHNICAL FIELD

The present invention relates to a fusion protein comprising an intracellular oncogenic protein-targeting antibody or a single-chain variable fragment thereof; and a cancer cell-penetrating peptide and the use thereof, and more particularly, to a fusion protein wherein a cancer cell-penetrating peptide is linked to an antibody or a single-chain variable fragment thereof, which targets a mutation in the intracellular oncogenic protein KRAS, by a gene expression or chemical conjugation method, and the use thereof for treating tumors.

BACKGROUND ART

Tumors are caused by genetic mutations in normal cells due to activation of oncogenic pathways or inhibition of tumor suppressive pathways (1). Among various oncogenic factors, the RAS mutant protein is the most widely known oncogenic factor, and appears in about 30% of all cancer patients. The RAS mutant protein binds to GTP and remains activated, causing proliferation and growth of tumor cells. RAS may be divided into three categories: HRAS, NRAS, and KRAS. KRAS mutations are mainly found in non-small-cell-lung carcinoma, colorectal carcinoma, and pancreatic carcinoma, HRAS mutations are found in bladder carcinoma, kidney carcinoma, and thyroid carcinoma, and NRAS mutations are mainly found in melanoma, hepatocellular carcinoma, and hematologic malignancies (2). KRAS gene mutations account for 86% of cancers caused by RAS mutations, and are known to be found in more than 98% of pancreatic cancer, more than 53% of rectal cancer, and more than 30% of lung adenocarcinoma (3).

KRAS mutations are known to be deeply involved in the mechanism of resistance to anti-EGFR therapeutics such as Gefitinib, Erlotinib, and Cetuximab, which target epithelial growth factor receptor (EGFR). Even when EGFR inhibitory anticancer drugs are used, they have no effect at all in a state in which KRAS, which is downstream of EGFR, remains activated due to a mutation therein. In fact, administration of an anti-EGFR monoclonal therapeutic antibody in colorectal cancer is possible after determining that the patient does not have a KRAS mutation.

Antibody drugs have been widely studied as a means of anticancer treatment. For example, Trastuzumab is a monoclonal antibody against Her2 protein and is used as a treatment for breast cancer (4), and Rituximab is a monoclonal antibody against CD20 and is used as a treatment for B cell malignant lymphoma (5). Antibodies have an excellent inhibitory effect on the target, but because they cannot pass through the cell membrane due to high molecular weight thereof, it is difficult to obtain the inhibitory effect of the antibody when the target of the antibody is inside the cell.

Prostate cancer is the third most common male cancer in the world, and in the United States, it is the most common male cancer and has the second highest cancer-specific mortality after lung cancer (7). Local prostate cancer can be cured by surgery or radiation therapy, but chemical castration is mainly used as a standard treatment for advanced or metastatic prostate cancer. After it was proved that prostate cancer is testosterone-dependent cancer, artificial castration was established as the primary treatment for advanced or metastatic prostate cancer, and castration treatment for various types of prostate cancer has been used in clinical practice (8). In metastatic prostate cancer, castration shows effects such as disease progression and alleviation of accompanying symptoms, but it is known that only 75% of patients consistently respond to treatment when castration is performed for more than 18 months. Castration shows a relatively good response at the beginning, but over time, prostate cancer cells do not undergo apoptosis due to androgen blockade and are converted into castration-resistant prostate cancer (CRPC) cells which are no longer responsive to hormone treatment (9).

CRPC is defined as a condition in which the testes produce no testosterone so that testosterone in blood is reduced, and even after administration of all drugs that act through androgen receptors is stopped, there is no decrease in prostate specific antigen (PSA), and a significant increase in PSA or radiological progression appears. If CRPC is left untreated, the average survival period is less than 12 months, and following various treatments, the average survival period of metastatic prostate cancer patients is less than 3 years, and in the case of locally invasive disease, the average survival period is only 4.5 years (10).

It is known that androgen receptor (AR) in CRPC is reactivated by various mechanisms such as AR overexpression, mutation, hypersensitivity, and androgen synthesis in the tumor (11).

Abiraterone, an FDA-approved CRPC treatment, is an inhibitor of androgen synthesis, and enzalutamide (MDV3100), a second-generation androgen receptor antagonist, completely inhibits androgen binding to androgen receptors, thus keeping androgen receptors from moving into the nucleus and binding to target genes. Since most prostate cancers that recur after abiraterone or enzalutamide treatment are PSA-positive and androgen receptor is reactivated, new androgen receptor inhibitory therapies are needed for CRPC patients resistant to abiraterone or enzalutamide (12). Androgen receptor, a member of the steroid receptor superfamily, is a ligand-dependent transcription factor that regulates the expression of genes affected by androgens. In order for a transcription factor to access the target gene, the transcription factor must enter the nucleus, and thus if the transcription factor can be maintained only in the cytoplasm, the transcription function can be blocked. Accordingly, the most important step is to control the translocation of androgen receptors into the nucleus. Androgen-sensitive receptors remain in the cytoplasm in the absence of androgens, and move into the nucleus in the presence of androgens and activate target genes. However, in CRPC cells, androgen receptors continue to activate the target genes because they remain in the nucleus even in the absence of androgens (13). Accordingly, if any substance can inhibit androgen receptor translocation into the nucleus, it can be used as an effective treatment for CRPC tumors.

Oncogenic proteins such as KRAS and androgen receptors are known to play an important role in the development of human cancer, but antibody therapeutics targeting these oncogenic proteins have not yet been used clinically. The reason is that the antibody against the RAS and androgen receptor distributed in the cell cannot pass through the cell membrane because of its high molecular weight. It is known that a single-chain variable fragment (scFv) smaller than an antibody has a smaller molecular weight than the antibody and does not have an Fc region that causes immune rejection, and thus it can be an alternative to a general antibody. However, since scFv itself has a molecular weight of 25 kDa or more, it is difficult for scFv to freely pass through the cell membrane, unlike low-molecular-weight drugs, and thus it is difficult to obtain a large inhibitory effect as expected.

Accordingly, the present inventors have made extensive efforts to solve the above-described problems occurring in the prior art, and as a result, have attempted to fuse an antibody against an intracellular oncogenic protein or a single-chain variable fragment thereof with a cancer cell penetrating functional peptide so as to be capable of penetrating cancer tissue. As the fusion method, a gene expression method or a chemical conjugation method was used, and the present inventors have found through in vitro and animal experiments that the cell-penetrating fusion protein produced by this method can effectively inhibit the proliferation and growth of cancer cells in which oncogenic proteins are highly expressed, thereby completing the present invention.

PRIOR ART

Non-Patent Literature (Non-Patent Document 1) Zhang J, Chen Y H, Lu Q. Pro-oncogenic and anti-oncogenic pathways: opportunities and challenges of cancer therapy. Future Oncol. 2010 April; 6(4):587-603.

(Non-Patent Document 2) Cox A D, Fesik S W, Kimmelman A C, Luo J, Der C J. Drugging the undruggable RAS: mission possible? Nat Rev Drug Discov 2014; 13: 828-51.

(Non-Patent Document 3) RAS oncogenes: weaving a tumorigenic web. Pylayeva-Gupta Y, Grabocka E, Bar-Sagi D. Nat Rev Cancer. 2011 Oct. 13; 11(11):761-74.

(Non-Patent Document 4) Trastuzumab (herceptin) for the medical treatment of breast cancer. Bayoudh L, Afrit M, Daldoul O, Zarrad M, Boussen H. Tunis Med. 2012 January; 90(1):6-12.

(Non-Patent Document 5) Evolution of anti-CD20 monoclonal antibody therapeutics in oncology. Oflazoglu E, Audoly L P. MAbs. 2010 January-February; 2(1):14-9.

(Non-Patent Document 6) Demarest S J, Glaser S M. Antibody therapeutics, antibody engineering, and the merits of protein stability. Curr Opin Drug Discov Devel. 2008; 11(5):675-687.

(Non-Patent Document 7) Jemal A, Clegg L X, Ward E, Ries L A, Wu X, Jamison P M, et al. Annual report to the nation on the status of cancer, 1975-2001, with a special feature regarding survival. Cancer 2004; 101:3-27.

(Non-Patent Document 8) Yagoda A, Petrylak D. Cytotoxic chemotherapy for advanced hormone-resistant prostate cancer. Cancer 1993; 71:1098.

(Non-Patent Document 9) Rini B I, Small E J. Hormone-refractory prostate cancer. Curr Treat Opt Oncol 2002; 3:437-46.

(Non-Patent Document 10) Sella A, Yarom N, Zisman A, Kovel S. Paclitaxel, estramustine and carboplatin combination chemotherapy after initial docetaxel-based chemotherapy in castration resistant prostate cancer. Oncology 2009; 76:442.

(Non-Patent Document 11) Chen C D, Welsbie D S, Tran C, Baek S H, Chen R, Vessella R, et al. Molecular determinants of resistance to antiandrogen therapy. Nat Med 2004; 10:33-9.

(Non-Patent Document 12) Boudadi K, Antonarakis E S. Resistance to novel antiandrogen therapies in metastatic castration-resistant prostate cancer. Clin Med Insights Oncol 2016; 10:1-9.

(Non-Patent Document 13) Zhang L, Johnson M, Le K H, Sato M, Ilagan R, Iyer M, et al. Interrogating androgen receptor function in recurrent prostate cancer. Cancer Res 2003; 63:4552-60.

(Non-Patent Document 14) Lars Kober, Christoph Zehe, Juergen Bode, Biotechnology and Bioengineering, Vol. 110, No. 4, April, 2013, Optimized signal peptides for the development of high expressing CHO cell lines.

SUMMARY OF THE INVENTION

An object of the present invention is to provide a fusion protein having a significantly improved tumor treatment effect.

Another object of the present invention is to provide a pharmaceutical composition for treating a tumor comprising the fusion protein as an active ingredient.

Still another object of the present invention is to provide a method for preventing or treating a tumor comprising a step of administering the fusion protein.

Yet another object of the present invention is to provide the use of the fusion protein for preventing or treating a tumor.

Still yet another object of the present invention is to provide the use of the fusion protein in the manufacture of a medicament for treating a tumor.

To achieve the above objects, the present invention provides a fusion protein in which (i) an antibody or a single-chain variable fragment thereof, which targets an intracellular oncogenic protein or oncogenic mutant protein, is linked with (ii) a cancer cell-penetrating peptide.

The present invention also provides a nucleic acid encoding the fusion protein.

The present invention also provides a recombinant vector into which the nucleic acid has been introduced.

The present invention also provides a recombinant cell into which the recombinant vector has been introduced.

The present invention also provides a method for producing the fusion protein comprising steps of:

(a) expressing the fusion protein by culturing the recombinant cell; and (b) recovering the expressed fusion protein.

The present invention also provides a pharmaceutical composition for treating a tumor comprising the fusion protein as an active ingredient.

The present invention also provides a method for preventing or treating a tumor comprising administering the fusion protein.

The present invention also provides the use of the fusion protein for preventing or treating a tumor.

The present invention also provides the use of the fusion protein in the manufacture of a medicament for treating a tumor.

DETAILED DESCRIPTION AND PREFERRED EMBODIMENTS OF THE INVENTION

Figure 1:
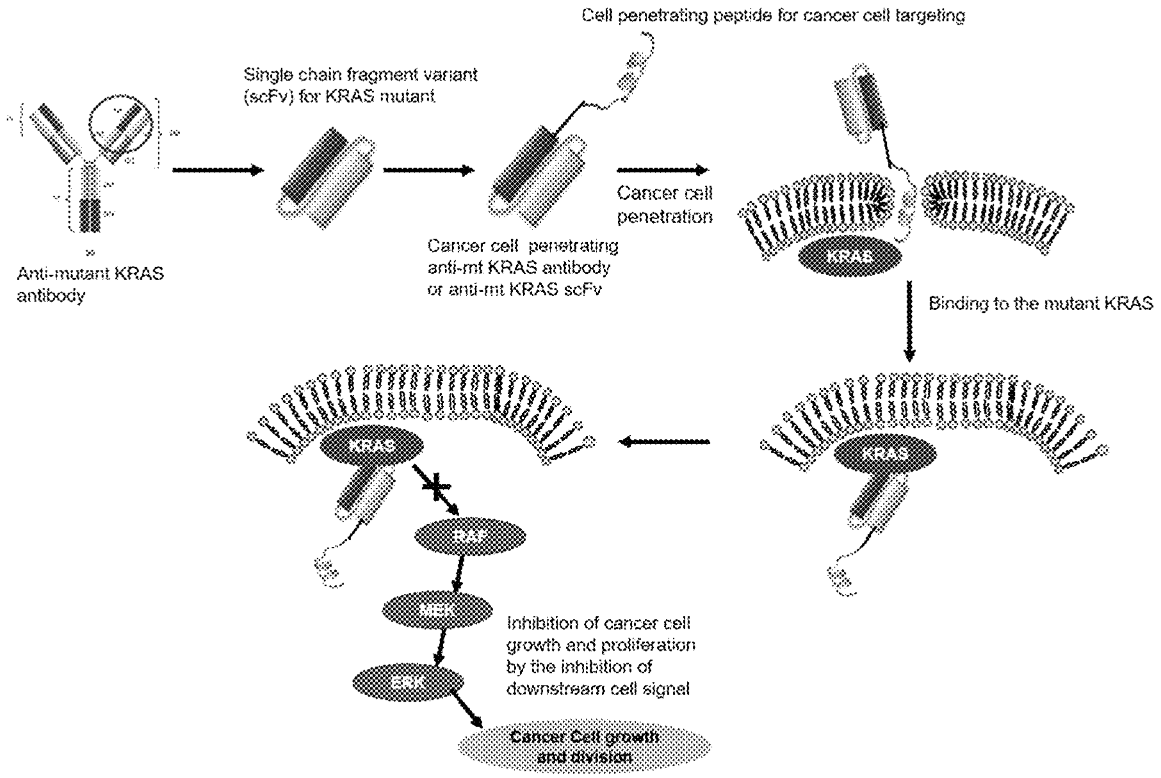
FIG. 1 is a schematic view showing the outline of the present invention.
Figure 2:
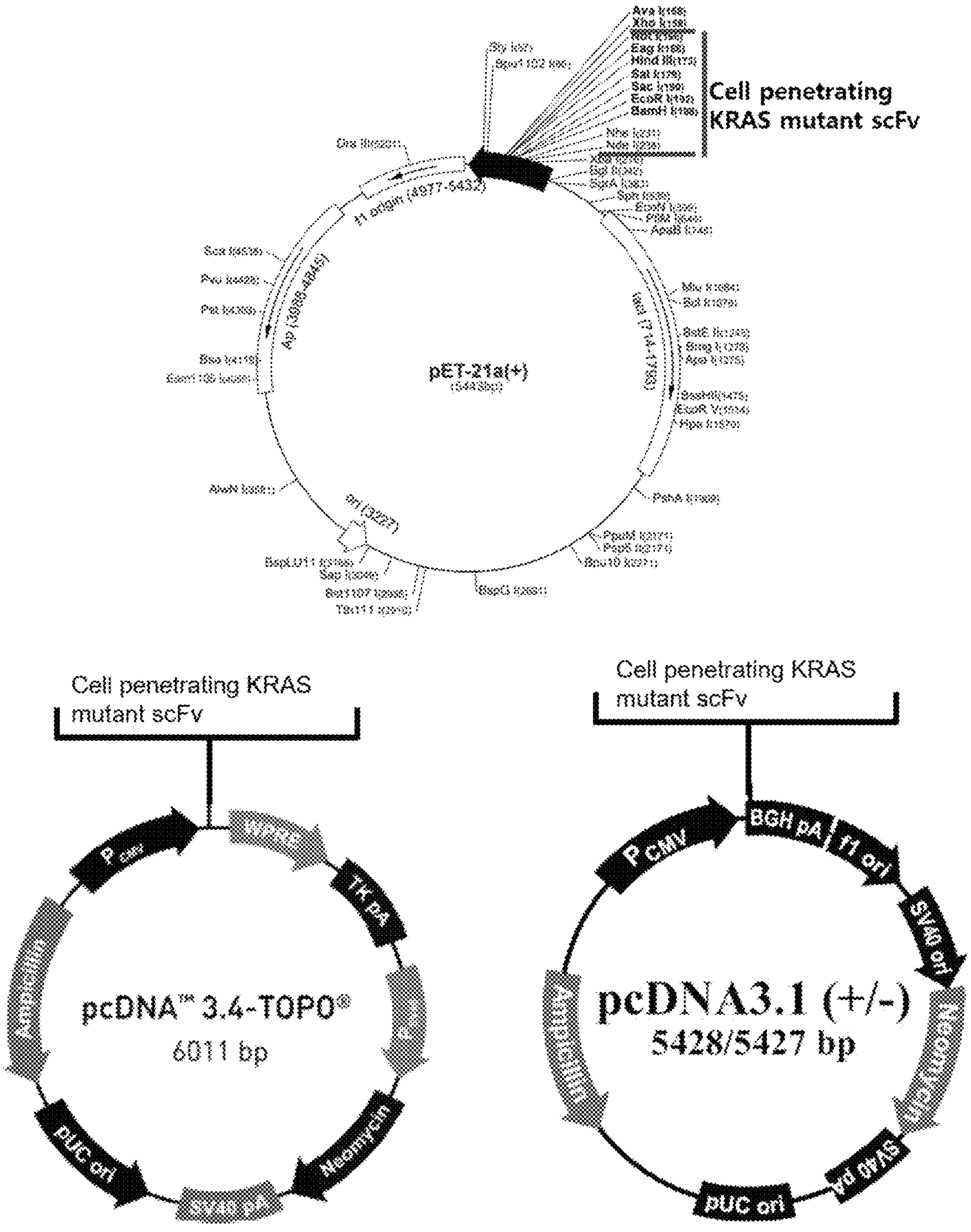
FIG. 2 shows expression vectors, each comprising a cancer cell-penetrating KRAS mutant antibody or scFv.

Unless otherwise defined, all technical and scientific terms used in the present specification have the same meanings as commonly understood by those skilled in the art to which the present invention pertains. In general, the nomenclature used in the present specification and the experimental methods described below are well known and commonly used in the art.

The present inventors paid attention to the fact that, even if an antibody or a single-chain variable fragment thereof, which targets an intracellular oncogenic protein or oncogenic mutant protein, reaches cancer cells, it cannot sufficiently act on the cancer cells. Accordingly, the present inventors have produced a fusion protein wherein the antibody or single-chain variable fragment thereof is linked with a cancer cell-penetrating peptide. To produce the fusion protein, a linker was introduced to the N-terminus or C-terminus of an antibody or a single-chain variable fragment thereof, which targets an intracellular oncogenic protein or oncogenic mutant protein, and a cancer cell-penetrating peptide was linked thereto. This fusion protein was produced by any one of two different methods: a gene expression method and a chemical conjugation method. In a cancer cell killing experiment conducted using the fusion protein produced as described above, it was confirmed that the fusion protein comprising the cancer cell-penetrating peptide exhibited a significantly better cancer cell-specific effect than the antibody or single-chain variable fragment thereof alone which targets the intracellular oncogenic protein or oncogenic mutant protein.

Therefore, in one aspect, the present invention is directed to a fusion protein in which (i) an antibody or a single-chain variable fragment thereof, which targets an intracellular oncogenic protein or oncogenic mutant protein, is linked with (ii) a cancer cell-penetrating peptide.

In the present invention, the intracellular oncogenic protein or oncogenic mutant protein may be KRAS or androgen receptor, but is not limited thereto.

In the present invention, the antibody or single-chain variable fragment thereof may be selected from the group consisting of SEQ ID NOs: 1 to 3, but is not limited thereto.

In one embodiment, the single-chain variable fragment may be a KRAS mutant scFv represented by SEQ ID NO: 1 below.

SEQ ID NO: 1

MAWVWTLLFLMAAAQSIQAEWIKQRPGQGLEWIGV

IHPGNGGTNYNENFKGKATLTADKSSSTAYMQLSS

LTSDDSAVYFCASGNDGSYWGQGTTVTVSSGGGGS

GKGGSGGGGSGGGGSDIELTQSPSSLTVTAGEKVT

MSCKSSQSLLNSGDQKIYLTWYQQKPGQPPKLLIY

WASTRESGVPDRFTGSVSGTDFTLTISSVQAEDLA

VYYCONDYNYPYTFGGGTKLEIKRGSENLYFQGGS

GKPIPNPLLGLDSTGGSGGSHHHHHH

Here, MAWVWTLLFLMAAAQSIQA is a signal peptide, the amino acid sequence following the signal peptide is a variable heavy chain (VH) region, GGGGSGKGGSGGGGSGGGGS (SEQ ID NO: 98) is a linker, and the amino acid sequence following the linker is a variable light chain (VL) region. The signal peptide may also be replaced with a known sequence such as MTRLTVLALLAGLLASSRA or MKWVTFISLLFLFSSAYS.

In another embodiment, the single-chain variable fragment may be a KRAS mutant scFv represented by SEQ ID NO: 2 below.

```
                                  SEQ ID NO: 2
MAQVKLQESGPELVRPGTSVKVSCKASGYAFTNYL

IEWIKQRPGQGLEWIGVIHPGNGGTNYNENFKGKA

TLTADKSSSTAYMQLSSLTSDDSAVYFCASGNDGS

YWGQGTTVTVSSGGGGSGGGGSGGGGSDIELTQSP

SSLTVTAGEKVTMSCKSSQSLLNSGDQKIYLTWYQ

QKPGQPPKLLIYWASTRESGVPDRFTGSVSGTDFT

LTISSVQAEDLAVYYCONDYNYPYTFGGGTKLEIK

RLEHHHHHH
```

MAQVKLQESGPELVRPGTSVKVSCKASGYAFTNYLI is a signal peptide, the amino acid sequence following the signal peptide is a variable heavy chain (VH) region, GGGGSGGGGSGGGGS (SEQ ID NO: 95) is a linker, and the amino acid sequence following the liker is a variable light chain (VL) region.

In another embodiment, the single-chain variable fragment may be a KRAS mutant scFv represented by SEQ ID NO: 3 below.

```
                                                SEQ ID NO: 3
MAWVWTLLFLMAAAQSIQAEWIKQRPGQGLEWIGVIHPGNGGTNYNENF

KGKATLTADKSSSTAYMQLSSLTSDDSAVYFCASGNDGSYWGQGTTVTV

SSGGGGSGKGGSGGGGSGGGGSDIELTQSPSSLTVTAGEKVTMSCKSSQ

SLLNSGDQKIYLTWYQQKPGQPPKLLIYWASTRESGVPDRFTGSVSGTD

FTLTISSVQAEDLAVYYCQNDYNYPYTFGGGTKCLEIKRGSENLYFQGG

SGKPIPNPLLGLDSTGGSGGSHHHHHH
```

SEQ ID NO: 3 is the same as SEQ ID NO: 1, except that cysteine is introduced after $V_L$.

In the present invention, the cancer cell-penetrating peptide may be selected from the group consisting of CCPP1 (H4K), CCPP2 (H4P), CCPP3 (LMWP) and CCPP4 (hBD3-3), but is not limited thereto. The cancer cell-penetrating peptide may be selected from the group consisting of SEQ ID NO: 86 to SEQ ID NO: 89, but is not limited thereto.

In the present invention, the cancer cell-penetrating may be linked to the N-terminus or C-terminus of the antibody or single-chain variable fragment thereof via a linker.

In the present invention, the linker serves to provide a space so that the cancer cell-penetrating peptide and the antibody or single-chain variable fragment thereof may individually form a functional structure when linked together. The linker is preferably a peptide linker comprising an appropriate combination of amino acids G and S. Here, more preferably, the number of amino acid residues G is from 3 to 20, and the number of amino acid residues S is from 1 to 5, but the present invention is not limited thereto. Most preferably, the linker is GGGGS (SEQ ID NO: 94) or GGGGSGGGGSGGGGS (SEQ ID NO: 95).

In the present invention, when the linker and the cancer cell-penetrating peptide are linked together, they may be represented by the amino acid sequence of any one of SEQ ID NO: 4 to SEQ ID NO: 11, without being limited thereto. In this case, the fusion peptide represented by any one of the amino acid sequences of SEQ ID NOs: 4 to 7 is preferably linked to the C terminus of the single-chain variable fragment, and the fusion peptide represented by the amino acid sequence of any one of SEQ ID NOs: 8 to 11 is preferably linked to the N-terminus of the single-chain variable fragment. In another embodiment, the fusion peptide represented by the amino acid sequence of any one of SEQ ID NOs: 4 to 11 may be further bound to a linker connecting the heavy chain to the light chain of the single-chain fragment of the antibody. Meanwhile, when the fusion peptide represented by any one of the amino acid sequences of SEQ ID NOs: 4 to 11 is linked to the antibody, it is preferably linked to a sugar structure present in the Fc region.

In the present invention, the antibody or single-chain variable fragment thereof and the cancer cell-penetrating peptide may be linked together by a chemical conjugation method. In this case, the fusion protein may be represented by the amino acid sequence of any one of SEQ ID NOs: 68 to 83, but is not limited thereto.

In the present invention, the fusion protein may be one wherein the cancer cell-penetrating peptides of any one selected from the group consisting of SEQ ID NOs: 86 to 89 is linked via a linker to the lysine or cysteine residue of the single-chain variable fragment of any one selected from the group consisting of SEQ ID NOs: 1 to 3.

In the present invention, the linker may be CGGGGG (SEQ ID NO: 96) or CGGGGGSSGGGGG (SEQ ID NO: 97).

In the present invention, the antibody or single-chain variable fragment thereof and the cancer cell-penetrating peptide may be linked together and expressed by a gene expression method. In this case, the fusion protein may be expressed in *Escherichia coli* and may be represented by the amino acid sequence of any one of SEQ ID NOs: 12 to 27, without being limited thereto. In addition, the fusion protein may be expressed in mammalian cells, and may be represented by the amino acid sequence of any one of SEQ ID NO: 28 to SEQ ID NO: 59, and SEQ ID NO: 90 to SEQ ID NO: 93, without being limited thereto.

For example, the cancer cell-penetrating peptide and the linker may be linked to the N-terminus of the single-chain variable fragment (any one of SEQ ID NO: 1 to SEQ ID NO: 3) which targets the KRAS mutant protein, or the cancer cell-penetrating peptide and the linker may be linked to the N-terminus of the single-chain variable fragment. Various embodiments related thereto are specifically described in Tables 2 to 5 in Examples below.

In the present invention, the fusion protein may be represented by any one of the amino acid sequences of SEQ ID NO: 12 to SEQ ID NO: 59, SEQ ID NO: 68 to SEQ ID NO: 83, and SEQ ID NO: 90 to SEQ ID NO: 93.

In the present invention, the fusion protein may be produced by a gene expression method or a chemical conjugation method, but the production method is not limited thereto.

When the fusion protein is produced by the gene expression method, it is possible to use a vector that expresses both (i) the antibody or single-chain variable fragment thereof that targets the intracellular oncogenic protein or oncogenic mutant protein, and (ii) the cancer cell-penetrating peptide.

In this case, the vector for expression may further contain a linker sequence between the antibody or single-chain variable fragment thereof and the cancer cell-penetrating peptide. A pET vector, pcDNA 3.4, pcDNA3.1, pcDNA3.1-TOPO, pcDNA3.4-TOPO, pSecTag vector, etc. may be used, but the vector is not limited thereto. In the present invention, a pET vector was used for expression in *E. coli*, and a pcDNA3.1-TOPO or pcDNA3.4-TOPO vector was used for expression in mammalian cells.

Therefore, in another aspect, the present invention is directed to a nucleic acid encoding the fusion protein.

The present invention is also directed to a recombinant vector into which the nucleic acid has been introduced.

The present invention is also directed to a recombinant cell into which the recombinant vector has been introduced.

In the present invention, the recombinant cell may be an *E. coli* or mammalian cell, but is not limited thereto.

Examples of preferred mammalian cell lines that may be used in the present invention include, but are not limited to, Chinese hamster ovarian (CHO) cells, human embryonic kidney cells (HEK293), and the like.

The present invention is also directed to a method for producing the fusion protein comprising steps of: (a) expressing the fusion protein by culturing the recombinant cell; and (b) recovering the expressed fusion protein.

Meanwhile, in the present invention, the antibody or single-chain variable fragment thereof that targets the intracellular oncogenic protein or oncogenic mutant protein may be expressed and purified, and then the cancer cell-penetrating peptide may be introduced thereto by a chemical conjugation method.

The cancer cell-penetrating peptide may be linked to the antibody or single-chain variable fragment thereof via a linker and a crosslinker. As the linker, any linker may be used as long as it may provide a space capable of forming a functional structure. For example, the linker may be a peptidic linker of natural and/or synthetic origin. The peptidic linker of natural and/or synthetic origin may consist of an amino acid chain consisting of 1 to 50 amino acids, and may comprise repetitive amino acid sequences or sequences of naturally occurring polypeptides, such as polypeptides with a hinge-function. In another embodiment, the peptidic linker amino acid sequence may be a "synthetic linker amino acid sequence" that is designated to be rich in glycine, glutamine, and/or serine residues. These residues may be arranged in small repetitive units of up to five amino acids, and the small repetitive unit may be repeated to form a multimeric unit. At the amino- and/or carboxy-terminal ends of the multimeric unit, up to six additional arbitrary, naturally occurring amino acids may be added. Other synthetic peptidic linkers may be composed of a single amino acid, which is repeated between 10 to 20 times, and may comprise, at the amino- and/or carboxy-terminal end, up to six additional arbitrary, naturally occurring amino acids. Meanwhile, the linker may be in a form in which amino acids are chemically modified. For example, the linker may be in the form of Fmoc-6-aminohexanoic acid to which Fmoc-(9-fluorenylmethoxycarbonyl) as a blocking group is bonded, but the linker is not limited thereto.

In some embodiments of the present invention, the fusion peptide in which the cancer cell-penetrating peptide and the linker are linked together may be represented by the amino acid sequence of any one of SEQ ID NOs: 60 to 67. In this case, the sulfhydryl group of cysteine located at the N-terminus of the cancer cell-penetrating peptide may be linked to the amine group of lysine in the linker moiety of SEQ ID NO: 1 or the amine group of lysine in the exposed portion in the three-dimensional structure.

In this case, examples of the crosslinker that may be used include, but are not limited to, 1,4-bis-maleimidobutane (BMB), 1,11-bis-maleimidotetraethyleneglycol (BM[PEO]4), 1-ethyl-3-[3-dimethyl aminopropyl]carbodiimide hydrochloride (EDC), succinimidyl-4-[N-maleimidomethylcyclohexane-1-carboxy-[6-amidocaproate] (SMCC) and its sulfonate (sulfo-SMCC), succinimidyl 6-[3-(2-pyridyldithio)-propionamide]hexanoate (SPDP) and its sulfonate (sulfo-SPDP), m-maleimidobenzoyl-N-hydroxysuccinimide ester (MBS) and its sulfonate (sulfo-MBS), succinimidyl [4-(p-maleimidophenyl)butyrate] (SMPB) and its sulfonate (sulfo-SMPB), etc.

Also, the crosslinker, which may be linked with the sulfhydryl group of cysteine located at the N-terminus of the fusion peptide represented by any one amino acid sequence represented by SEQ ID NOs: 60 to 67 after reducing the sulfhydryl group of cysteine at the C-terminus of SEQ ID NO: 3, may be tris(2-carboxyethyl)phosphine (TCEP), 5,50-dithiobis-(2-nitrobenzoic acid (DTNB), etc., but is not limited thereto.

In the present invention, the method of producing the fusion protein using the chemical conjugation method comprises steps of:

(a) activating the amine group of lysine, which is present in the linker moiety or exposed portion of the antibody or single-chain variable fragment thereof which targets the intracellular oncogenic protein or oncogenic mutant protein, with a crosslinker;
(b) linking the cancer cell-penetrating peptide to the antibody or single-chain variable fragment thereof activated with the crosslinker; and
(c) purifying the fusion protein wherein the cancer cell-penetrating peptide is linked to the antibody or single-chain variable fragment thereof.

Alternatively, step (a) of the above method may be a step of reducing the sulfhydryl group of the cysteine residue of the antibody or single-chain variable fragment thereof which targets the intracellular oncogenic protein or oncogenic mutant protein.

The fusion protein produced by the chemical conjugation method may be represented by the amino acid sequence of any one of SEQ ID NOs: 68 to 83, but is not limited thereto.

In an embodiment of the present invention, the fusion protein may be one wherein the cancer cell-penetrating peptide is linked via a crosslinker to the lysine or cysteine residue of the antibody or single-chain variable fragment thereof which targets the intracellular oncogenic protein or oncogenic mutant protein.

Preferably, the fusion protein may be one wherein the fusion peptide selected from the group consisting of SEQ ID NOs: 60 to 67 is chemically bound to the lysine or cysteine residue of any one single-chain variable fragment selected from the group consisting of SEQ ID NOs: 1 to 3 by a crosslinker.

In this case, wherein the residue is lysine, the crosslinker may be selected from the group consisting of 1,4-bis-maleimidobutane (BMB), 1,11-bis-maleimidotetraethyleneglycol (BM[PEO]4), 1-ethyl-3-[3-dimethyl aminopropyl]carbodiimide hydrochloride (EDC), succinimidyl-4-[N-maleimidomethylcyclohexane-1-carboxy-[6-amidocaproate]] (SMCC) and its sulfonate (sulfo-SMCC), succinimidyl 6-[3-(2-pyridyldithio)-propionamide]hexanoate (SPDP) and its sulfonate (sulfo-SPDP), m-maleimidobenzoyl-N-hydroxysuccinimide ester (MBS) and its sulfonate (sulfo- MBS), and succinimidyl [4-(p-maleimidophenyl)butyrate] (SMPB) and its sulfonate (sulfo-SMPB).

Meanwhile, when the residue is cysteine, the crosslinker may be tris(2-carboxyethyl)phosphine (TCEP) or 5,50-dithiobis-(2-nitrobenzoic acid (DTNB).

The KRAS mutant protein according to the present invention is known as an important factor in tumorigenesis that accelerates the growth of cancer cells, but exists inside the cell membrane, and thus the antibody or single-chain variable fragment thereof that targets the KRAS mutant protein has no significant inhibitory effect on the KRAS mutant protein. However, as a result of evaluating the tumor growth inhibitory effect of the KRAS mutant-targeting antibody or single-chain variable fragment thereof after introducing the cancer cell-penetrating peptide thereto, it was confirmed from the results of an in vitro experiment and an animal experiment that the KRAS mutant-targeting antibody or single-chain variable fragment having the cancer cell-penetrating ability had an effect of significantly inhibiting the growth of tumor cells.

Therefore, in another aspect, the present invention is directed to a pharmaceutical composition for treating a tumor comprising the fusion protein as an active ingredient.

In the present invention, the tumor may be at least one selected from the group consisting of non-small cell lung cancer, colorectal cancer, pancreatic cancer, bladder cancer, kidney cancer, thyroid cancer, breast cancer, colon cancer, liver cancer, brain tumor, skin cancer, melanoma, colorectal cancer, prostate cancer, and blood cancer, but is not limited thereto.

In the present invention, the pharmaceutical composition may be formulated in any one form selected from the group consisting of liquid formulations (for example, for injection) such as injections, formulations for oral administration, aqueous solutions, suspensions and emulsions, capsules, granules, tablets, and formulations for mucosal administration, but is not limited thereto. These formulations may be prepared by conventional methods used for formulation in the art or by methods disclosed in Remington's Pharmaceutical Science (latest edition), Mack Publishing Company, Easton PA, and may vary depending on each disease or components.

Meanwhile, the pharmaceutical composition of the present invention may further comprise at least one pharmaceutically acceptable carrier, in addition to the antibody or single-chain variable fragment thereof that has the ability to penetrate cancer cells and targets the KRAS mutant protein. The pharmaceutically acceptable carrier may be at least one selected from among saline, sterile water, Ringer's solution, buffered saline, dextrose solution, maltodextrin solution, glycerol, ethanol, and combinations thereof.

The pharmaceutical composition of the present invention may further comprise a pharmaceutically acceptable adjuvant, if necessary. The adjuvant may be one or more selected from the group consisting of excipients, diluents, dispersants, buffers, antimicrobial preservatives, bacteriostatic agents, surfactants, binders, lubricants, antioxidants, thickeners, and viscosity modifiers, but is not limited thereto.

The pharmaceutical composition according to the present invention may be administered orally or parenterally (e.g., intravenously, subcutaneously, intraperitoneally or topically) according to a desired method, and the dosage thereof may vary depending on the patient's weight, age, sex, health status and diet, the time of administration, the mode of administration, excretion rate, and the severity of disease and may be determined by an expert.

In one embodiment of the present invention, the single dose of the peptide may be 1 μg/kg to 100 mg/kg, preferably 5 μg/kg to 50 mg/kg, and may be administered once a day or 1 to 3 times a week, but the dose and administration frequency are not limited thereto In another aspect, the present invention is directed to a method for preventing or treating a tumor comprising a step of administering the fusion protein.

In another aspect, the present invention is directed to the use of the fusion protein for preventing or treating a tumor.

In another aspect, the present invention is directed to the use of the fusion protein in the manufacture of a medicament for treating a tumor.

EXAMPLES

Hereinafter, the present invention will be described in more detail with reference to examples. These examples serve merely to illustrate the present invention, and it will be obvious to those of ordinary skill in the art that the scope of the present invention is not to be construed as being limited by these examples.

Example 1: Preparation of Cancer Cell-Penetrating and KRAS Mutant-Targeting scFv by Protein Expression Method

Example 1-1: Expression of Cancer Cell-Penetrating and KRAS Mutant-Targeting scFv in *E. coli*

KRAS mutant scFv expression vectors, each comprising a KRAS mutant scFv and a cancer cell-penetrating peptide, were prepared by a PCR method using specific primers. The KRAS mutant scFv used in the present invention is any one of SEQ ID NOs: 1 to 3.

KRAS mutant scFv (SEQ ID NO: 1):
MAWVWTLLFLMAAAQSIQAEWIKQRPGQGLEWIGVIHPGNGGTNYNENF

KGKATLTADKSSSTAYMQLSSLTSDDSAVYFCASGNDGSYWGQGTTVTV

SSGGGGSGKGGSGGGGSGGGGSDIELTQSPSSLTVTAGEKVTMSCKSSQ

SLLNSGDQKIYLTWYQQKPGQPPKLLIYWASTRESGVPDRFTGSVSGTD

FTLTISSVQAEDLAVYYCQNDYNYPYTFGGGTKLEIKRGSENLYFQGGS

GKPIPNPLLGLDSTGGSGGSHHHHHH

KRAS mutant scFv (SEQ ID NO: 2):
MAQVKLQESGPELVRPGTSVKVSCKASGYAFTNYLIEWIKQRPGQGLEW

IGVIHPGNGGTNYNENFKGKATLTADKSSSTAYMQLSSLTSDDSAVYFC

ASGNDGSYWGQGTTVTVSSGGGGSGGGGSGGGGSDIELTQSPSSLTVTA

GEKVTMSCKSSQSLLNSGDQKIYLTWYQQKPGQPPKLLIYWASTRESGV

PDRFTGSVSGTDFTLTISSVQAEDLAVYYCQNDYNYPYTFGGGTKLEIK

RLEHHHHHH

KRAS mutant scFv (SEQ ID NO: 3):
MAWVWTLLFLMAAAQSIQAEWIKQRPGQGLEWIGVIHPGNGGTNYNENFK

GKATLTADKSSSTAYMQLSSLTSDDSAVYFCASGNDGSYWGQGTTVTVSS

GGGGSGKGGSGGGGSGGGGSDIELTQSPSSLTVTAGEKVTMSCKSSQSLL

NSGDQKIYLTWYQQKPGQPPKLLIYWASTRESGVPDRFTGSVSGTDFTLT

-continued

ISSVQAEDLAVYYCQNDYNYPYTFGGGTKCLEIKRGSENLYFQGGSGKPI

PNPLLGLDSTGGSGGSHHHHHH pET 21a(+) DNA was digested with Nde I and Xho I, and pMX DNA was also digested with Nde I and Xho I. The 767-bp Kras scFv gene fragment was recovered by an agarose electroelution method. To insert the gene fragment into a pET 21a(+) vector, the gene was amplified by PCR. The PCR was performed using the forward primer (5'-AAGGAGATATACATATGATGGCATGGGTTTGGAC-3') and the reverse primer (5'-AGCCCGAAGGGAATTCATTTGCAGATACAAAGTGTTTTTAGAGTTG-3'). Each digested vector and insert were mixed together at a ratio of 0.5 μg:1.0 μg, and ligated together using T4 DNA ligase in a ligation buffer comprising 500 mM Tris-HCl, 100 mM $MgCl_2$, 200 mM DTT and 10 mM ATP at 4° C. for 16 to 18 hours.

The recombinant DNA solution was transformed into *E. coli* DH5a and plated on LB+Amp solid medium, and transformants were selected.

A single colony of an *E. coli* Rosetta™ 2(DE3) Singles™ (Novagen) strain transformed with each plasmid was inoculated into 20 ml of LB comprising 10 μg/ml of ampicillin antibiotic, and cultured at 37° C. overnight. 1 ml of the culture was diluted in 200 ml of fresh LB comprising the same concentration of the antibiotic. The expression of KRAS scFv was induced by adding IPTG to a final concentration of 1 mM to the cells at an OD600 value of 0.8, followed by culturing overnight. The cells were harvested through centrifugation and lysed using 10 ml lysis buffer (50 mM $NaH_2PO_4$, 300 mM NaCl, pH 8.0). After sonication of the cells, the protein was separated into total, soluble and insoluble fractions by centrifugation at 12,000 g and 4° C. for 10 minutes, and analyzed by SDS-PAGE (S. I. Choi et al., Protein solubility and folding enhancement by interaction with RNA, PLoS ONE 3 (2008) e2677).

The isolated KRAS scFv was separated and purified by nickel chromatography (HisTrap™ excel Kit, GE Healthcare). Next, the nickel column was equilibrated with a buffer [50 mM $NaH_2PO_4$ (pH 8.0), 300 mM NaCl], and then an aqueous solution of the protein in the same buffer was applied to the column. After washing with the above containing 20 mM imidazole, the protein was separated using a buffer containing imidazole that was gradually increased from 50 mM to 500 mM. The separated proteins were collected and dialyzed using a desalting column (PD-10 Columns, GE Healthcare).

The linker and cancer cell-penetrating peptide sequences used in the present invention are shown in Table 1 below.

TABLE 1

| Type and position of linker | Cancer cell-penetrating peptide (CCPP) | Amino acid sequences of linker and cancer cell-penetrating peptide | SEQ ID NO | Linking portion of scFv |
|---|---|---|---|---|
| N terminus of CCPP-GGGGS | CCPP-1 (H4K) | GGGGS-HRRCNKNNKKR | 4 | C terminus |
| | CCPP-2 (H4P) | GGGGS-HRRCNPNNKKR | 5 | C terminus |
| | CCPP-3 (LMWP) | GGGGS-VSRRRRRRGGRRRR | 6 | C terminus |
| | CCPP-4 (hBD3-3) | GGGGS-GKCSTRGRKCCRRKK | 7 | C terminus |
| C terminus of CCPP-GGGGS | CCPP-1 (H4K) | HRRCNKNNKKR-GGGGS | 8 | N terminus |
| | CCPP-2 (H4P) | HRRCNPNNKKR-GGGGS | 9 | N terminus |
| | CCPP-3 (LMWP) | VSRRRRRRGGRRRR-GGGGS | 10 | N terminus |
| | CCPP-4 (hBD3-3) | GKCSTRGRKCCRRKK-GGGGS | 11 | N terminus |

Table 2 below shows the amino acid sequences of the fusion proteins for *E. coli* expression wherein the cancer cell-penetrating peptide and the KRAS mutant scFv are linked together.

TABLE 2

| Fusion protein | Amino acid sequence | SEQ ID NO |
|---|---|---|
| SEQ ID NO 1-GGGGS-H4K | MAWVWTLLFLMAAAQSIQAEWIKQRPGQGLEWIGVIHPGNGGTNYNE NFKGKATLTADKSSSTAYMQLSSLTSDDSAVYFCASGNDGSYWGQGT TVTVSSGGGGSGKGGSGGGGSGGGGSDIELTQSPSSLTVTAGEKVTM SCKSSQSLLNSGDQKIYLTWYQQKPGQPPKLLIYWASTRESGVPDRF TGSVSGTDFTLTISSVQAEDLAVYYCQNDYNYPYTFGGGTK - GGGGS - HRRCNKNNKKR - LEIKRGSENLYFQGGSGKPIPNPLLGLDSTGGSGGSHHHHHH | 12 |

TABLE 2-continued

| Fusion protein | Amino acid sequence | SEQ ID NO |
|---|---|---|
| SEQ ID NO 1-<br>GGGGS-H4P | MAWVWTLLFLMAAAQSIQAEWIKQRPGQGLEWIGVIHPGNGGTNYNE<br>NFKGKATLTADKSSSTAYMQLSSLTSDDSAVYFCASGNDGSYWGQGT<br>TVTVSSGGGGSGKGGSGGGGSGGGGSDIELTQSPSSLTVTAGEKVTM<br>SCKSSQSLLNSGDQKIYLTWYQQKPGQPPKLLIYWASTRESGVPDRF<br>TGSVSGTDFTLTISSVQAEDLAVYYCQNDYNYPYTFGGGTK -<br>GGGGS - HRRCNPNNKKR -<br>LEIKRGSENLYFQGGSGKPIPNPLLGLDSTGGSGGSHHHHHH | 13 |
| SEQ ID NO 1-<br>GGGGS-LMWP | MAWVWTLLFLMAAAQSIQAEWIKQRPGQGLEWIGVIHPGNGGTNYNE<br>NFKGKATLTADKSSSTAYMQLSSLTSDDSAVYFCASGNDGSYWGQGT<br>TVTVSSGGGGSGKGGSGGGGSGGGGSDIELTQSPSSLTVTAGEKVTM<br>SCKSSQSLLNSGDQKIYLTWYQQKPGQPPKLLIYWASTRESGVPDRF<br>TGSVSGTDFTLTISSVQAEDLAVYYCQNDYNYPYTFGGGTK -<br>GGGGS - VSRRRRRRGGRRRR-<br>LEIKRGSENLYFQGGSGKPIPNPLLGLDSTGGSGGSHHHHHH | 14 |
| SEQ ID NO 1-<br>GGGGS-hBD3-3 | MAWVWTLLFLMAAAQSIQAEWIKQRPGQGLEWIGVIHPGNGGTNYNE<br>NFKGKATLTADKSSSTAYMQLSSLTSDDSAVYFCASGNDGSYWGQGT<br>TVTVSSGGGGSGKGGSGGGGSGGGGSDIELTQSPSSLTVTAGEKVTM<br>SCKSSQSLLNSGDQKIYLTWYQQKPGQPPKLLIYWASTRESGVPDRF<br>TGSVSGTDFTLTISSVQAEDLAVYYCQNDYNYPYTFGGGTK -<br>GGGGS - GKCSTRGRKCCRRKK -<br>LEIKRGSENLYFQGGSGKPIPNPLLGLDSTGGSGGSHHHHHH | 15 |
| H4K-GGGGS-<br>SEQ ID NO 1 | MAWVWTLLFLMAAAQSIQA - HRRCNKNNKKR - GGGGS -<br>EWIKQRPGQGLEWIGVIHPGNGGTNYNENFKGKATLTADKSSSTAYM<br>QLSSLTSDDSAVYFCASGNDGSYWGQGTTVTVSSGGGGSGKGGSGGG<br>GSGGGGSDIELTQSPSSLTVTAGEKVTMSCKSSQSLLNSGDQKIYLT<br>WYQQKPGQPPKLLIYWASTRESGVPDRFTGSVSGTDFTLTISSVQAE<br>DLAVYYCQNDYNYPYTFGGGTKLEIKRGSENLYFQGGSGKPIPNPLL<br>GLDSTGGSGGSHHHHHH | 16 |
| H4P-GGGGS-<br>SEQ ID NO 1 | MAWVWTLLFLMAAAQSIQA - HRRCNPNNKKR - GGGGS -<br>EWIKQRPGQGLEWIGVIHPGNGGTNYNENFKGKATLTADKSSSTAYM<br>QLSSLTSDDSAVYFCASGNDGSYWGQGTTVTVSSGGGGSGKGGSGGG<br>GSGGGGSDIELTQSPSSLTVTAGEKVTMSCKSSQSLLNSGDQKIYLT<br>WYQQKPGQPPKLLIYWASTRESGVPDRFTGSVSGTDFTLTISSVQAE<br>DLAVYYCQNDYNYPYTFGGGTKLEIKRGSENLYFQGGSGKPIPNPLL<br>GLDSTGGSGGSHHHHHH | 17 |
| LMWP-GGGGS-<br>SEQ ID NO 1 | MAWVWTLLFLMAAAQSIQA - VSRRRRRRGGRRRR - GGGGS -<br>EWIKQRPGQGLEWIGVIHPGNGGTNYNENFKGKATLTADKSSSTAYM<br>QLSSLTSDDSAVYFCASGNDGSYWGQGTTVTVSSGGGGSGKGGSGGG<br>GSGGGGSDIELTQSPSSLTVTAGEKVTMSCKSSQSLLNSGDQKIYLT<br>WYQQKPGQPPKLLIYWASTRESGVPDRFTGSVSGTDFTLTISSVQAE<br>DLAVYYCQNDYNYPYTFGGGTKLEIKRGSENLYFQGGSGKPIPNPLL<br>GLDSTGGSGGSHHHHHH | 18 |
| hBD3-3-GGGGS-<br>SEQ ID NO 1 | MAWVWTLLFLMAAAQSIQA - GKCSTRGRKCCRRKK - GGGGS -<br>DLAVYYCQNDYNYPYTFGGGTKLEIKRGSENLYFQGGSGKPIPNPLL<br>EWIKQRPGQGLEWIGVIHPGNGGTNYNENFKGKATLTADKSSSTAYM<br>QLSSLTSDDSAVYFCASGNDGSYWGQGTTVTVSSGGGGSGKGGSGGG<br>GSGGGGSDIELTQSPSSLTVTAGEKVTMSCKSSQSLLNSGDQKIYLT<br>WYQQKPGQPPKLLIYWASTRESGVPDRFTGSVSGTDFTLTISSVQAE<br>DLAVYYCQNDYNYPYTFGGGTKLEIKRGSENLYFQGGSGKPIPNPLL<br>GLDSTGGSGGSHHHHHH | 19 |
| SEQ ID NO 2-<br>GGGGS-H4K | MAQVKLQESGPELVRPGTSVKVSCKASGYAFTNYLIEWIKQRPGQGL<br>EWIGVIHPGNGGTNYNENFKGKATLTADKSSSTAYMQLSSLTSDDSA<br>VYFCASGNDGSYWGQGTTVTVSSGGGGSGGGGSGGGGSDIELTQSPS<br>SLTVTAGEKVTMSCKSSQSLLNSGDQKIYLTWYQQKPGQPPKLLIYW<br>ASTRESGVPDRFTGSVSGTDFTLTISSVQAEDLAVYYCQNDYNYPYT<br>FGGGTK - GGGGS - HRRCNKNNKKR - LEIKRLEHHHHHH | 20 |
| SEQ ID NO 2-<br>GGGGS-H4P | MAQVKLQESGPELVRPGTSVKVSCKASGYAFTNYLIEWIKQRPGQGL<br>EWIGVIHPGNGGTNYNENFKGKATLTADKSSSTAYMQLSSLTSDDSA<br>VYFCASGNDGSYWGQGTTVTVSSGGGGSGGGGSGGGGSDIELTQSPS<br>SLTVTAGEKVTMSCKSSQSLLNSGDQKIYLTWYQQKPGQPPKLLIYW<br>ASTRESGVPDRFTGSVSGTDFTLTISSVQAEDLAVYYCQNDYNYPYT<br>FGGGTK - GGGGS - HRRCNPNNKKR - LEIKRLEHHHHHH | 21 |

TABLE 2-continued

| Fusion protein | Amino acid sequence | SEQ ID NO |
|---|---|---|
| SEQ ID NO 2-<br>GGGGS-LMWP | MAQVKLQESGPELVRPGTSVKVSCKASGYAFTNYLIEWIKQRPGQGL<br>EWIGVIHPGNGGTNYNENFKGKATLTADKSSSTAYMQLSSLTSDDSA<br>VYFCASGNDGSYWGQGTTVTVSSGGGGSGGGGSGGGGSDIELTQSPS<br>SLTVTAGEKVTMSCKSSQSLLNSGDQKIYLTWYQQKPGQPPKLLIYW<br>ASTRESGVPDRFTGSVSGTDFTLTISSVQAEDLAVYYCQNDYNYPYT<br>FGGGTK - GGGGS - VSRRRRRRGGRRRR -LEIKRLEHHHHHH | 22 |
| SEQ ID NO 2-<br>GGGGS-hBD3-3 | MAQVKLQESGPELVRPGTSVKVSCKASGYAFTNYLIEWIKQRPGQGL<br>EWIGVIHPGNGGTNYNENFKGKATLTADKSSSTAYMQLSSLTSDDSA<br>VYFCASGNDGSYWGQGTTVTVSSGGGGSGGGGSGGGGSDIELTQSPS<br>SLTVTAGEKVTMSCKSSQSLLNSGDQKIYLTWYQQKPGQPPKLLIYW<br>ASTRESGVPDRFTGSVSGTDFTLTISSVQAEDLAVYYCQNDYNYPYT<br>FGGGTK - GGGGS - GKCSTRGRKCCRRKK - LEIKRLEHHHHHH | 23 |
| H4K-GGGGS-<br>SEQ ID NO 2 | MAQVKLQESGPELVRPGTSVKVSCKASGYAFTNYLI -<br>HRRCNKNNKKR - GGGGS -<br>EWIKQRPGQGLEWIGVIHPGNGGTNYNENFKGKATLTADKSSSTAYM<br>QLSSLTSDDSAVYFCASGNDGSYWGQGTTVTVSSGGGGSGKGGSGGG<br>GSGGGGSDIELTQSPSSLTVTAGEKVTMSCKSSQSLLNSGDQKIYLT<br>WYQQKPGQPPKLLIYWASTRESGVPDRFTGSVSGTDFTLTISSVQAE<br>DLAVYYCQNDYNYPYTFGGGTKLEIKRLEHHHHHH | 24 |
| H4P-GGGGS-<br>SEQ ID NO 2 | MAQVKLQESGPELVRPGTSVKVSCKASGYAFTNYLI -<br>HRRCNPNNKKR - GGGGS -<br>EWIKQRPGQGLEWIGVIHPGNGGTNYNENFKGKATLTADKSSSTAYM<br>QLSSLTSDDSAVYFCASGNDGSYWGQGTTVTVSSGGGGSGKGGSGGG<br>GSGGGGSDIELTQSPSSLTVTAGEKVTMSCKSSQSLLNSGDQKIYLT<br>WYQQKPGQPPKLLIYWASTRESGVPDRFTGSVSGTDFTLTISSVQAE<br>DLAVYYCQNDYNYPYTFGGGTKLEIKRLEHHHHHH | 25 |
| LMWP-GGGGS-<br>SEQ ID NO 2 | MAQVKLQESGPELVRPGTSVKVSCKASGYAFTNYLI-<br>VSRRRRRRGGRRRR - GGGGS -<br>EWIKQRPGQGLEWIGVIHPGNGGTNYNENFKGKATLTADKSSSTAYM<br>QLSSLTSDDSAVYFCASGNDGSYWGQGTTVTVSSGGGGSGKGGSGGG<br>GSGGGGSDIELTQSPSSLTVTAGEKVTMSCKSSQSLLNSGDQKIYLT<br>WYQQKPGQPPKLLIYWASTRESGVPDRFTGSVSGTDFTLTISSVQAE<br>DLAVYYCQNDYNYPYTFGGGTKLEIKRLEHHHHHH | 26 |
| hBD3-3-GGGGS-<br>SEQ ID NO 2 | MAQVKLQESGPELVRPGTSVKVSCKASGYAFTNYLI -<br>GKCSTRGRKCCRRKK - GGGGS -<br>EWIKQRPGQGLEWIGVIHPGNGGTNYNENFKGKATLTADKSSSTAYM<br>QLSSLTSDDSAVYFCASGNDGSYWGQGTTVTVSSGGGGSGKGGSGGG<br>GSGGGGSDIELTQSPSSLTVTAGEKVTMSCKSSQSLLNSGDQKIYLT<br>WYQQKPGQPPKLLIYWASTRESGVPDRFTGSVSGTDFTLTISSVQAE<br>DLAVYYCQNDYNYPYTFGGGTKLEIKRLEHHHHHH | 27 |

Figure 3A:
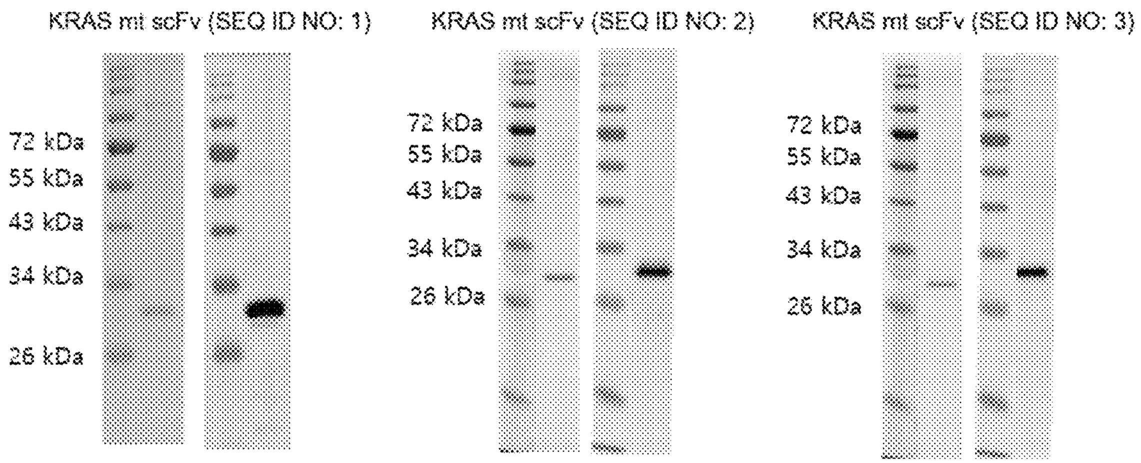
FIGS. 3*a*, 3*b* and 3*c* show the results of SDS-PAGE and Western blot analysis of cancer cell-penetrating KRAS mutant antibodies and scFvs after expression and purification.

FIGS. 3*a*. 3b and 3c show the results of SDS-PAGE and Western blot analysis of the KRAS mutant-targeting purified antibodies or single-chain variable fragments of SEQ ID NOs: 1, 2 and 3.

Example 1-2: Expression of Cancer Cell-Penetrating and KRAS Mutant-Targeting scFv in Mammalian Cells KRAS mutant scFv expression vectors (each containing a KRAS mutant scFv and a cancer cell-penetrating peptide) for use in mammalian cells were constructed by a PCR method using specific primers.

Table 3 below shows the amino acid sequences of the fusion proteins wherein the cancer cell-penetrating peptide is linked to the KRAS mutant scFv and which are each cloned into the pcDNA3.4-TOPO vector for mammalian cell expression.

TABLE 3

| Fusion protein | Amino acid sequence | SEQ ID NO |
|---|---|---|
| SEQ ID NO 1-<br>GGGGS-H4K | MAWVWTLLFLMAAAQSIQAEWIKQRPGQGLEWIGVIHPGNGGTNYNE<br>NFKGKATLTADKSSSTAYMQLSSLTSDDSAVYFCASGNDGSYWGQGT<br>TVTVSSGGGGSGKGGSGGGGSGGGGSDIELTQSPSSLTVTAGEKVTM<br>SCKSSQSLLNSGDQKIYLTWYQQKPGQPPKLLIYWASTRESGVPDRF<br>TGSVSGTDFTLTISSVQAEDLAVYYCQNDYNYPYTFGGGTK -<br>GGGGS - HRRCNKNNKKR -<br>LEIKRGSENLYFQGGSGKPIPNPLLGLDSTGGSGGSHHHHHH | 28 |

TABLE 3-continued

| Fusion protein | Amino acid sequence | SEQ ID NO |
|---|---|---|
| SEQ ID NO 1-GGGGS-H4P | MAWVWTLLFLMAAAQSIQAEWIKQRPGQGLEWIGVIHPGNGGTNYNENFKGKATLTADKSSSTAYMQLSSLTSDDSAVYFCASGNDGSYWGQGTTVTVSSGGGGSGKGGSGGGGSGGGGSDIELTQSPSSLTVTAGEKVTMSCKSSQSLLNSGDQKIYLTWYQQKPGQPPKLLIYWASTRESGVPDRFTGSVSGTDFTLTISSVQAEDLAVYYCQNDYNYPYTFGGGTK - GGGGS - HRRCNPNNKKR - LEIKRGSENLYFQGGSGKPIPNPLLGLDSTGGSGGSHHHHHH | 29 |
| SEQ ID NO 1-GGGGS-LMWP | MAWVWTLLFLMAAAQSIQAEWIKQRPGQGLEWIGVIHPGNGGTNYNENFKGKATLTADKSSSTAYMQLSSLTSDDSAVYFCASGNDGSYWGQGTTVTVSSGGGGSGKGGSGGGGSGGGGSDIELTQSPSSLTVTAGEKVTMSCKSSQSLLNSGDQKIYLTWYQQKPGQPPKLLIYWASTRESGVPDRFTGSVSGTDFTLTISSVQAEDLAVYYCQNDYNYPYTFGGGTK - GGGGS - VSRRRRRRGGRRRR-LEIKRGSENLYFQGGSGKPIPNPLLGLDSTGGSGGSHHHHHH | 30 |
| SEQ ID NO 1-GGGGS-hBD3-3 | MAWVWTLLFLMAAAQSIQAEWIKQRPGQGLEWIGVIHPGNGGTNYNENFKGKATLTADKSSSTAYMQLSSLTSDDSAVYFCASGNDGSYWGQGTTVTVSSGGGGSGKGGSGGGGSGGGGSDIELTQSPSSLTVTAGEKVTMSCKSSQSLLNSGDQKIYLTWYQQKPGQPPKLLIYWASTRESGVPDRFTGSVSGTDFTLTISSVQAEDLAVYYCQNDYNYPYTFGGGTK - GGGGS - GKCSTRGRKCCRRKK - LEIKRGSENLYFQGGSGKPIPNPLLGLDSTGGSGGSHHHHHH | 31 |
| H4K-GGGGS-SEQ ID NO 1 | MAWVWTLLFLMAAAQSIQA - HRRCNKNNKKR - GGGGS EWIKQRPGQGLEWIGVIHPGNGGTNYNENFKGKATLTADKSSSTAYMQLSSLTSDDSAVYFCASGNDGSYWGQGTTVTVSSGGGGSGKGGSGGGGSGGGGSDIELTQSPSSLTVTAGEKVTMSCKSSQSLLNSGDQKIYLTWYQQKPGQPPKLLIYWASTRESGVPDRFTGSVSGTDFTLTISSVQAEDLAVYYCQNDYNYPYTFGGGTKLEIKRGSENLYFQGGSGKPIPNPLLGLDSTGGSGGSHHHHHH | 32 |
| H4P-GGGGS-SEQ ID NO 1 | MAWVWTLLFLMAAAQSIQA - HRRCNPNNKKR - GGGGS - EWIKQRPGQGLEWIGVIHPGNGGTNYNENFKGKATLTADKSSSTAYMQLSSLTSDDSAVYFCASGNDGSYWGQGTTVTVSSGGGGSGKGGSGGGGSGGGGSDIELTQSPSSLTVTAGEKVTMSCKSSQSLLNSGDQKIYLTWYQQKPGQPPKLLIYWASTRESGVPDRFTGSVSGTDFTLTISSVQAEDLAVYYCQNDYNYPYTFGGGTKLEIKRGSENLYFQGGSGKPIPNPLLGLDSTGGSGGSHHHHHH | 33 |
| LMWP-GGGGS-SEQ ID NO 1 | MAWVWTLLFLMAAAQSIQA- VSRRRRRRGGRRRR - GGGGS - EWIKQRPGQGLEWIGVIHPGNGGTNYNENFKGKATLTADKSSSTAYMQLSSLTSDDSAVYFCASGNDGSYWGQGTTVTVSSGGGGSGKGGSGGGGSGGGGSDIELTQSPSSLTVTAGEKVTMSCKSSQSLLNSGDQKIYLTWYQQKPGQPPKLLIYWASTRESGVPDRFTGSVSGTDFTLTISSVQAEDLAVYYCQNDYNYPYTFGGGTKLEIKRGSENLYFQGGSGKPIPNPLLGLDSTGGSGGSHHHHHH | 34 |
| hBD3-3-GGGGS-SEQ ID NO 1 | MAWVWTLLFLMAAAQSIQA - GKCSTRGRKCCRRKK - GGGGS - EWIKQRPGQGLEWIGVIHPGNGGTNYNENFKGKATLTADKSSSTAYMQLSSLTSDDSAVYFCASGNDGSYWGQGTTVTVSSGGGGSGKGGSGGGGSGGGGSDIELTQSPSSLTVTAGEKVTMSCKSSQSLLNSGDQKIYLTWYQQKPGQPPKLLIYWASTRESGVPDRFTGSVSGTDFTLTISSVQAEDLAVYYCQNDYNYPYTFGGGTKLEIKRGSENLYFQGGSGKPIPNPLLGLDSTGGSGGSHHHHHH | 35 |
| SEQ ID NO 2-GGGGS-H4K | MAQVKLQESGPELVRPGTSVKVSCKASGYAFTNYLIEWIKQRPGQGLEWIGVIHPGNGGTNYNENFKGKATLTADKSSSTAYMQLSSLTSDDSAVYFCASGNDGSYWGQGTTVTVSSGGGGSGGGGSGGGGSDIELTQSPSSLTVTAGEKVTMSCKSSQSLLNSGDQKIYLTWYQQKPGQPPKLLIYWASTRESGVPDRFTGSVSGTDFTLTISSVQAEDLAVYYCQNDYNYPYTFGGGTK - GGGGS - HRRCNKNNKKR - LEIKRLEHHHHHH | 36 |
| SEQ ID NO 2-GGGGS-H4P | MAQVKLQESGPELVRPGTSVKVSCKASGYAFTNYLIEWIKQRPGQGLEWIGVIHPGNGGTNYNENFKGKATLTADKSSSTAYMQLSSLTSDDSAVYFCASGNDGSYWGQGTTVTVSSGGGGSGGGGSGGGGSDIELTQSPSSLTVTAGEKVTMSCKSSQSLLNSGDQKIYLTWYQQKPGQPPKLLIYWASTRESGVPDRFTGSVSGTDFTLTISSVQAEDLAVYYCQNDYNYPYTFGGGTK - GGGGS - HRRCNPNNKKR - LEIKRLEHHHHHH | 37 |
| SEQ ID NO 2-GGGGS-LMWP | MAQVKLQESGPELVRPGTSVKVSCKASGYAFTNYLIEWIKQRPGQGLEWIGVIHPGNGGTNYNENFKGKATLTADKSSSTAYMQLSSLTSDDSAVYFCASGNDGSYWGQGTTVTVSSGGGGSGGGGSGGGGSDIELTQSPSSLTVTAGEKVTMSCKSSQSLLNSGDQKIYLTWYQQKPGQPPKLLIYWASTRESGVPDRFTGSVSGTDFTLTISSVQAEDLAVYYCQNDYNYPYTFGGGTK - GGGGS - VSRRRRRRGGRRRR -LEIKRLEHHHHHH | 38 |

TABLE 3-continued

| Fusion protein | Amino acid sequence | SEQ ID NO |
|---|---|---|
| SEQ ID NO 2-<br>GGGGS-hBD3-3 | MAQVKLQESGPELVRPGTSVKVSCKASGYAFTNYLIEWIKQRPGQGL<br>EWIGVIHPGNGGTNYNENFKGKATLTADKSSSTAYMQLSSLTSDDSA<br>VYFCASGNDGSYWGQGTTVTVSSGGGGSGGGGSGGGGSDIELTQSPS<br>SLTVTAGEKVTMSCKSSQSLLNSGDQKIYLTWYQQKPGQPPKLLIYW<br>ASTRESGVPDRFTGSVSGTDFTLTISSVQAEDLAVYYCQNDYNYPYT<br>FGGGTK - GGGGS - GKCSTRGRKCCRRKK - LEIKRLEHHHHHH | 39 |
| H4K-GGGGS-<br>SEQ ID NO 2 | MAQVKLQESGPELVRPGTSVKVSCKASGYAFTNYLI -<br>HRRCNKNNKKR - GGGGS -<br>EWIKQRPGQGLEWIGVIHPGNGGTNYNENFKGKATLTADKSSSTAYM<br>QLSSLTSDDSAVYFCASGNDGSYWGQGTTVTVSSGGGGSGKGGSGGG<br>GSGGGGSDIELTQSPSSLTVTAGEKVTMSCKSSQSLLNSGDQKIYLT<br>WYQQKPGQPPKLLIYWASTRESGVPDRFTGSVSGTDFTLTISSVQAE<br>DLAVYYCQNDYNYPYTFGGGTKLEIKRLEHHHHHH | 40 |
| H4P-GGGGS-<br>SEQ ID NO 2 | MAQVKLQESGPELVRPGTSVKVSCKASGYAFTNYLI -<br>HRRCNPNNKKR - GGGGS -<br>EWIKQRPGQGLEWIGVIHPGNGGTNYNENFKGKATLTADKSSSTAYM<br>QLSSLTSDDSAVYFCASGNDGSYWGQGTTVTVSSGGGGSGKGGSGGG<br>GSGGGGSDIELTQSPSSLTVTAGEKVTMSCKSSQSLLNSGDQKIYLT<br>WYQQKPGQPPKLLIYWASTRESGVPDRFTGSVSGTDFTLTISSVQAE<br>DLAVYYCQNDYNYPYTFGGGTKLEIKRLEHHHHHH | 41 |
| LMWP-GGGGS-<br>SEQ ID NO 2 | MAQVKLQESGPELVRPGTSVKVSCKASGYAFTNYLI-<br>VSRRRRRRGGRRRR - GGGGS -<br>EWIKQRPGQGLEWIGVIHPGNGGTNYNENFKGKATLTADKSSSTAYM<br>QLSSLTSDDSAVYFCASGNDGSYWGQGTTVTVSSGGGGSGKGGSGGG<br>GSGGGGSDIELTQSPSSLTVTAGEKVTMSCKSSQSLLNSGDQKIYLT<br>WYQQKPGQPPKLLIYWASTRESGVPDRFTGSVSGTDFTLTISSVQAE<br>DLAVYYCQNDYNYPYTFGGGTKLEIKRLEHHHHHH | 42 |
| hBD3-3-GGGGS-<br>SEQ ID NO 2 | MAQVKLQESGPELVRPGTSVKVSCKASGYAFTNYLI -<br>GKCSTRGRKCCRRKK - GGGGS -<br>EWIKQRPGQGLEWIGVIHPGNGGTNYNENFKGKATLTADKSSSTAYM<br>QLSSLTSDDSAVYFCASGNDGSYWGQGTTVTVSSGGGGSGKGGSGGG<br>GSGGGGSDIELTQSPSSLTVTAGEKVTMSCKSSQSLLNSGDQKIYLT<br>WYQQKPGQPPKLLIYWASTRESGVPDRFTGSVSGTDFTLTISSVQAE<br>DLAVYYCQNDYNYPYTFGGGTKLEIKRLEHHHHHHH | 43 |

Table 4 below shows the amino acid sequences of the fusion proteins wherein the cancer cell-penetrating peptide is linked to the KRAS mutant scFv and which are each cloned into the pcDNA3.1-TOPO vector for mammalian cell expression.

TABLE 4

| Fusion protein | Amino acid sequence | SEQ ID NO |
|---|---|---|
| SEQ ID NO 1-<br>GGGGS-H4K | MAWVWTLLFLMAAAQSIQAEWIKQRPGQGLEWIGVIHPGNGGTNYNENFKGK<br>ATLTADKSSSTAYMQLSSLTSDDSAVYFCASGNDGSYWGQGTTVTVSSGGGG<br>SGKGGSGGGGSGGGGSDIELTQSPSSLTVTAGEKVTMSCKSSQSLLNSGDQK<br>IYLTWYQQKPGQPPKLLIYWASTRESGVPDRFTGSVSGTDFTLTISSVQAED<br>LAVYYCQNDYNYPYTFGGGTK - GGGGS - HRRCNKNNKKR -<br>LEIKRGSENLYFQGGSGKPIPNPLLGLDSTGGSGGSHHHHHH | 44 |
| SEQ ID NO 1-<br>GGGGS-H4P | MAWVWTLLFLMAAAQSIQAEWIKQRPGQGLEWIGVIHPGNGGTNYNENFKGK<br>ATLTADKSSSTAYMQLSSLTSDDSAVYFCASGNDGSYWGQGTTVTVSSGGGG<br>SGKGGSGGGGSGGGGSDIELTQSPSSLTVTAGEKVTMSCKSSQSLLNSGDQK<br>IYLTWYQQKPGQPPKLLIYWASTRESGVPDRFTGSVSGTDFTLTISSVQAED<br>LAVYYCQNDYNYPYTFGGGTK - GGGGS - HRRCNPNNKKR -<br>LEIKRGSENLYFQGGSGKPIPNPLLGLDSTGGSGGSHHHHHH | 45 |
| SEQ ID NO 1-<br>GGGGS-LMWP | MAWVWTLLFLMAAAQSIQAEWIKQRPGQGLEWIGVIHPGNGGTNYNENFKGK<br>ATLTADKSSSTAYMQLSSLTSDDSAVYFCASGNDGSYWGQGTTVTVSSGGGG<br>SGKGGSGGGGSGGGGSDIELTQSPSSLTVTAGEKVTMSCKSSQSLLNSGDQK<br>IYLTWYQQKPGQPPKLLIYWASTRESGVPDRFTGSVSGTDFTLTISSVQAED<br>LAVYYCONDYNYPYTFGGGTK - GGGGS - VSRRRRRRGGRRRR-<br>LEIKRGSENLYFQGGSGKPIPNPLLGLDSTGGSGGSHHHHHH | 46 |

TABLE 4-continued

| Fusion protein | Amino acid sequence | SEQ ID NO |
|---|---|---|
| SEQ ID NO 1-GGGGS-hBD3-3 | MAWVWTLLFLMAAAQSIQAEWIKQRPGQGLEWIGVIHPGNGGTNYNENFKGK ATLTADKSSSTAYMQLSSLTSDDSAVYFCASGNDGSYWGQGTTVTVSSGGGG SGKGGSGGGGSGGGGSDIELTQSPSSLTVTAGEKVTMSCKSSQSLLNSGDQK IYLTWYQQKPGQPPKLLIYWASTRESGVPDRFTGSVSGTDFTLTISSVQAED LAVYYCQNDYNYPYTFGGGTK - GGGGS - GKCSTRGRKCCRRKK - LEIKRGSENLYFQGGSGKPIPNPLLGLDSTGGSGGSHHHHHH | 47 |
| H4K-GGGGS-SEQ ID NO 1 | MAWVWTLLFLMAAAQSIQA - HRRCNKNNKKR - GGGGS - EWIKQRPGQGLEWIGVIHPGNGGTNYNENFKGKATLTADKSSSTAYMQLSSL TSDDSAVYFCASGNDGSYWGQGTTVTVSSGGGGSGKGGSGGGGSGGGGSDIE LTQSPSSLTVTAGEKVTMSCKSSQSLLNSGDQKIYLTWYQQKPGQPPKLLIY WASTRESGVPDRFTGSVSGTDFTLTISSVQAEDLAVYYCQNDYNYPYTFGGG TKLEIKRGSENLYFQGGSGKPIPNPLLGLDSTGGSGGSHHHHHH | 48 |
| H4P-GGGGS-SEQ ID NO 1 | MAWVWTLLFLMAAAQSIQA - HRRCNPNNKKR - GGGGS - EWIKQRPGQGLEWIGVIHPGNGGTNYNENFKGKATLTADKSSSTAYMQLSSL TSDDSAVYFCASGNDGSYWGQGTTVTVSSGGGGSGKGGSGGGGSGGGGSDIE LTQSPSSLTVTAGEKVTMSCKSSQSLLNSGDQKIYLTWYQQKPGQPPKLLIY WASTRESGVPDRFTGSVSGTDFTLTISSVQAEDLAVYYCQNDYNYPYTFGGG TKLEIKRGSENLYFQGGSGKPIPNPLLGLDSTGGSGGSHHHHHH | 49 |
| LMWP-GGGGS-SEQ ID NO 1 | MAWVWTLLFLMAAAQSIQA- VSRRRRRRGGRRRR - GGGGS - EWIKQRPGQGLEWIGVIHPGNGGTNYNENFKGKATLTADKSSSTAYMQLSSL TSDDSAVYFCASGNDGSYWGQGTTVTVSSGGGGSGKGGSGGGGSGGGGSDIE LTQSPSSLTVTAGEKVTMSCKSSQSLLNSGDQKIYLTWYQQKPGQPPKLLIY WASTRESGVPDRFTGSVSGTDFTLTISSVQAEDLAVYYCQNDYNYPYTFGGG TKLEIKRGSENLYFQGGSGKPIPNPLLGLDSTGGSGGSHHHHHH | 50 |
| hBD3-3-GGGGS-SEQ ID NO 1 | MAWVWTLLFLMAAAQSIQA - GKCSTRGRKCCRRKK - GGGGS - EWIKQRPGQGLEWIGVIHPGNGGTNYNENFKGKATLTADKSSSTAYMQLSSL TSDDSAVYFCASGNDGSYWGQGTTVTVSSGGGGSGKGGSGGGGSGGGGSDIE LTQSPSSLTVTAGEKVTMSCKSSQSLLNSGDQKIYLTWYQQKPGQPPKLLIY WASTRESGVPDRFTGSVSGTDFTLTISSVQAEDLAVYYCQNDYNYPYTFGGG TKLEIKRGSENLYFQGGSGKPIPNPLLGLDSTGGSGGSHHHHHH | 51 |
| SEQ ID NO 2-GGGGS-H4K | MAQVKLQESGPELVRPGTSVKVSCKASGYAFTNYLIEWIKQRPGQGLEWIGV IHPGNGGTNYNENFKGKATLTADKSSSTAYMQLSSLTSDDSAVYFCASGNDG SYWGQGTTVTVSSGGGGSGGGGSGGGGSDIELTQSPSSLTVTAGEKVTMSCK SSQSLLNSGDQKIYLTWYQQKPGQPPKLLIYWASTRESGVPDRFTGSVSGTD FTLTISSVQAEDLAVYYCQNDYNYPYTFGGGTK - GGGGS - HRRCNKNNKKR - LEIKRLEHHHHHH | 52 |
| SEQ ID NO 2-GGGGS-H4P | MAQVKLQESGPELVRPGTSVKVSCKASGYAFTNYLIEWIKQRPGQGLEWIGV IHPGNGGTNYNENFKGKATLTADKSSSTAYMQLSSLTSDDSAVYFCASGNDG SYWGQGTTVTVSSGGGGSGGGGSGGGGSDIELTQSPSSLTVTAGEKVTMSCK SSQSLLNSGDQKIYLTWYQQKPGQPPKLLIYWASTRESGVPDRFTGSVSGTD FTLTISSVQAEDLAVYYCQNDYNYPYTFGGGTK - GGGGS - HRRCNPNNKKR - LEIKRLEHHHHHH | 53 |
| SEQ ID NO 2-GGGGS-LMWP | MAQVKLQESGPELVRPGTSVKVSCKASGYAFTNYLIEWIKQRPGQGLEWIGV IHPGNGGTNYNENFKGKATLTADKSSSTAYMQLSSLTSDDSAVYFCASGNDG SYWGQGTTVTVSSGGGGSGGGGSGGGGSDIELTQSPSSLTVTAGEKVTMSCK SSQSLLNSGDQKIYLTWYQQKPGQPPKLLIYWASTRESGVPDRFTGSVSGTD FTLTISSVQAEDLAVYYCQNDYNYPYTFGGGTK - GGGGS - VSRRRRRRGGRRRR -LEIKRLEHHHHHH | 54 |
| SEQ ID NO 2-GGGGS-hBD3-3 | MAQVKLQESGPELVRPGTSVKVSCKASGYAFTNYLIEWIKQRPGQGLEWIGV IHPGNGGTNYNENFKGKATLTADKSSSTAYMQLSSLTSDDSAVYFCASGNDG SYWGQGTTVTVSSGGGGSGGGGSGGGGSDIELTQSPSSLTVTAGEKVTMSCK SSQSLLNSGDQKIYLTWYQQKPGQPPKLLIYWASTRESGVPDRFTGSVSGTD FTLTISSVQAEDLAVYYCQNDYNYPYTFGGGTK - GGGGS - GKCSTRGRKCCRRKK - LEIKRLEHHHHHH | 55 |
| H4K-GGGGS-SEQ ID NO 2 | MAQVKLQESGPELVRPGTSVKVSCKASGYAFTNYLI - HRRCNKNNKKR - GGGGS - EWIKQRPGQGLEWIGVIHPGNGGTNYNENFKGKATLTADKSSSTAYMQLSSL TSDDSAVYFCASGNDGSYWGQGTTVTVSSGGGGSGKGGSGGGGSGGGGSDIE LTQSPSSLTVTAGEKVTMSCKSSQSLLNSGDQKIYLTWYQQKPGQPPKLLIY WASTRESGVPDRFTGSVSGTDFTLTISSVQAEDLAVYYCQNDYNYPYTFGGG TKLEIKRLEHHHHHH | 56 |

TABLE 4-continued

| Fusion protein | Amino acid sequence | SEQ ID NO |
|---|---|---|
| H4P-GGGGS-SEQ ID NO 2 | MAQVKLQESGPELVRPGTSVKVSCKASGYAFTNYLI - HRRCNPNNKKR - GGGGS - EWIKQRPGQGLEWIGVIHPGNGGTNYNENFKGKATLTADKSSSTAYMQLSSLTSDDSAVYFCASGNDGSYWGQGTTVTVSSGGGGSGKGGSGGGGSGGGGSDIELTQSPSSLTVTAGEKVTMSCKSSQSLLNSGDQKIYLTWYQQKPGQPPKLLIYWASTRESGVPDRFTGSVSGTDFTLTISSVQAEDLAVYYCQNDYNYPYTFGGGTKLEIKRLEHHHHHH | 57 |
| LMWP-GGGGS-SEQ ID NO 2 | MAQVKLQESGPELVRPGTSVKVSCKASGYAFTNYLI- VSRRRRRRGGRRRR - GGGGS - EWIKQRPGQGLEWIGVIHPGNGGTNYNENFKGKATLTADKSSSTAYMQLSSLTSDDSAVYFCASGNDGSYWGQGTTVTVSSGGGGSGKGGSGGGGSGGGGSDIELTQSPSSLTVTAGEKVTMSCKSSQSLLNSGDQKIYLTWYQQKPGQPPKLLIYWASTRESGVPDRFTGSVSGTDFTLTISSVQAEDLAVYYCQNDYNYPYTFGGGTKLEIKRLEHHHHHH | 58 |
| hBD3-3-GGGGS-SEQ ID NO 2 | MAQVKLQESGPELVRPGTSVKVSCKASGYAFTNYLI - GKCSTRGRKCCRRKK - GGGGS - EWIKQRPGQGLEWIGVIHPGNGGTNYNENFKGKATLTADKSSSTAYMQLSSLTSDDSAVYFCASGNDGSYWGQGTTVTVSSGGGGSGKGGSGGGGSGGGGSDIELTQSPSSLTVTAGEKVTMSCKSSQSLLNSGDQKIYLTWYQQKPGQPPKLLIYWASTRESGVPDRFTGSVSGTDFTLTISSVQAEDLAVYYCQNDYNYPYTFGGGTKLEIKRLEHHHHHHH | 59 |

Table 5 below shows the amino acid sequences of the fusion proteins wherein the cancer cell-penetrating peptide is linked to the KRAS mutant scFv and which are each cloned into the pcDNA3.4-TOPO for mammalian cell expression.

TABLE 5

| Fusion protein | Amino acid sequence | SEQ ID NO |
|---|---|---|
| SEQ ID NO 2-GGGGSGGGGSGGGGS -H4K | MAQVKLQESGPELVRPGTSVKVSCKASGYAFTNYLIEWIKQRPGQGLEWIGVIHPGNGGTNYNENFKGKATLTADKSSSTAYMQLSSLTSDDSAVYFCASGNDGSYWGQGTTVTVSSGGGGSGGGGSGGGGSDIELTQSPSSLTVTAGEKVTMSCKSSQSLLNSGDQKIYLTWYQQKPGQPPKLLIYWASTRESGVPDRFTGSVSGTDFTLTISSVQAEDLAVYYCQNDYNYPYTFGGGTK - GGGGSGGGGSGGGGS - HRRCNKNNKKR - LEIKRLEHHHHHH | 90 |
| SEQ ID NO 2-GGGGSGGGGSGGGGS -H4P | MAQVKLQESGPELVRPGTSVKVSCKASGYAFTNYLIEWIKQRPGQGLEWIGVIHPGNGGTNYNENFKGKATLTADKSSSTAYMQLSSLTSDDSAVYFCASGNDGSYWGQGTTVTVSSGGGGSGGGGSGGGGSDIELTQSPSSLTVTAGEKVTMSCKSSQSLLNSGDQKIYLTWYQQKPGQPPKLLIYWASTRESGVPDRFTGSVSGTDFTLTISSVQAEDLAVYYCQNDYNYPYTFGGGTK- GGGGSGGGGSGGGGS - HRRCNPNNKKR - LEIKRLEHHHHHH | 91 |
| SEQ ID NO 2-GGGGSGGGGSGGGGS -LMWP | MAQVKLQESGPELVRPGTSVKVSCKASGYAFTNYLIEWIKQRPGQGLEWIGVIHPGNGGTNYNENFKGKATLTADKSSSTAYMQLSSLTSDDSAVYFCASGNDGSYWGQGTTVTVSSGGGGSGGGGSGGGGSDIELTQSPSSLTVTAGEKVTMSCKSSQSLLNSGDQKIYLTWYQQKPGQPPKLLIYWASTRESGVPDRFTGSVSGTDFTLTISSVQAEDLAVYYCQNDYNYPYTFGGGTK - GGGGSGGGGSGGGGS - VSRRRRRRGGRRRR- LEIKRLEHHHHHH | 92 |
| SEQ ID NO 2-GGGGSGGGGSGGGGS -hBD3-3 | MAQVKLQESGPELVRPGTSVKVSCKASGYAFTNYLIEWIKQRPGQGLEWIGVIHPGNGGTNYNENFKGKATLTADKSSSTAYMQLSSLTSDDSAVYFCASGNDGSYWGQGTTVTVSSGGGGSGGGGSGGGGSDIELTQSPSSLTVTAGEKVTMSCKSSQSLLNSGDQKIYLTWYQQKPGQPPKLLIYWASTRESGVPDRFTGSVSGTDFTLTISSVQAEDLAVYYCQNDYNYPYTFGGGTK - GGGGSGGGGSGGGGS - GKCSTRGRKCCRRKK - LEIKRLEHHHHHH | 93 |

pcDNA3.1-TOPO or pcDNA3.4-TOPO was digested with EcoR I and BamH I. The 900-960 bp KRAS mutant scFv gene fragment was recovered by an agarose electro-elution method. To insert the gene fragment into pcDNA3.1-TOPO and pcDNA3.4-TOPO vectors, the gene was amplified by PCR, and at the same time, BamH I and EcoR I restriction enzyme sites were synthesized. Each digested vector and insert were mixed together in a ratio of 4 μl:4 μl, and ligated together using T4 DNA ligase in a ligation buffer containing 500 mM Tris-HCl, 100 mM $MgCl_2$, 200 mM DTT and 10 mM ATP at 4° C. for 16 to 18 hours.

The present inventors transformed the prepared vector into the Chinese hamster ovary cell line Expi-CHO-S and the human embryonic kidney cell line Expi-293F. The Chinese hamster ovary cell line ExpiCHO-S was obtained from Thermo Fisher Scientific (USA) and cultured in ExpiCHO Expression medium (GIBCO, USA).

Next, the ExpiCHO-S cell line ($3\times10^8$ cells) was added to a 50 mL culture medium in a 250 mL disposable Erlenmeyer flask. 160 μL of ExpiFectamine CHO reagent (Gibco, Cat #A20130) diluted in 1.84 mL of Opti-MEM was added to 2 mL of Opti-MEM containing 50 μg of the plasmid and then incubated at room temperature for 5 minutes. Next, the dilution was evenly added dropwise to the prepared Chinese hamster ovary cells, and then incubated in a 8% $CO_2$ incubator at 37° C. for 18 hours, and then 300 μL of ExpiCHO enhancer and 12 mL of ExpiCHO Feed were added thereto and incubated for 5 days.

The human embryonic kidney cell line Expi-293F was obtained from Thermo Fisher Scientific (USA) and cultured in Expi293 Expression medium (GIBCO, USA). Next, the Expi-293F cell line ($1.50\times10^7$ cells) was added to 50 mL of culture medium in a 250 mL disposable Erlenmeyer flask. 160 μL of ExpiFectamine 293 Reagent (Gibco, Cat #A14525) (Gibco, Cat #A14525) diluted in 2.8 mL of Opti-MEM was added to 3 mL of Opti-MEM containing 50 μg of the plasmid and then stationary incubated at room temperature for 20 minutes. Next, the dilution was evenly added dropwise to the prepared human embryonic kidney cells, and then incubated in an 8% $CO_2$ incubator at 37° C. for 18 hours, and then 300 μL of ExpiFectamine 293 transfection enhancer 1 and 3 mL of ExpiFectamine 293 transfection enhancer 2 were added thereto and incubated for 3 days.

Six days after transduction, the culture medium was collected, sterilized and then purified using FPLC. After separation and purification was performed using a nickel chromatography column (HisTrap™ excel, GE Healthcare), the nickel column was equilibrated with a buffer [20 mM sodium phosphate, 0.5M NaCl, pH7.4], and then medium was applied to the column. After washing using the above buffer containing 25 mM imidazole, the protein was separated by increasing the imidazole to 125 mM. The separated proteins were stored after removing the imidazole by desalting.

Figure 3B:
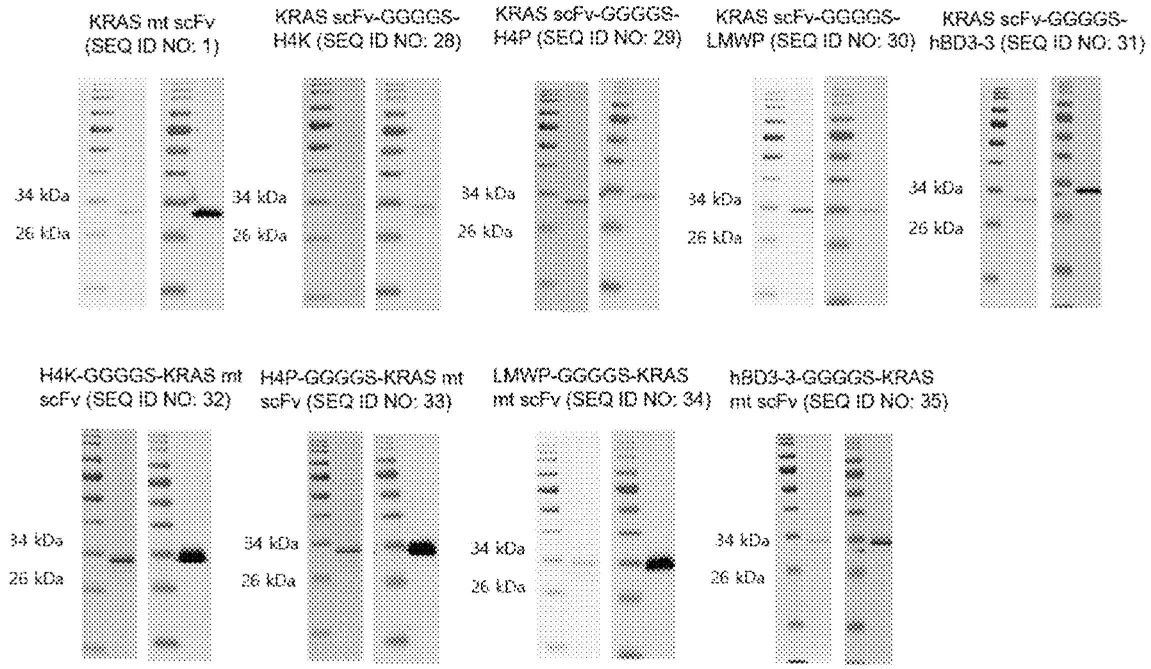
Figure 3C:
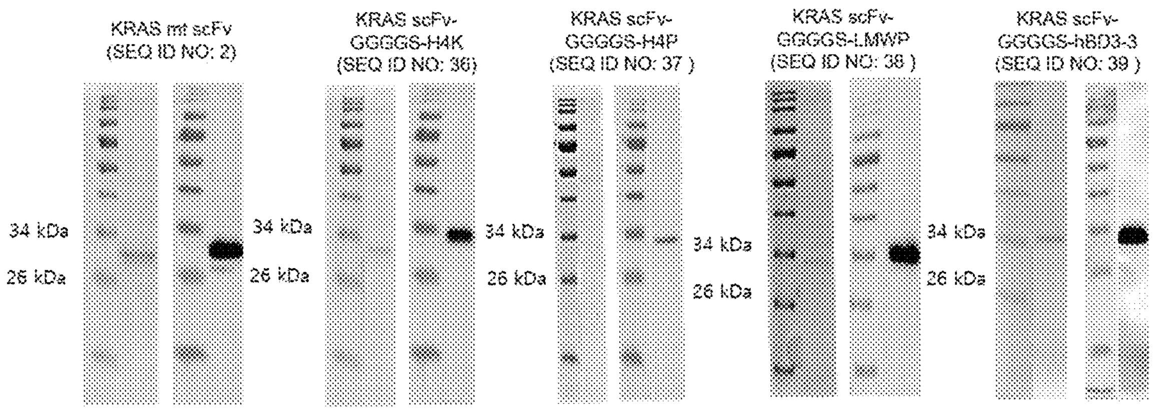

FIGS. 3*a*. 3b and 3c show the results of SDS-PAGE and Western blot analysis of the cancer cell-penetrating and KRAS mutant-targeting antibodies and scFvs expressed and purified in pcDNA3.4-TOPO (FIG. 3*b*) and pcDNA3.1-TOPO (FIG. 3*c*).

Example 2: Production of Cancer Cell-Penetrating Peptide and Anti-KRAS Mutant Single-Chain Variable Fragment (scFv) by Chemical Conjugation

Example 2-1: Synthesis of Cell-Penetrating Peptide

Table 6 below shows the amino acid sequences of the cancer cell-penetrating peptide and liker used in the chemical conjugation method.

TABLE 6

| Linker type | Cancer cell-penetrating peptide (CCPP) | Sequence and SEQ ID NO of linker and cancer cell-penetrating peptide |
|---|---|---|
| CGGGGG | CCPP1 (H4K) | 60: CGGGGG-HRRCNKNNKKR |
| | CCPP2 (H4P) | 61: CGGGGG-HRRCNPNNKKR |
| | CCPP3 (LMWP) | 62: CGGGGG-VSRRRRRRGGRRRR |
| | CCPP4 (hBD3-3) | 63: CGGGGG-GKCSTRGRKCCRRKK |
| CGGGGGSSGGGGG | CCPP1 (H4K) | 64: CGGGGGSSGGGGG-RKKNNKNCRRH |
| | CCPP2 (H4P) | 65: CGGGGGSSGGGGG-RKKNNPNCRRH |
| | CCPP3 (LMWP) | 66: CGGGGGSSGGGGG-RRRRGGRRRRRRSV |
| | CCPP4 (hBD3-3) | 67: CGGGGGSSGGGGG-GKCSTRGRKCCRRKK |

Amino acids and reagents for synthesis were purchased from GL Biochem and Sigma-Aldrich. Peptides were synthesized from the C-terminus by an F-moc solid-state chemical synthesis method using a reaction vessel. That is, peptides were synthesized using Rink amide MBHA resin (0.678 mmol/g, 100 to 200 mesh) to which Fmoc-(9-fluorenylmethoxycarbonyl) as a blocking group was bound. After placing 1 g of Rink amide MBHA resin in the reaction vessel, the resin was swollen with DMF, and then 20% piperidine/DMF solution was used to remove the Fmoc-group. According to the sequence from the C-terminus, 0.5M amino acid solution (solvent: dimethylformamide, DMF), 1.0M DIPEA (solvent: dimethylformamide & n-methylpyrrolidone, DMF&NMP), 0.5M HBTU (solvent: dimethylformamide, DMF) were added in amounts of 5, 10 and 5 equivalents, respectively, and reacted for 1 to 2 hours under a nitrogen atmosphere. After each of the deprotection and coupling steps, washing three times with DMF and methanol was performed. Even after coupling the last amino acid, deprotection was performed to remove the Fmoc-group.

Confirmation of the synthesis was performed using the ninhydrin test method. The resin confirmed by the test to be completely synthesized was vacuum-dried, and a trifluoroacetic acid (TFA) cleavage cocktail was added thereto in an amount of 10 ml per g of the resin, followed by shaking for 3 hours. Then, the cocktail containing the peptide dissolved therein was separated from the resin by filtration. The peptide was crystallized into a solid state by placing the filtered solution in cold ether or adding an excess of cold ether directly to the TFA cocktail solution containing the peptide dissolved therein, and the peptide was collected by centrifugation. At this time, the TFA cocktail was completely removed through washing several times with ether and centrifugation. The peptide thus obtained was vacuum-dried.

The synthesized peptide was separated and purified by high-performance liquid chromatography (Shimadzu, Japan). Analysis was performed using a $C_{18}$ column (diameter: 4.6 mm) by running 0.1% TFA/$H_2O$ and 0.1% TFA/acetonitrile at a flow rate of 1 ml/min with a gradient from 5 to 45%, and the wavelength of the UV detector was set to 220 nm. Purification was performed using a column (diameter: 50 mm) at a flow rate of 50 ml/min under the same solvent and detection wavelength conditions as above. The molecular weight of the purified peptide was analyzed through mass spectrometry.

Example 2-2: Chemical Conjugation of Cancer Cell-Penetrating Peptide to Linker Moiety of KRAS Mutant-Targeting scFv and Purification 1.02 mg of KRAS scFv of SEQ ID NO: 1 was dissolved in 1 mL of PBS buffer (pH 8.3). 2.12 mg of SPDP (succinimidyl 3-(2-pyridyldithio)propionate, ThermoFisher, 21857) was dissolved in 120 μL of DMSO (dimethyl sulfoxide). 40 μL of the SPDP solution was added to the KRAS scFv solution and allowed to react for 1 hour under a light-shielded condition, and this addition and reaction process was repeated three times. Alternatively, 2 mg sulfo-SMCC (succinimidyl 4-[N-maleimidomethyl]cyclohexane-1-carboxylate, ThermoFisher, 22322) was dissolved in PBS. 40 μL of the sulfo-SMCC solution was added to the KRAS scFv solution and allowed to react for 1 hour under a light-shielded condition, and this addition and reaction process was repeated three times.

After completion of the reaction, desalting was performed using a PD-10 desalting column (GE Healthcare), and 3.5 mL of pyridyldithiol activated KRAS scFv was obtained. To the pyridyldithiol activated KRAS scFv, a solution of each of 2.5 mg Cys-G5-H4K (SEQ ID NO: 60), Cys-G5-H4P (SEQ ID NO: 61), Cys-G5-LMWP (SEQ ID NO: 62), Cys-G5-hBD3-3 (SEQ ID NO: 63), Cys-G5S2G5-H4K (SEQ ID NO: 64), Cys-G5S2G5-H4P (SEQ ID NO: 65), Cys-G5S2G5-LMWP (SEQ ID NO: 66), and Cys-G5S2G5-hBD3-3 (SEQ ID NO: 67) in 300 μL of triple distilled water was added, and each mixture was adjusted to pH 8.3 using 1M tris buffer (pH=9). Each mixture was allowed to react at 4° C. overnight under a light-shielded condition. The KRAS mutant scFv having each cancer cell-penetrating peptide bound thereto was purified by FPLC (Akta Pure, GE Healthcare) using a heparin column (HiTrap, GE Healthcare).

1.02 mg of scFv of SEQ ID NO: 1 was dissolved in 1 mL of PBS buffer (pH 7.4). 2.98 mg of Sulfo-SMCC (sulfosuccinimidyl 4-(N-maleimidomethyl)cyclohexane-1-carbocylate, ThermoFisher, catalog 22322) was dissolved in 300 μL of triple distilled water. 100 μL of the Sulfo-SMCC solution was added to the scFv solution and allowed to react for 30 minutes under a light-shielded condition, and this addition and reaction process was repeated three times. After completion of the reaction, desalting was performed using a PD-10 desalting column (GE Healthcare, 17-0851-01), and 3.5 mL of maleimide activated scFv was obtained. To the maleimide activated scFv, a solution of each of 2.5 mg Cys-G5-H4K (SEQ ID NO: 60), Cys-G5-H4P (SEQ ID NO: 61), Cys-G5-LMWP (SEQ ID NO: 62), Cys-G5-hBD3-3 (SEQ ID NO: 63), Cys-G5S2G5-H4K (SEQ ID NO: 64), Cys-G5S2G5-H4P (SEQ ID NO: 65), Cys-G5S2G5-LMWP (SEQ ID NO: 66), and Cys-G5S2G5-hBD3-3 (SEQ ID NO: 67) in 300 μL of PBS buffer (pH 8.3) was added, and each mixture was adjusted to pH 7.0 to 7.5. Each mixture was allowed to react at 4° C. overnight under a light-shielded condition. The scFv having each cancer cell-penetrating peptide bound thereto was purified by FPLC (Akta Pure, GE healthcare) using a heparin column (HiTrap, GE Healthcare).

Figure 4:
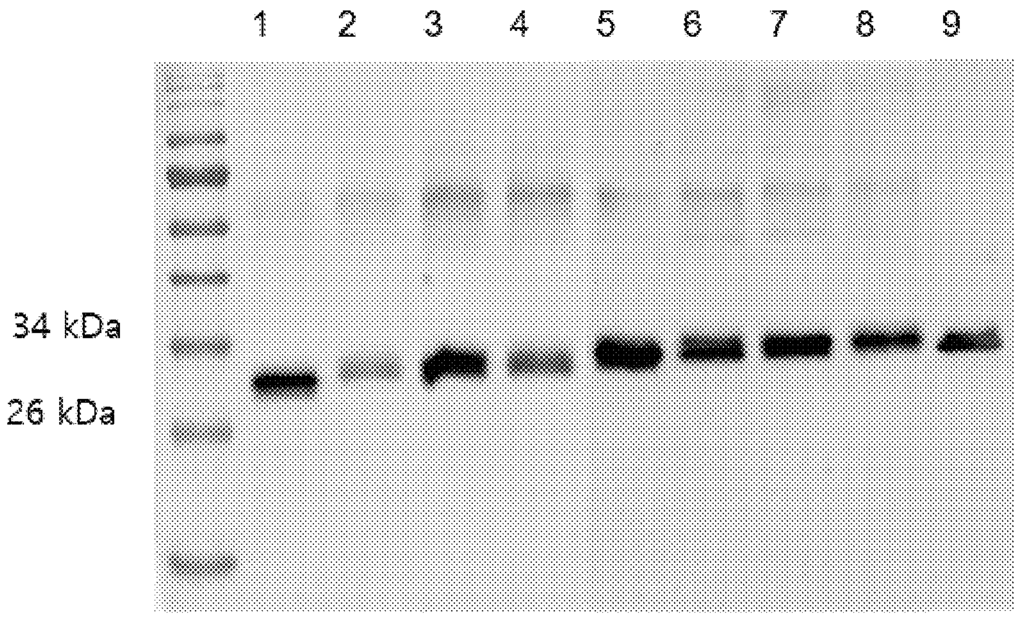
FIG. 4 shows the results of SDS-PAGE and Western blot analysis of cancer cell-penetrating KRAS mutant antibodies and scFvs produced by a chemical conjugation method.

FIG. 4 shows the results of SDS-PAGE and Western blot analysis of the cancer cell-penetrating and KRAS mutant-targeting antibodies or single-chain variable fragments produced by the chemical conjugation method.

The molecular weight of the KRAS mutant scFv of SEQ ID NO: 1 was about 30 kDa, and the molecular weight of the KRAS mutant scFv having the cancer cell-penetrating peptide bound thereto was measured to be about 32 kDa. In addition, the molecular weight of the band bound to the KRAS antibody in the Western blot was measured to be 30 kDa for the scFv of SEQ ID NO: 1, and was measured to be about 32 kDa for the scFv having the cancer cell-penetrating peptide bound thereto, suggesting that the peptide was bound to the scFv.

Example 2-3: Chemical Conjugation of Cancer Cell-Penetrating Peptide to C-Terminus of KRAS Mutant scFv and Purification The KRAS mutant scFv of SEQ ID NO: 3 was allowed to react with 20 molar equivalents of tris(2-carboxyethyl) phosphine (TCEP) at room temperature for 3 hours to form a free thiol group. 100 molar equivalents of 5,50-dithiobis-(2-nitrobenzoic acid) (DTNB) was added to the KRAS mutant scFv solution and reacted for 1 hour at room temperature so as to bind to the free thiol group. Excess DTNB not bound to the KRAS mutant scFv was removed by FPLC (Akta Pure, GE healthcare) using a heparin column (HiTrap, GE Healthcare). Thereafter, the KRAS mutant scFv-DTNB conjugate was allowed to react with 10 molar equivalents of each cancer cell-penetrating peptide (SEQ ID NOs: 60 to 67) at room temperature for 1 hour. The scFv having each cancer cell-penetrating peptide bound thereto was purified by FPLC (Akta Pure, GE healthcare) using a heparin column (HiTrap, GE Healthcare).

Table 7 below shows the amino acid sequences of the fusion proteins wherein the cancer cell-penetrating peptide is linked to the KRAS mutant scFv and which were produced by the chemical conjugation method.

TABLE 7

| SEQ ID NO of conjugate comprising scFv of SEQ ID NO: 1 and cancer cell-penetrating peptide |
|---|
| 68:<br>MAWVWTLLFLMAAAQSIQAEWIKQRPGQGLEWIGV<br>IHPGNGGTNYNENFKGKATLTADKSSSTAYMQLSS<br>LTSDDSAVYFCASGNDGSYWGQGTTVTVSSGGGGS<br>GK-CGGGGG-HRRCNKNNKKR-<br>GGSGGGGSGGGGSDIELTQSPSSLTVTAGEKVTMS<br>CKSSQSLLNSGDQKIYLTWYQQKPGQPPKLLIYWA<br>STRESGVPDRFTGSVSGTDFTLTISSVQAEDLAVY<br>YCQNDYNYPYTFGGGTKLEIKRGSENLYFQGGSGK<br>PIPNPLLGLDSTGGSGGSHHHHHH<br>CGGGGG- HRRCNKNNKKR is linked to the amine group of the linker moiety of scFv.<br>Lysine of the linker moiety in SEQ ID NO: 1<br>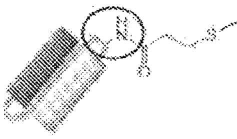<br>CGGGGG——HRRCNKNNKKR |
| 69:<br>MAWVWTLLFLMAAAQSIQAEWIKQRPGQGLEWIGV<br>IHPGNGGTNYNENFKGKATLTADKSSSTAYMQLSS<br>LTSDDSAVYFCASGNDGSYWGQGTTVTVSSGGGGS<br>GK-CGGGGG-HRRCNKNNKKR-<br>GGSGGGGSGGGGSDIELTQSPSSLTVTAGEKVTMS<br>CKSSQSLLNSGDQKIYLTWYQQKPGQPPKLLIYWA<br>STRESGVPDRFTGSVSGTDFTLTISSVQAEDLAVY<br>YCQNDYNYPYTFGGGTKLEIKRGSENLYFQGGSGK<br>PIPNPLLGLDSTGGSGGSHHHHHH<br>CGGGGG- HRRCNKNNKKR is linked to the amine group of the linker moiety of scFv.<br>Lysine of the linker moiety in SEQ ID NO: 1 |

TABLE 7-continued

SEQ ID NO of conjugate comprising scFv of SEQ ID NO: 1 and cancer cell-penetrating peptide

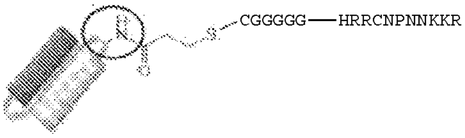

70:
MAWVWTLLFLMAAAQSIQAEWIKQRPGQGLEWIGVIHPGNGGTNYNENFKGKATLTADKSSSTAYMQLSSLTSDDSAVYFCASGNDGSYWGQGTTVTVSSGGGGSGK-CGGGGG-VSRRRRRRGGRRRR-GGSGGGGSGGGGSDIELTQSPSSLTVTAGEKVTMSCKSSQSLLNSGDQKIYLTWYQQKPGQPPKLLIYWASTRESGVPDRFTGSVSGTDFTLTISSVQAEDLAVYYCONDYNYPYTFGGGTKLEIKRGSENLYFQGGSGKPIPNPLLGLDSTGGSGGSHHHHHH
CGGGGG- VSRRRRRRGGRRRR is linked to the amine group of lysine in the linker moiety of scFv.
Lysine of the linker moiety in SEQ ID NO: 1

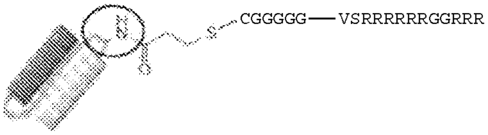

71:
MAWVWTLLFLMAAAQSIQAEWIKQRPGQGLEWIGVIHPGNGGTNYNENFKGKATLTADKSSSTAYMQLSSLTSDDSAVYFCASGNDGSYWGQGTTVTVSSGGGGSGK-CGGGGG-GKCSTRGRKCCRRKK-GGSGGGGSGGGGSDIELTQSPSSLTVTAGEKVTMSCKSSQSLLNSGDQKIYLTWYQQKPGQPPKLLIYWASTRESGVPDRFTGSVSGTDFTLTISSVQAEDLAVYYCONDYNYPYTFGGGTKLEIKRGSENLYFQGGSGKPIPNPLLGLDSTGGSGGSHHHHHH
CGGGGG- GKCSTRGRKCCRRKK is linked to the amine group of lysine in the linker moiety of scFv.
Lysine of the linker moiety in SEQ ID NO: 1

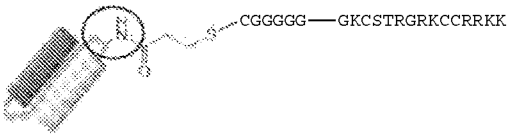

72:
MAWVWTLLFLMAAAQSIQAEWIKORPGQGLEWIGVIHPGNGGTNYNENFKGKATLTADKSSSTAYMQLSSLTSDDSAVYFCASGNDGSYWGQGTTVTVSSGGGGSGK-CGGGGGSSGGGG-HRRCNKNNKKR-GGSGGGGSGGGGSDIELTQSPSSLTVTAGEKVTMSCKSSQSLLNSGDQKIYLTWYQQKPGQPPKLLIYWASTRESGVPDRFTGSVSGTDFTLTISSVQAEDLAVYYCONDYNYPYTFGGGTKLEIKRGSENLYFQGGSGKPIPNPLLGLDSTGGSGGSHHHHHH
CGGGGGSSGGGG- HRRCNKNNKKR is linked to the amine group of lysine in the linker moiety of scFv.
Lysine of the linker moiety in SEQ ID NO: 1

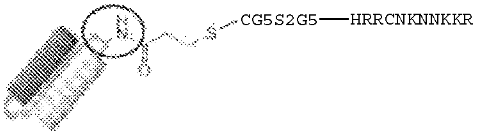

73:
MAWVWTLLFLMAAAQSIQAEWIKQRPGQGLEWIGVIHPGNGGTNYNENFKGKATLTADKSSSTAYMQLSSLTSDDSAVYFCASGNDGSYWGQGTTVTVSSGGGGSGK-CGGGGGSSGGGGG-RKKNNPNCRRH-GGSGGGGSGGGGSDIELTQSPSSLTVTAGEKVTMSCKSSQSLLNSGDQKIYLTWYQQKPGQPPKLLIYWASTRESGVPDRFTGSVSGTDFTLTISSVQAEDLAVYYCONDYNYPYTFGGGTKLEIKRGSENLYFQGGSGKPIPNPLLGLDSTGGSGGSHHHHHH
CGGGGGSSGGGGG- RKKNNPNCRRH is linked to the amine group of lysine in the linker moiety of scFv.
Lysine of the linker moiety in SEQ ID NO: 1

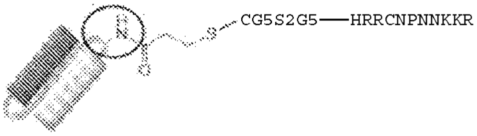

74:
MAWVWTLLFLMAAAQSIQAEWIKQRPGQGLEWIGVIHPGNGGTNYNENFKGKATLTADKSSSTAYMQLSSLTSDDSAVYFCASGNDGSYWGQGTTVTVSSGGGGSGK-CGGGGGSSGGGGG-RRRRGGRRRRRRSV-GGSGGGGSGGGGSDIELTQSPSSLTVTAGEKVTMSCKSSQSLLNSGDQKIYLTWYQQKPGQPPKLLIYWASTRESGVPDRFTGSVSGTDFTLTISSVQAEDLAVYYCQNDYNYPYTFGGGTKLEIKRGSENLYFQGGSGKPIPNPLLGLDSTGGSGGSHHHHHH
CGGGGGSSGGGGG-RRRRGGRRRRRRSV is linked to the amine group of lysine in the linker moiety of scFv.
Lysine of the linker moiety in SEQ ID NO: 1

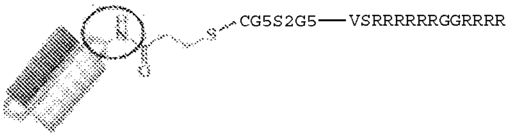

75:
MAWVWTLLFLMAAAQSIQAEWIKQRPGQGLEWIGVIHPGNGGTNYNENFKGKATLTADKSSSTAYMQLSSLTSDDSAVYFCASGNDGSYWGQGTTVTVSSGGGGSGK-CGGGGGSSGGGGG-GKCSTRGRKCCRRKK-GGSGGGGSGGGGSDIELTQSPSSLTVTAGEKVTMSCKSSQSLLNSGDQKIYLTWYQQKPGQPPKLLIYWASTRESGVPDRFTGSVSGTDFTLTISSVQAEDLAVYYCONDYNYPYTFGGGTKLEIKRGSENLYFQGGSGKPIPNPLLGLDSTGGSGGSHHHHHH
CGGGGGSSGGGGG- GKCSTRGRKCCRRKK is linked to the amine group of lysine in the linker moiety of scFv.
Lysine of the linker moiety in SEQ ID NO: 1

TABLE 7-continued

| SEQ ID NO of conjugate comprising scFv of SEQ ID NO: 1 and cancer cell-penetrating peptide |
|---|
| 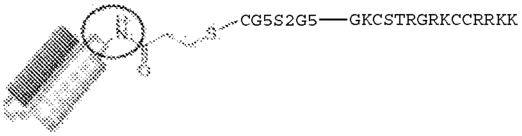<br> |
| 76: MAWVWTLLFLMAAAQSIQAEWIKQRPGQGLEWIGVIHPGNGGTNYNENFKGKATLTADKSSSTAYMQLSSLTSDDSAVYFCASGNDGSYWGQGTTVTVSSGGGGSGKGGSGGGGSGGGGSDIELTQSPSSLTVTAGEKVTMSCKSSQSLLNSGDQKIYLTWYQQKPGQPPKLLIYWASTRESGVPDRFTGSVSGTDFTLTISSVQAEDLAVYYCQNDYNYPYTFGGGTKC-CGGGGG-HRRCNPNNKKR-LEIKRGSENLYFQGGSGKPIPNPLLGLDSTGGSGGSHHHHHH<br>CGGGGG- HRRCNKNNKKR is linked to the SH group of cysteine at the C-terminus. |
| 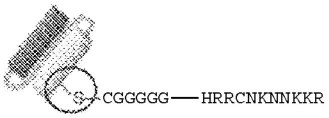<br><br>Cysteine at the C-terminus of SEQ ID NO: 3 |
| 77: MAWVWTLLFLMAAAQSIQAEWIKQRPGQGLEWIGVIHPGNGGTNYNENFKGKATLTADKSSSTAYMQLSSLTSDDSAVYFCASGNDGSYWGQGTTVTVSSGGGGSGKGGSGGGGSGGGGSDIELTQSPSSLTVTAGEKVTMSCKSSQSLLNSGDQKIYLTWYQQKPGQPPKLLIYWASTRESGVPDRFTGSVSGTDFTLTISSVQAEDLAVYYCQNDYNYPYTFGGGTKC-CGGGGG-HRRCNPNNKKR-LEIKRGSENLYFQGGSGKPIPNPLLGLDSTGGSGGSHHHHHH<br>CGGGGG- HRRCNPNNKKR is linked to the SH group of cysteine at the C-terminus. |
| 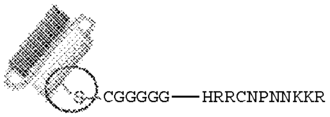<br><br>Cysteine at the C-terminus of SEQ ID NO: 3 |
| 78: MAWVWTLLFLMAAAQSIQAEWIKQRPGQGLEWIGVIHPGNGGTNYNENFKGKATLTADKSSSTAYMQLSSLTSDDSAVYFCASGNDGSYWGQGTTVTVSSGGGGSGKGGSGGGGSGGGGSDIELTQSPSSLTVTAGEKVTMSCKSSQSLLNSGDQKIYLTWYQQKPGQPPKLLIYWASTRESGVPDRFTGSVSGTDFTLTISSVQAEDLAVYYCQNDYNYPYTFGGGTKC-CGGGGG-VSRRRRRRGGRRRR-LEIKRGSENLYFQGGSGKPIPNPLLGLDSTGGSGGSHHHHHH<br>CGGGGG- VSRRRRRRGGRRRR is linked to the SH group of cysteine at the C-terminus. |

TABLE 7-continued

| SEQ ID NO of conjugate comprising scFv of SEQ ID NO: 1 and cancer cell-penetrating peptide |
|---|
| 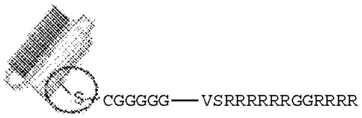<br><br>Cysteine at the C-terminus of SEQ ID NO: 3 |
| 79: MAWVWTLLFLMAAAQSIQAEWIKQRPGQGLEWIGVIHPGNGGTNYNENFKGKATLTADKSSSTAYMQLSSLTSDDSAVYFCASGNDGSYWGQGTTVTVSSGGGGSGKGGSGGGGSGGGGSDIELTQSPSSLTVTAGEKVTMSCKSSQSLLNSGDQKIYLTWYQQKPGQPPKLLIYWASTRESGVPDRFTGSVSGTDFTLTISSVQAEDLAVYYCQNDYNYPYTFGGGTKC-CGGGGGGKCSTRGRKCCRRKK-LEIKRGSENLYFQGGSGKPIPNPLLGLDSTGGSGGSHHHHHH<br>CGGGGG- GKCSTRGRKCCRRKK is linked to the SH group of cysteine at the C-terminus. |
| 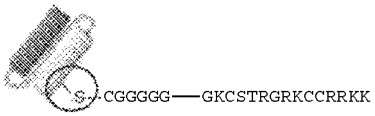<br><br>Cysteine at the C-terminus of SEQ ID NO: 3 |
| 80: MAWVWTLLFLMAAAQSIQAEWIKQRPGQGLEWIGVIHPGNGGTNYNENFKGKATLTADKSSSTAYMQLSSLTSDDSAVYFCASGNDGSYWGQGTTVTVSSGGGGSGKGGSGGGGSGGGGSDIELTQSPSSLTVTAGEKVTMSCKSSQSLLNSGDQKIYLTWYQQKPGQPPKLLIYWASTRESGVPDRFTGSVSGTDFTLTISSVQAEDLAVYYCQNDYNYPYTFGGGTKC-CGGGGGSSGGGG-HRRCNKNNKKR-LEIKRGSENLYFQGGSGKPIPNPLLGLDSTGGSGGSHHHHHH<br>CGGGGGSSGGGG- HRRCNKNNKKR is linked to the SH group of cysteine at the C-terminus . |
| 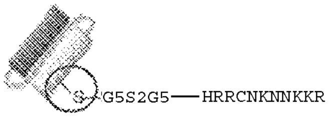<br><br>Cysteine at the C-terminus of SEQ ID NO: 3 |
| 81: MAWVWTLLFLMAAAQSIQAEWIKQRPGQGLEWIGVIHPGNGGTNYNENFKGKATLTADKSSSTAYMQLSSLTSDDSAVYFCASGNDGSYWGQGTTVTVSSGGGGSGKGGSGGGGSGGGGSDIELTQSPSSLTVTAGEKVTMSCKSSQSLLNSGDQKIYLTWYQQKPGQPPKLLIYWASTRESGVPDRFTGSVSGTDFTLTISSVQAEDLAVYYCQNDYNYPYTFGGGTKC-CGGGGGSSGGGGG-RKKNNPNCRRH-LEIKRGSENLYFQGGSGKPIPNPLLGLDSTGGSGGSHHHHHH<br>CGGGGGSSGGGGG- RKKNNPNCRRH is linked to the SH group of cysteine at the C-terminus. |

TABLE 7-continued

| SEQ ID NO of conjugate comprising scFv of SEQ ID NO: 1 and cancer cell-penetrating peptide |
|---|
| 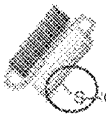<br>G5S2G5——HRRCNPNNKKR<br><br>Cysteine at the C-terminus of SEQ ID NO: 3 |
| 82:<br>MAWVWTLLFLMAAAQSIQAEWIKQRPGQGLEWIGV<br>IHPGNGGTNYNENFKGKATLTADKSSSTAYMQLSS<br>LTSDDSAVYFCASGNDGSYWGQGTTVTVSSGGGGS<br>GKGGSGGGGSGGGGSDIELTQSPSSLTVTAGEKVT<br>MSCKSSQSLLNSGDQKIYLTWYQQKPGQPPKLLIY<br>WASTRESGVPDRFTGSVSGTDFTLTISSVQAEDLA<br>VYYCQNDYNYPYTFGGGTKC-CGGGGGSSGGGGG-<br>VSRRRRGGRRRRRRSV-<br>LEIKRGSENLYFQGGSGKPIPNPLLGLDSTGGSGG<br>SHHHHHH<br>CGGGGGSSGGGGG-VSRRRRGGRRRRRRSV is linked to the SH group of cysteine at the C-terminus. |
| 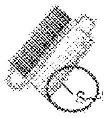<br>G5S2G5——VSRRRRRRGGRRRR<br><br>Cysteine at the C-terminus of SEQ ID NO: 3 |
| 83:<br>MAWVWTLLFLMAAAQSIQAEWIKQRPGQGLEWIGV<br>IHPGNGGTNYNENFKGKATLTADKSSSTAYMQLSS<br>LTSDDSAVYFCASGNDGSYWGQGTTVTVSSGGGGS<br>GKGGSGGGGSGGGGSDIELTQSPSSLTVTAGEKVT<br>MSCKSSQSLLNSGDQKIYLTWYQQKPGQPPKLLIY<br>WASTRESGVPDRFTGSVSGTDFTLTISSVQAEDLA<br>VYYCQNDYNYPYTFGGGTKC-CGGGGGSSGGGGG-<br>GKCSTRGRKCCRRKK-<br>LEIKRGSENLYFQGGSGKPIPNPLLGLDSTGGSGG<br>SHHHHHH<br>CGGGGGSSGGGGG-GKCSTRGRKCCRRKK is linked to the SH group of cysteine at the C-terminus. |
| 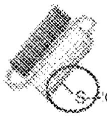<br>G5S2G5——GKCSTRGRKCCRRKK<br><br>CG5SZGS-GKCSTRGRKCCRRKK<br>Cysteine at the C-terminus of SEQ ID NO: 3 |

Example 3: Evaluation of Inhibitory Activity Against Cancer Cells with Different KRAS Mutant Expression Levels In order to evaluate the cancer cell-specific growth inhibitory activities of the cancer cell-penetrating and KRAS mutant-targeting antibody and scFv according to the present invention, H358 cells (cancer cells expressing KRAS mutant) or human dermal fibroblasts (normal cells) were dispensed into a 96-well plate at a density of $5\times10^3$ cells/well, and then cultured in RPMI medium 1640 (Gibco) for 24 hours. The cells were treated with each scFv (SEQ ID NOs: 1 and 28 to 35) at a concentration of 5 μM. Cytotoxicity was measured using CCK-8 (Cell Counting Kit-8, CK04, Dojindo Lab.). 48 hours after treatment with each scFv, the medium was removed, and 100 μl of CCK-8 solution was dispensed to fresh RPMI medium 1640. After 1 hour and 30 minutes, the absorbance at 450 nm was measured.

Figure 5A:
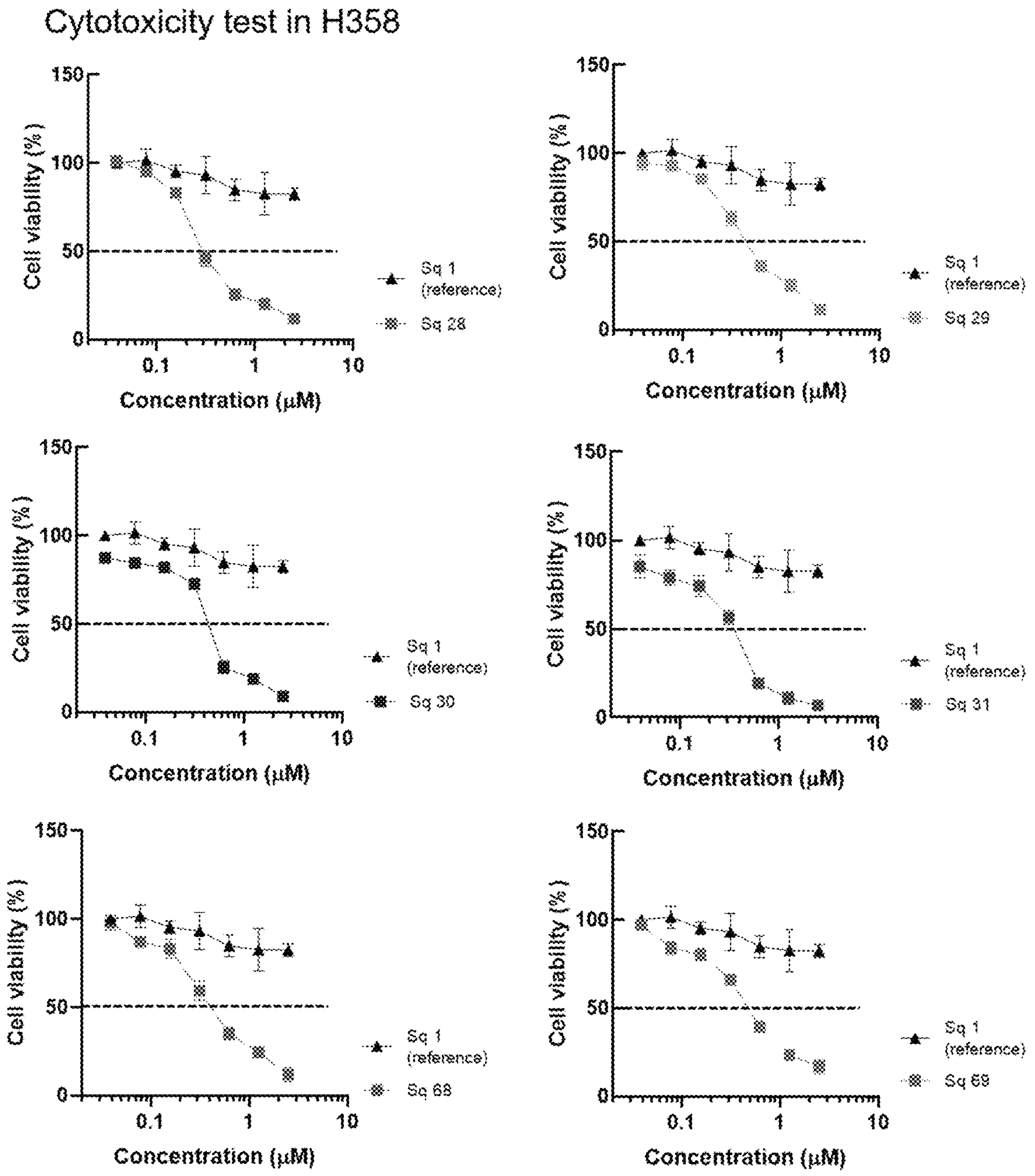
FIGS. 5*a* and 5*b* show the results of evaluating the cancer cell-specific killing effects of cancer cell-penetrating KRAS mutant antibodies and scFvs.
Figure 5B:
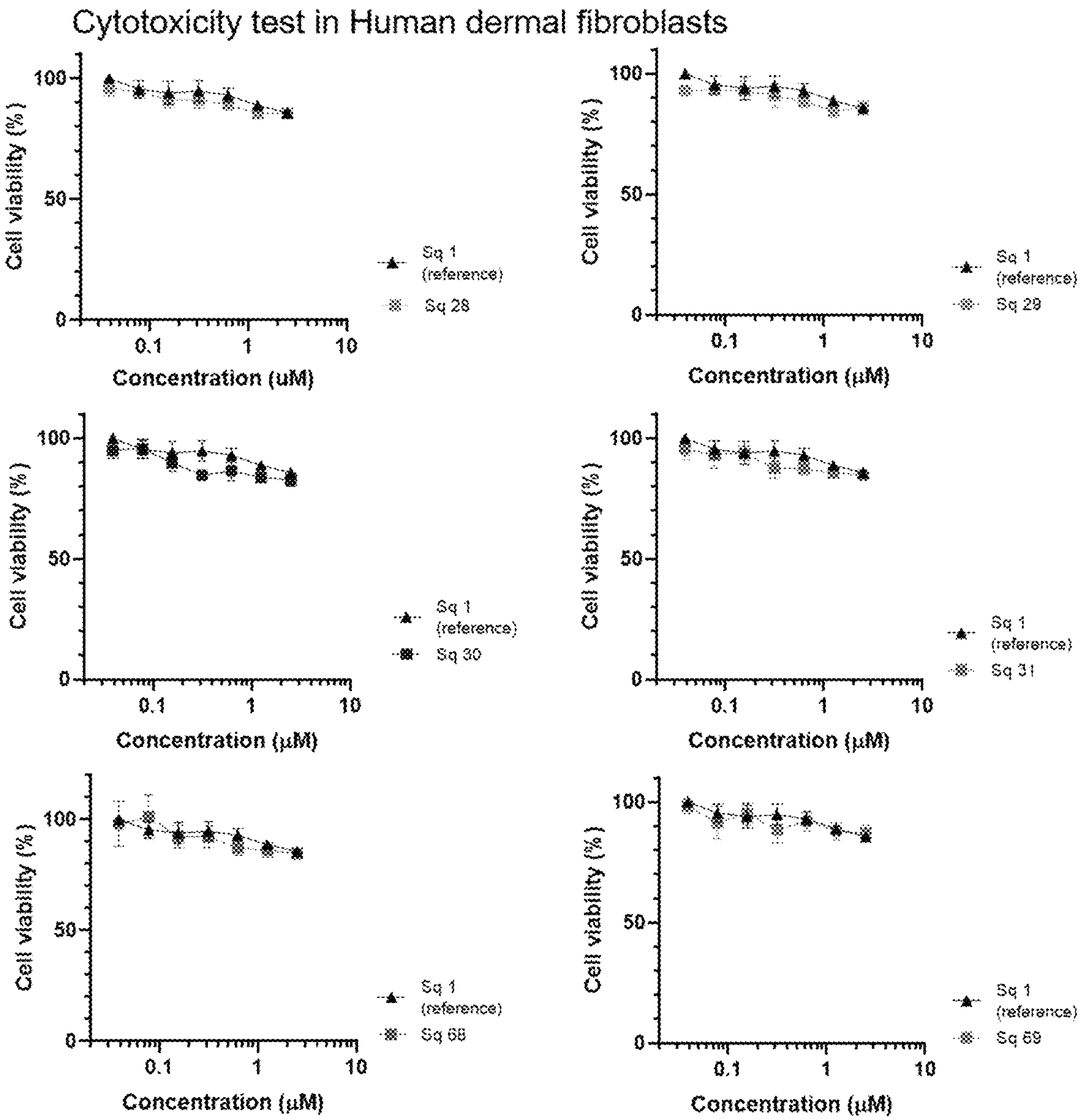

As a result, as shown in FIGS. 5*a* and 5*b*, it was confirmed that SEQ ID NOs: 28 to 31, 68 and 69 showed an $IC_{50}$ value of 100 to 500 nM (concentration at which 50% of cells are killed) in the H358 cells, and for SEQ ID NO: 1, the $IC_{50}$ value could not be measured even at a concentration of 5 μM. This is believed to be because SEQ ID NO: 1 did not show the cancer cell killing effect by being unable to penetrate the cancer cells, but SEQ ID NOs: 28 to 31, 68 and 69 exhibited cytotoxicity by being able to penetrate the cancer cells. For the human dermal fibroblasts that are normal cells, SEQ ID NOs: 28 to 31, 68 and 69 showed a cell viability of 80% or higher at all the concentrations. This means that the cancer cell-penetrating and KRAS mutant-targeting scFv conjugates have cancer cell-specific cytotoxicity.

Example 4: Evaluation of Active KRAS (Mutant KRAS) Expression Inhibitory Activities of Cancer Cell-Penetrating and KRAS Mutant-Targeting Antibody and scFv $1.0\times10^6$ H358 cells (ATCC, CRL-5807) were seeded and cultured in RPMI medium 1640 (1×) (Gibco, 22400-089) for 24 hours, followed by starvation for 16 hours. The cells were treated with 50 ng/mL of EGF (epithelial growth factor, R&D Systems, 236-EG) for 10 minutes and treated with 1 μM of each variant. After 24 hours, the medium was removed, each well was washed with PBS, and the cells were harvested and centrifuged at 1,500 rpm for 3 minutes. 150 μL of 1× lysis buffer (1× Lysis/Binding/Wash buffer, 11524S) was added to and mixed with the cells and kept on ice for 5 minutes. The supernatant was separated by centrifugation at 16,000 rpm at 4° C. for 15 minutes. Protein concentration was measured by BCA assay (Thermo Scientific, 23227). Washing was performed with 400 μL of 1× lysis buffer, and centrifugation was performed twice at 6000×g for 15 seconds.

To separate the mutant KRAS, 80 μg of GST-Raf1-RBD was added using Active GTPase Kit (Cell Signaling, 11860S), and 500 μg of the protein was dispensed into the spin cup. After 1 hour of incubation at 4° C., centrifugation was performed at 6000×g for 15 seconds, and then the column was transferred into a fresh tube, and 400 μL of 1× lysis buffer was added thereto. After centrifugation at 6000×g for 15 seconds, the column was transferred into a fresh tube, and 50 μL of 2×SDS buffer (containing 200 μl of 5×SDS sample loading dye and 300 μl of water) was added thereto and reacted for 2 minutes. After centrifugation at 6000×g for 2 minutes, the resulting solution was held at 100° C. for 7 minutes. The protein (20 μl protein loading volume/lane) was separated by 11% SDS-PAGE electrophoresis and transferred to a nitrocellulose membrane. To measure ERK1/2, which is a signal downstream of KRAS, 30 μg of the protein was electrophoresed by 11% SDS-PAGE and transferred to a nitrocellulose membrane. The membrane was blocked with 5% skim milk in T-TBS for 1 hour and incubated with a primary antibody (diluted 1:1000 in T-TBS) overnight with inversion at 4° C. The membrane was washed with T-TBS 3 times for 10 minutes per washing, and incubated with a secondary antibody (diluted 1:3000 in T-TBS) for 1 hour with inversion at room temperature. The membrane was washed 3 times with T-TBS for 10 minutes per washing, incubated with ECL chemiluminescence substrate (Thermo, 34580), and visualized with an Amersham Imager 680 (GE). Information on the antibodies used is shown in Table 8 below.

TABLE 8

| No. | Antibody name | Manufacturer | Catalog No. |
|---|---|---|---|
| 1 | GST | Abcam | Ab19256 |
| 2 | Active KRAS | Santa Cruz | SC-30 |
| 3 | RAS(E4K9L) | Cell Signaling | 91054S |
| 4 | p-B-Raf(S445) | Cell Signaling | 2696S |
| 5 | p-MEK1/2(S221) | Cell Signaling | 2338S |
| 6 | p-Erk1/2 | Santa Cruz | SC-7383 |
| 7 | GAPDH | Cell Signaling | 2118S |
| 8 | Goat anti-Rabbit IgG | BETHYL | A120-101P |
| 9 | Goat anti-Mouse IgG | BETHYL | A90-116P |

In SEQ ID NOs: 20 to 23, the linker between the KRAS mutant-targeting antibody or scFv and the cell-penetrating peptide is GGGGS (SEQ ID NO: 94), and in SEQ ID NOs: 90 to 93, the linker is GGGGSGGGGSGGGGS (SEQ ID NO: 95).

Figure 6:
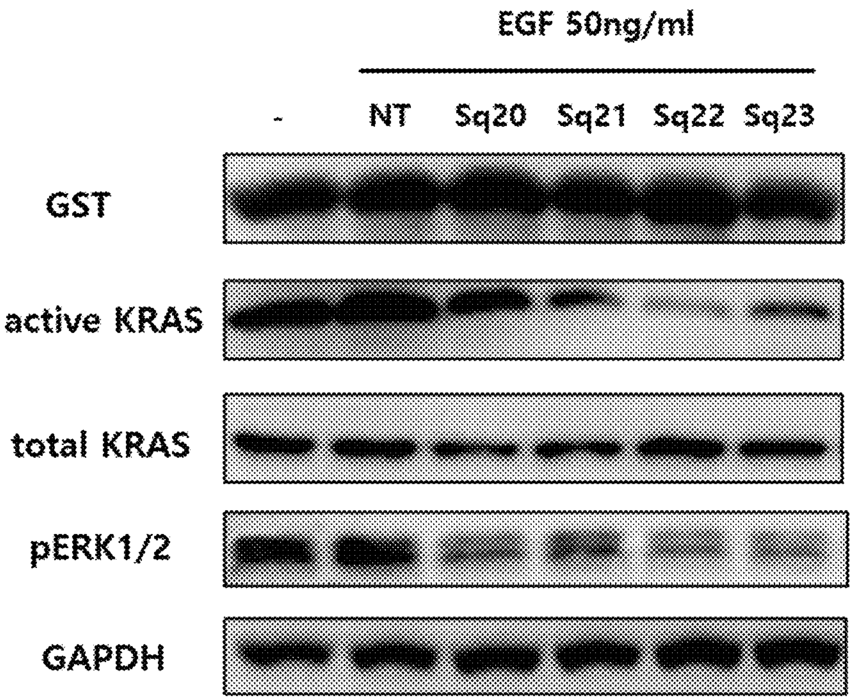
FIG. 6 shows the results of Western blot analysis performed to evaluate the active KRAS (mutant KRAS) expression inhibitory activities of SEQ ID NOs: 20 to 23, each linked by a GGGGS (SEQ ID NO: 94) linker.

As a result, as shown in FIG. 6, it was confirmed that SEQ ID NOs: 20 to 23 all decreased active KRAS compared to treatment with EGF alone. In addition, it could be seen that pERK1/2, which is a signal downstream of KRAS, was also reduced by SEQ ID NOs: 20 to 23.

Figure 7:
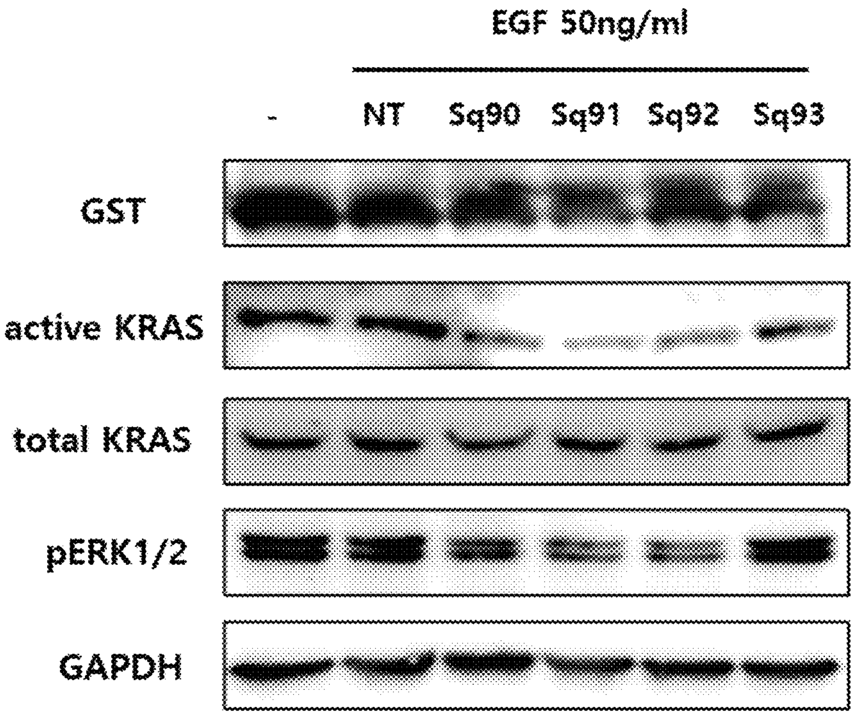
FIG. 7 shows the results of Western blot analysis performed to evaluate the active KRAS (mutant KRAS) expression inhibitory activities of SEQ ID NOs: 90 to 93, each linked by a GGGGSGGGGSGGGGS (SEQ ID NO: 95) linker.

As shown in FIG. 7, it was confirmed that SEQ ID NOs: 90 to 93 all decreased active KRAS compared to treatment with EGF alone. In addition, it could be seen that pERK1/2, which is a signal downstream of KRAS, was also reduced by SEQ ID NOs: 91 to 92.

Example 5: Evaluation of Cell Penetration Abilities of Cancer Cell-Penetrating and KRAS Mutant-Targeting Antibody and scFv In order to test the cancer cell penetrating ability of the antibody or scFv, $1\times10^5$ H358 cells were seeded, and after 48 hours, each of SEQ ID NOs: 20 to 23 was added thereto at a concentration of 500 nM, and the cells were cultured for 30 minutes. The cells were fixed with 4% paraformaldehyde, permeabilized with 0.1% Triton-X100 for 10 minutes, and blocked with 2% BSA. KRAS in the cells was reacted with an anti-RAS antibody (Origene, cst53270) at a dilution ratio of 1:1,000, and reacted with the secondary antibody anti-Rabbit Alexa Fluor 488 (Invitrogen, A27034) at a dilution ratio of 1:2,000. Each of SEQ ID NOs: 20 to 23 was reacted with a V5-Tag antibody (Origene, cst 13202) at a dilution ratio of 1:1,000, and reacted with anti-mouse Alexa Fluor 555 (Invitrogene, A28180) at a dilution ratio of 1:1,000. Cell nuclei were stained with 0.1 μg/mL DAPI (Thermofisher, R37606). SEQ ID NOs: 20 to 23 that penetrated the cells were measured with a confocal laser scanning microscope.

Figure 8:
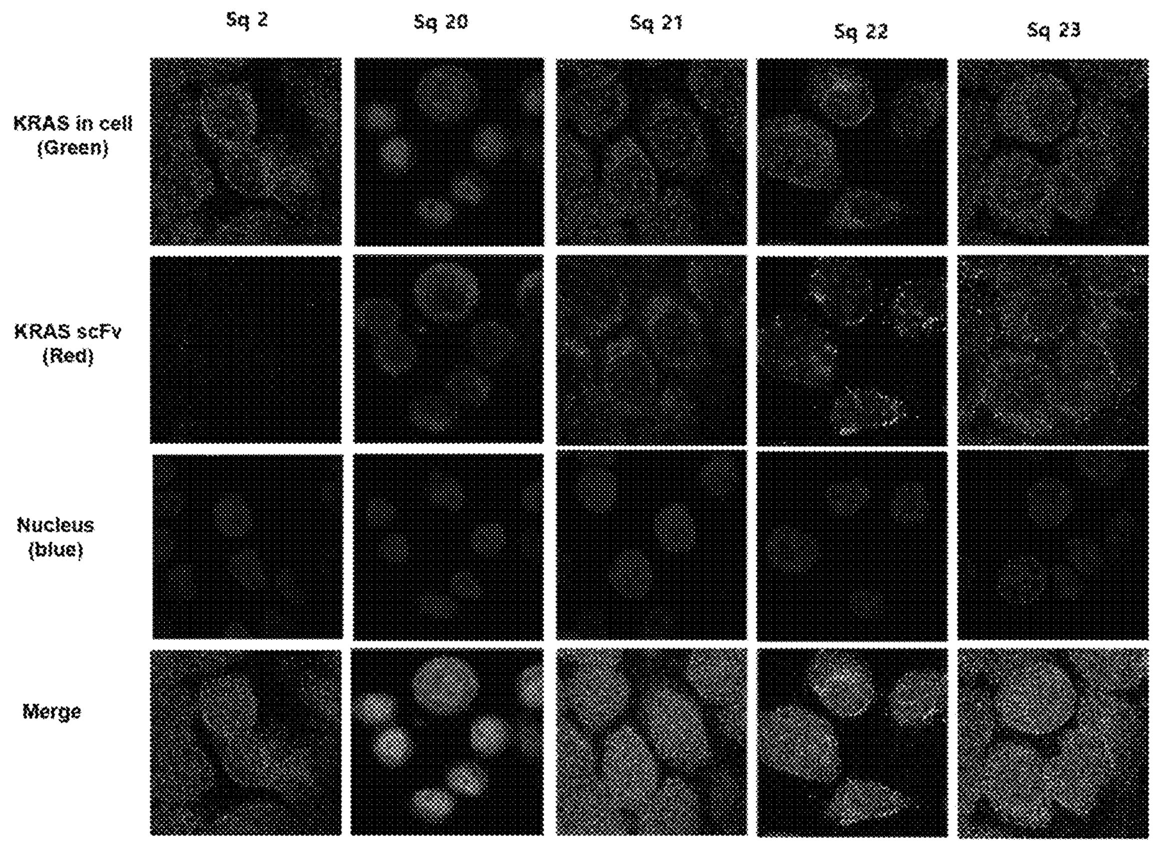
FIG. 8 shows the results of analyzing the ability of SEQ ID NOs: 20 to 23 to penetrate cancer cells.

As a result, as shown in FIG. 8, it could be seen that all of SEQ ID NOs: 20 to 23, except for SEQ ID NO: 2, penetrated the cells. In addition, it could be seen that SEQ ID NOs: 20 to 23 co-localized with KRAS present in the cancer cells. Accordingly, it could be seen that SEQ ID NOs: 20 to 23 could penetrate the cells and bind to KRAS present in the cells.

Example 6: Evaluation of Distribution of Cancer Cell-Penetrating and KRAS Mutant-Targeting Antibody and scFv in Cancer Tissue in Tumor Xenograft Animal Model A mixture of $1\times10^6$ H358 cells and 100 μl of Matrigel (BD Bioscience, San Diego, CA, USA) was transplanted into the thigh of each of 5-6 weeks old female Balb/c nude mice (5-6 weeks old; Japan SLC Inc., Hamamatsu, Japan) to form a tumor having a volume of 100 $mm^3$. Each of Cy5.5-labeled SEQ ID NO: 2, Cy5.5-labeled SEQ ID NO: 23 and Cy5.5 was injected intraperitoneally at a dose of 20 μg per mouse, and after 24 hours, the distribution of fluorescence in each major organ and cancer tissue was observed.

Figure 9:
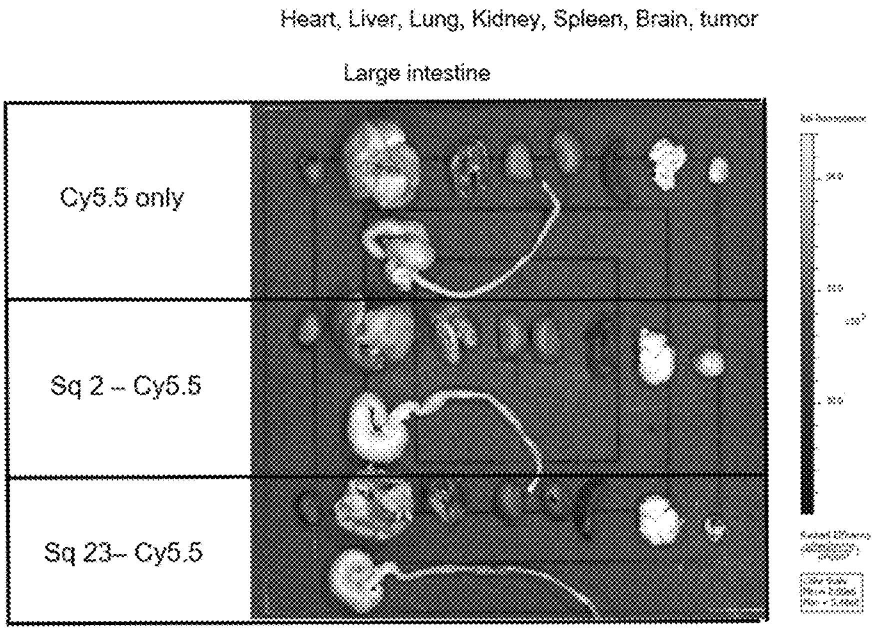
FIG. 9 shows the results of evaluating the distribution of SEQ ID NOs: 2 and 23 in cancer tissue in a tumor xenograft animal model.

As a result, as shown in FIG. 9, it could be seen that SEQ ID NO: 23 was distributed mainly in the cancer tissue 24 hours after injection, and a portion thereof was excreted by the kidney.

Figure 10:
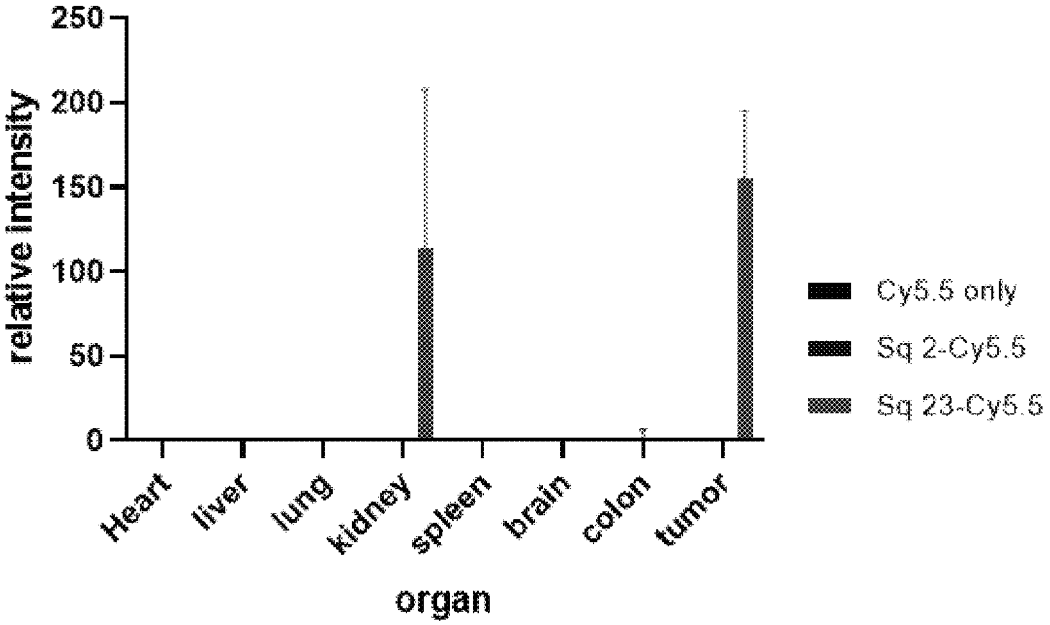
FIG. 10 shows the fluorescence intensity of cancer tissue in a tumor xenograft animal model.

In addition, as shown in FIG. 10, it could be seen that, when the fluorescence intensity was measured, SEQ ID NO: 23 had the highest fluorescence intensity in the cancer tissue.

Example 7: Evaluation of Tumor Inhibitory Activities of Cancer Cell-Penetrating and KRAS Mutant-Targeting Antibody and scFv in Tumor Xenograft Animal Model A mixture of $1\times10^6$ H358 cells and 100 μl of Matrigel (BD Bioscience, San Diego, CA, USA) was transplanted into the thigh of each of 5-6 weeks old female Balb/c nude mice (5-6 weeks old; Japan SLC Inc., Hamamatsu, Japan) to form a tumor having a volume of 100 mm3. Each of SEQ ID NO: 2 and SEQ ID NO: 23 was injected intraperitoneally at a dose of 1 mg/kg twice a week for 30 days. The volume of the tumor was measured with a vernier caliper at intervals of 3 to 4 days, and on day 30, the mice were euthanized and the tumor was excised and photographed.

Figure 11:
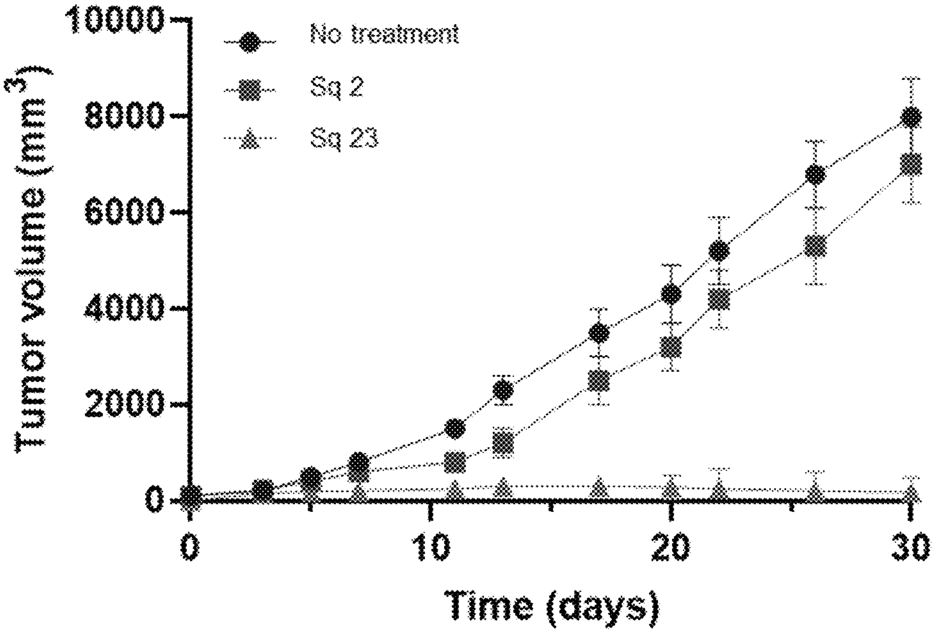
FIG. 11 shows the tumor inhibitory effects of SEQ ID NOs: 2 and 23.
Figure 12:
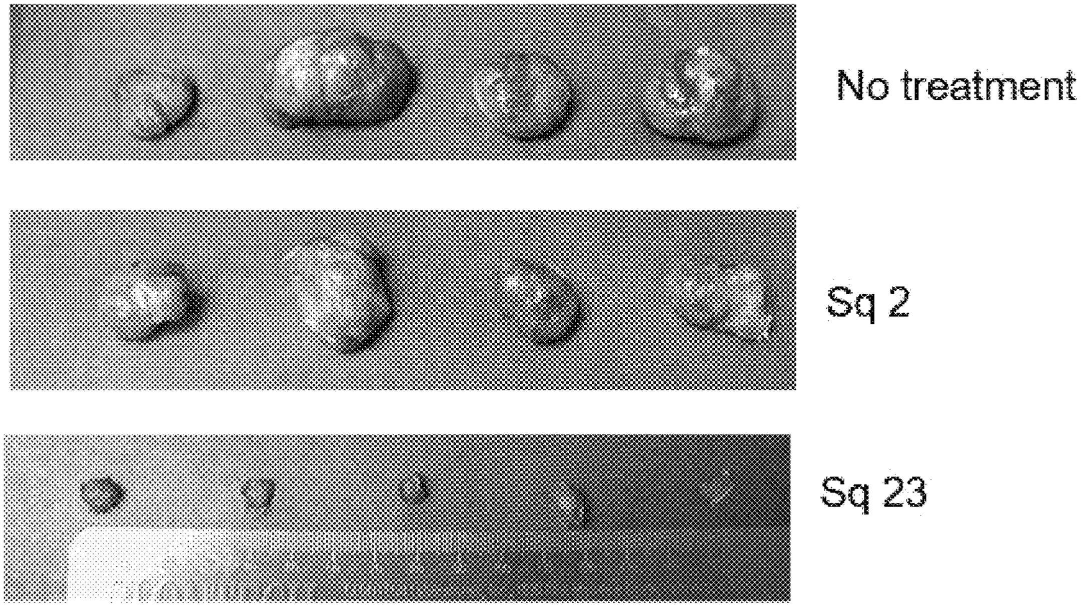
FIG. 12 shows changes in volumes of tumors formed by H358 and images of cancer tissue after euthanasia.

As a result, as shown in FIGS. 11 and 12, it was confirmed that SEQ ID NO: 2 did not have a tumor inhibitory effect, but SEQ ID NO: 23 had an excellent tumor inhibitory effect. This proves that SEQ ID NO: 23 that penetrated the cancer tissue effectively inhibits the growth of tumor cells.

Example 8: Effects of Fusion Proteins of SEQ ID NOs: 80 to 83 Produced by Chemical Conjugation

Example 8-1: Evaluation of Active KRAS (Mutant KRAS) Expression Inhibitory Activities of Cancer Cell-Penetrating and KRAS Mutant-Targeting Antibody and scFv $1.0\times10^6$ H358 cells (ATCC, CRL-5807) were seeded and cultured in RPMI medium 1640 (1×) (Gibco, 22400-089) for 24 hours, followed by starvation for 16 hours. The cells were treated with 50 ng/mL of EGF (epithelial growth factor, R&D Systems, 236-EG) for 10 minutes and treated with 1 μM of each variant. The cells were cultured at 37° C. for 24 hours. After 24 hours, the medium was removed, each well was washed with PBS, and the cells were harvested and centrifuged at 1,500 rpm for 3 minutes. 150 μL of 1× lysis buffer (1× Lysis/Binding/Wash buffer, 11524S) was added to and mixed with the cells and kept on ice for 5 minutes. The supernatant was separated by centrifugation at 16,000 rpm at 4° C. for 15 minutes. Protein concentration was measured by BCA assay (Thermo Scientific, 23227). Washing was performed with 400 μL of 1× lysis buffer, and centrifugation was performed twice at 6000×g for 15 seconds.

To separate the mutant KRAS, 80 μg of GST-Raf1-RBD was added using Active GTPase Kit (Cell Signaling, 11860S), and 500 μg of the protein was dispensed into the spin cup. After 1 hour of incubation at 4° C., centrifugation was performed at 6000×g for 15 seconds, and then the column was transferred into a fresh tube, and 400 μL of 1× lysis buffer was added thereto. After centrifugation at 6000×g for 15 seconds, the column was transferred into a fresh tube, and 50 μL of 2×SDS buffer (containing 200 μl of 5×SDS sample loading dye and 300 μl of water) was added thereto and reacted for 2 minutes. After centrifugation at 6000×g for 2 minutes, the resulting solution was heated at 100° C. for 7 minutes. The protein (20 μl protein loading volume/lane) was separated by 11% SDS-PAGE electrophoresis and transferred to a nitrocellulose membrane. To measure ERK1/2 which is a signal downstream of KRAS, 30 μg of the protein was electrophoresed by 11% SDS-PAGE and transferred to a nitrocellulose membrane. The membrane was blocked with 5% skim milk in T-TBS for 1 hour and incubated with a primary antibody (diluted 1:1000 in T-TBS) overnight with inversion at 4° C. The membrane was washed with T-TBS 3 times for 10 minutes per washing, and incubated with a secondary antibody (diluted 1:3000 in T-TBS) for 1 hour while inversion at room temperature. The membrane was washed 3 times with T-TBS for 10 minutes per washing, incubated with ECL chemiluminescence substrate (Thermo, 34580), and visualized with Amersham Imager 680 (GE). Information on the antibodies used is shown in Table 9 below.

TABLE 9

Antibodies used

| No. | Antibody name | Manufacturers | Catalog No. |
|---|---|---|---|
| 1 | GST | Abcam | Ab19256 |
| 2 | Active KRAS | Santa Cruz | SC-30 |
| 3 | RAS(E4K9L) | Cell Signaling | 91054S |
| 4 | p-B-Raf(S445) | Cell Signaling | 2696S |
| 5 | p-MEK1/2(S221) | Cell Signaling | 2338S |
| 6 | p-Erk1/2 | Santa Cruz | SC-7383 |
| 7 | GAPDH | Cell Signaling | 2118S |
| 8 | Goat anti-Rabbit IgG | BETHYL | A120-101P |
| 9 | Goat anti-Mouse IgG | BETHYL | A90-116P |

Figure 13:
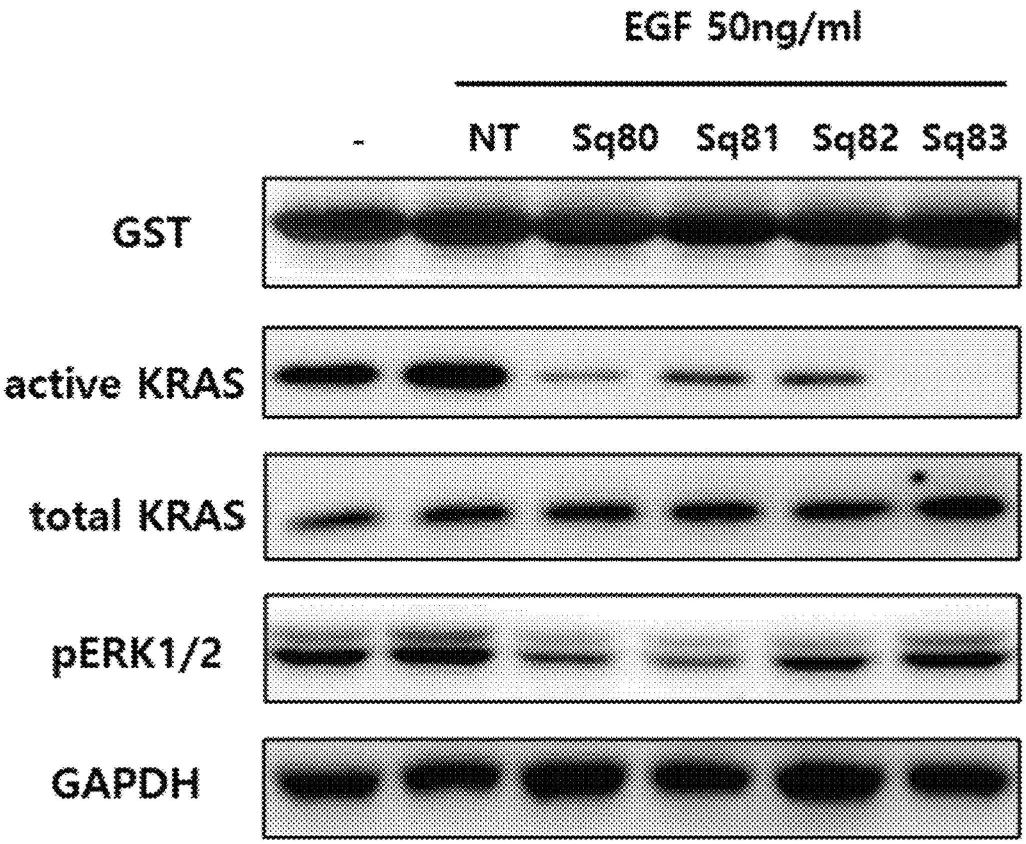
FIG. 13 shows the results of Western blot analysis performed to evaluate the active KRAS (mutant KRAS) expression inhibitory activities of SEQ ID NOs: 80 to 83 produced by chemical conjugation.

SEQ ID NOs: 80 to 83 were produced by linking the cell-penetrating peptide to the KRAS mutant-targeting antibody or scFv by chemical conjugation. As a result, as shown in FIG. 13, it was confirmed that SEQ ID NOs: 80 to 83 all decreased active KRAS compared to treatment with EGF alone. In addition, it could be seen that pERK1/2, which is a signal downstream of KRAS, was also decreased by SEQ ID NOs: 80 to 83.

Example 8-2: Evaluation of Inhibitory Activities of Cancer Cell-Penetrating and KRAS Mutant-Targeting Antibody and scFv Against Cancer Cells with Different KRAS Mutant Expression Levels In order to evaluate the cancer cell-specific growth inhibitory activities of the cancer cell-penetrating and KRAS mutant-targeting antibody and scFv according to the present invention, H358 cells (cancer cells expressing KRAS mutant) or human dermal fibroblasts (normal cells) were dispensed into a 96-well plate at a density of $5\times10^3$ cells/well, and then cultured in RPMI medium 1640 (Gibco) for 24 hours. The cells were treated with each of scFvs (SEQ ID NOs: 3 and 80 to 83) at a concentration of 0 to 5 μM. Cytotoxicity was measured using CCK-8 (Cell Counting Kit-8, CK04, Dojindo Lab.). Cytotoxicity was measured using CCK-8 (Cell Counting Kit-8, CK04, Dojindo Lab.). 48 hours after treatment with each scFv, the medium was removed, and 100 μl of CCK-8 solution was dispensed to fresh RPMI medium 1640. After 1 hour and 30 minutes, the absorbance at 450 nm was measured.

Figure 14:
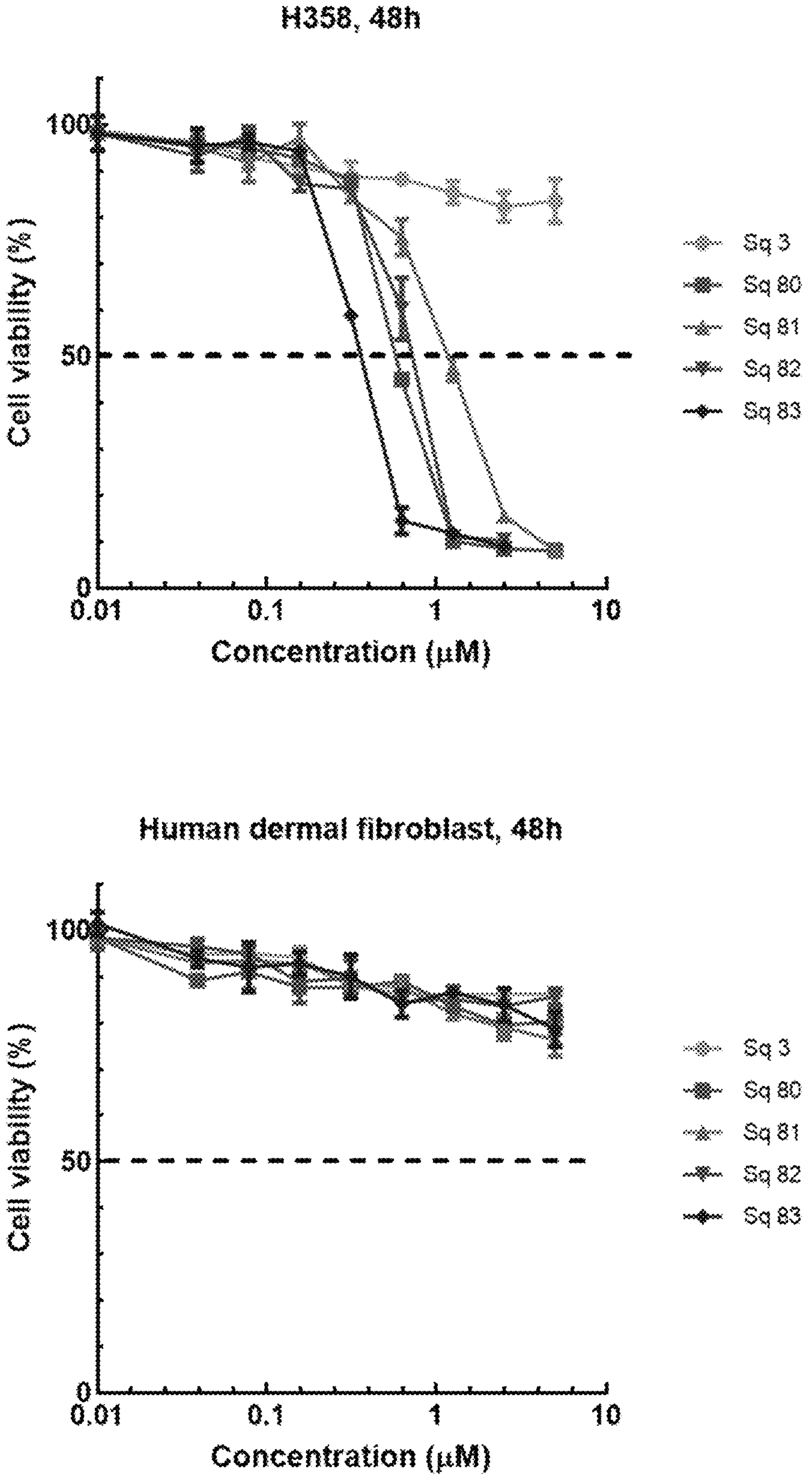
FIG. 14 shows the results of evaluating the cancer cell-specific killing effects of SEQ ID NOs: 80 to 83 produced by chemical conjugation.

As a result, as shown in FIG. 14, it was confirmed that SEQ ID NOs: 80 to 83 showed an $IC_{50}$ value of 313 to 1250 nM (concentration at which 50% of cells are killed) in the H358 cells, and for SEQ ID NO: 3, the $IC_{50}$ value could not be measured even at a concentration of 5 μM. This is believed to be because SEQ ID NO: 3 did not show the cancer cell killing effect by being unable to penetrate the cancer cells, but SEQ ID NOs: 80 to 83 exhibited cytotoxicity by being able to penetrate the cancer cells. The human dermal fibroblasts that are normal cells showed a cell viability of 80% or higher at all the concentrations. This means that the cancer cell-penetrating and KRAS mutant-targeting scFv conjugates have cancer cell-specific cytotoxicity.

Example 8-3: Evaluation of Cell Penetration Abilities of Cancer Cell-Penetrating and KRAS Mutant-Targeting Antibody and scFv In order to test the cancer cell penetrating ability of the antibody or scFv, $1\times10^5$ H358 cells were seeded, and after 48 hours, each of SEQ ID NOs: 80 to 83 was added thereto at a concentration of 500 nM, and the cells were cultured for 30 minutes. The cells were fixed with 4% paraformaldehyde, permeabilized with 0.1% Triton-X100 for 10 minutes, and blocked with 2% BSA. KRAS in the cells was reacted with an anti-RAS antibody (Origene, cst53270) at a dilution ratio of 1:1,000, and reacted with the secondary antibody anti-Rabbit Alexa Fluor 488 (Invitrogen, A27034) at a dilution ratio of 1:2,000. Each of SEQ ID NOs: 80 to 83 was reacted with a V5-Tag antibody (Origene, cst 13202) at a dilution ratio of 1:1,000, and reacted with an anti-mouse Alexa Fluor 555 (Invitrogene, A28180) at a dilution ratio of 1:1,000. Cell nuclei were stained with 0.1 μg/mL DAPI (Thermofisher, R37606). SEQ ID NOs: 80 to 83 that penetrated the cells were measured with a confocal laser scanning microscope.

Figure 15:
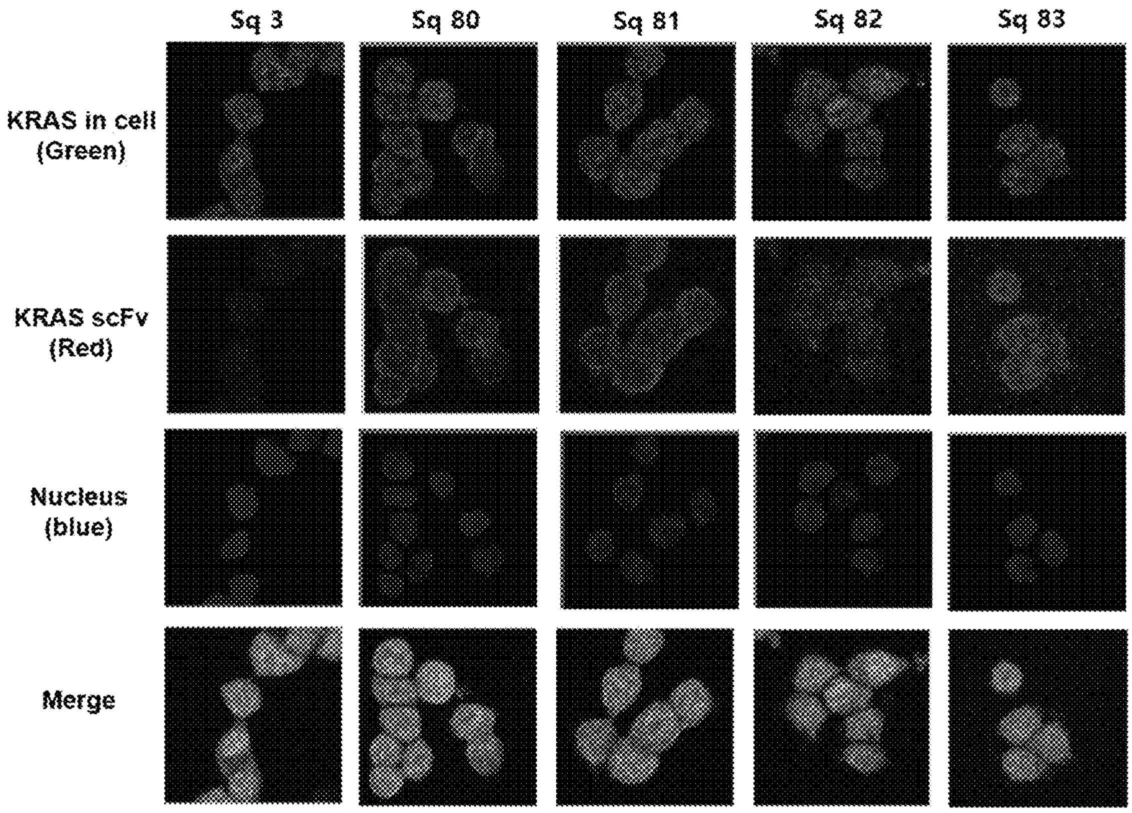
FIG. 15 shows the results of evaluating the cancer cell penetration abilities of SEQ ID NOs: 80 to 83 produced by chemical conjugation.

As a result, as shown in FIG. 15, it could be seen that all of SEQ ID NOs: 80 to 83, except for SEQ ID NO: 3, penetrated the cells. In addition, it could be seen that SEQ ID NOs: 80 to 83 co-localized with KRAS present in the cancer cells. Accordingly, it could be seen that SEQ ID NOs: 80 to 83 could penetrate the cells and bind to KRAS present in the cells.

Example 8-4: Evaluation of Distribution of Cancer Cell-Penetrating and KRAS Mutant-Targeting Antibody and scFv in Cancer Tissue in Tumor Xenograft Animal Model A mixture of $1\times10^6$ H358 cells and 100 μl of Matrigel (BD Bioscience, San Diego, CA, USA) was transplanted into the thigh of each of 5-6 weeks old female Balb/c nude mice (5-6 weeks old; Japan SLC Inc., Hamamatsu, Japan) to form a tumor having a volume of 100 mm3. Each of Cy5.5-labeled SEQ ID NO: 3, Cy5.5-labeled SEQ ID NO: 83 and Cy5.5 was injected intraperitoneally at a dose of 20 μg per mouse, and after 24 hours, the distribution of fluorescence distributed in each major organ and cancer tissue was observed.

Figure 16:
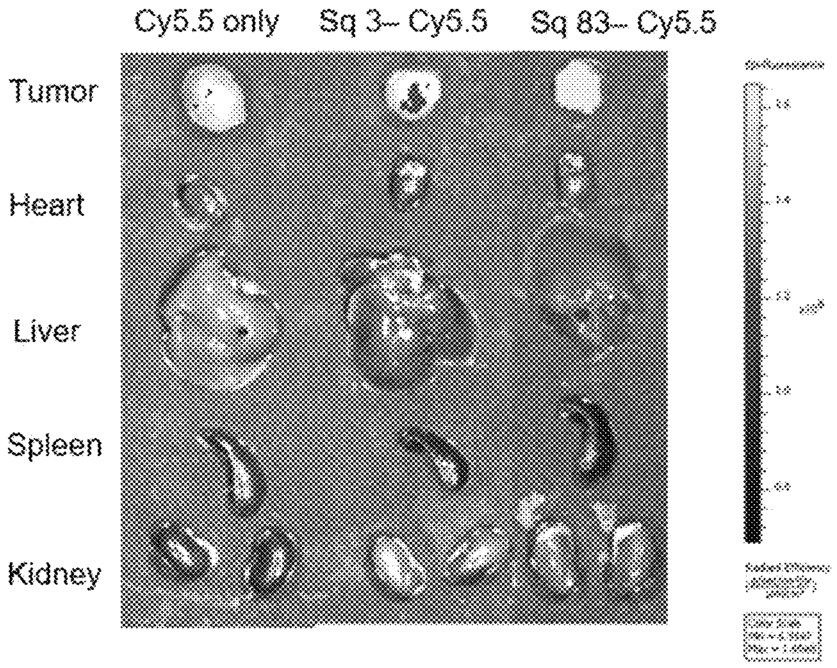
FIG. 16 shows the results of evaluating the distribution to cancer tissue in a tumor xenograft animal model.

As a result, as shown in FIG. 16, it could be seen that SEQ ID NO: 83 was distributed mainly in the cancer tissue 24 hours after injection, and a portion thereof was excreted by the kidney.

Figure 17:
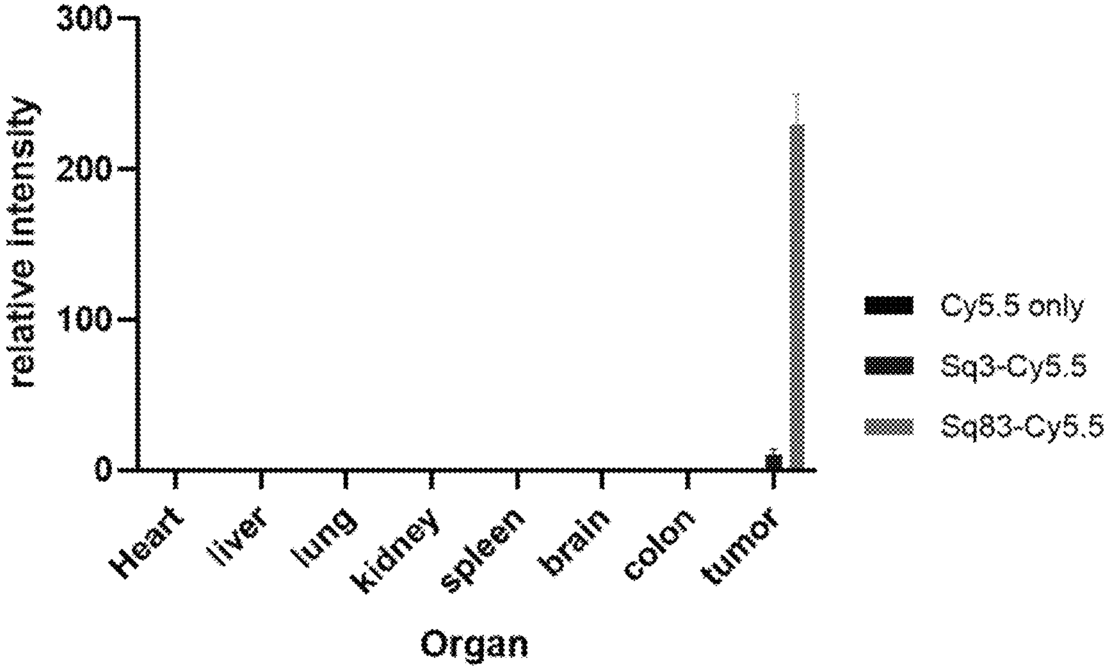
FIG. 17 shows the fluorescence intensity of cancer tissue in a tumor xenograft animal model.

In addition, as shown in FIG. 17, it could be seen that, when the fluorescence intensity was measured, SEQ ID NO: 83 had the highest fluorescence intensity in the cancer tissue.

Example 8-5: Evaluation of Tumor Inhibitory Activities of Cancer Cell-Penetrating and KRAS Mutant-Targeting Antibody and scFv in Tumor Xenograft Animal Model A mixture of $1\times10^6$ H358 cells and 100 µl of Matrigel (BD Bioscience, San Diego, CA, USA) was transplanted into the thigh of each of 5-6 weeks old female Balb/c nude mice (5-6 weeks old; Japan SLC Inc., Hamamatsu, Japan) to form a tumor having a volume of 100 mm3. Each of SEQ ID NO: 3 and SEQ ID NO: 83 was injected intraperitoneally at a dose of 1 mg/kg twice a week for 30 days. The volume of the tumor was measured with a vernier caliper at intervals of 3 to 4 days, and on day 30, the mice were euthanized and the tumor was excised and photographed.

Figure 18:
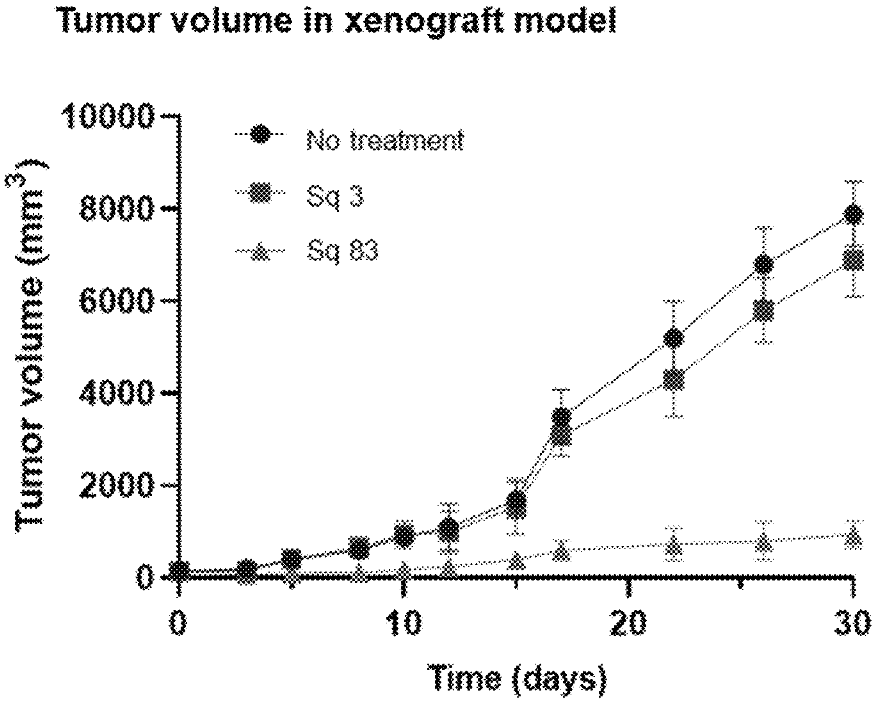
FIG. 18 shows the tumor inhibitory effects of SEQ ID NOs: 3 and 83.
Figure 19:
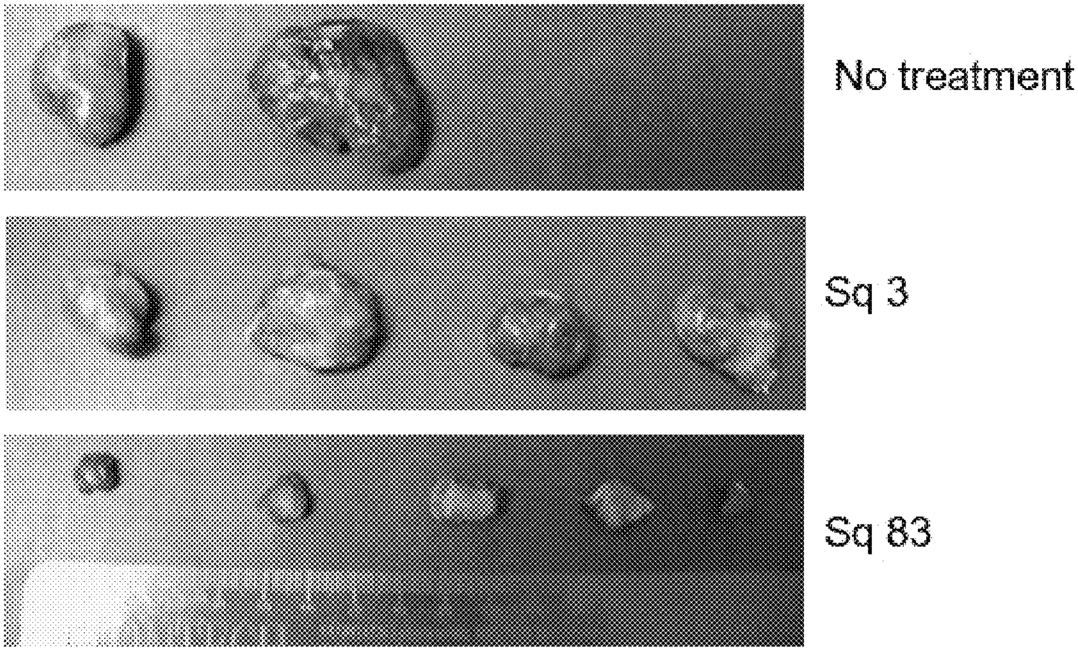
FIG. 19 shows changes in volumes of tumors formed by H358 and images of cancer tissue after euthanasia.

As a result, as shown in FIGS. 18 and 19, it was confirmed that SEQ ID NO: 3 did not have a tumor inhibitory effect, but SEQ ID NO: 83 had an excellent tumor inhibitory effect. This proves that SEQ ID NO: 83 that penetrated the cancer tissue effectively inhibits the growth of tumor cells.

Although the present invention has been described in detail with reference to specific features, it will be apparent to those skilled in the art that this description is only of a preferred embodiment thereof, and does not limit the scope of the present invention. Thus, the substantial scope of the present invention will be defined by the appended claims and equivalents thereto.

INDUSTRIAL APPLICABILITY

An intracellular oncogenic protein or a mutant thereof acts as an important factor in tumor pathogenesis. In the present invention, an intracellular oncogenic protein or oncogenic mutant protein-targeting antibody or a single-chain variable fragment thereof is used which inhibits the function of the intracellular oncogenic protein or mutant thereof by binding thereto. To enhance the accessibility of the antibody or single-chain variable fragment thereof to cancer cells, a cancer cell-penetrating peptide is linked to the antibody or single-chain variable fragment thereof. The fusion protein produced as described above may effectively penetrate tumor cells, thereby maximizing the antitumor or anticancer effect of the antibody or single-chain variable fragment thereof that targets the intracellular oncogenic protein or oncogenic mutant protein.

SEQUENCE LIST FREE TEXT

An electronic file is attached.

The invention claimed is:

1. A fusion protein comprising (i) an antibody or a single-chain variable fragment thereof, which targets an intracellular oncogenic protein or oncogenic mutant protein, linked with (ii) a cancer cell-penetrating peptide, wherein the antibody or single-chain variable fragment thereof is selected from the group consisting of SEQ ID NOs: 1 to 3.

2. The fusion protein of claim 1, wherein the intracellular oncogenic protein or oncogenic mutant protein is KRAS or androgen receptor.

3. The fusion protein of claim 1, wherein the cancer cell-penetrating peptide is selected from the group consisting of SEQ ID NO: 86 to SEQ ID NO: 89.

4. The fusion protein of claim 1, wherein the cancer cell-penetrating peptide is linked via a linker to the N-terminus or C-terminus of the antibody or single-chain variable peptide thereof.

5. The fusion protein of claim 4, wherein the linker is GGGGS (SEQ ID NO: 94) or GGGGSGGGGSGGGGS (SEQ ID NO: 95).

6. The fusion protein of claim 1, which is a fusion protein wherein any one cancer cell-penetrating peptide selected from the group consisting of SEQ ID NO: 86 to SEQ ID NO: 89 is linked via a linker to a lysine or cysteine residue of any one single-chain variable fragment selected from the group consisting of SEQ ID NOs: 1 to 3.

7. The fusion protein of claim 6, wherein the linker is CGGGGG (SEQ ID NO: 96) or CGGGGGSSGGGGG (SEQ ID NO: 97).

8. The fusion protein of claim 1, which comprises an amino acid sequence selected from the group consisting of SEQ ID NO: 12 to SEQ ID NO: 59, SEQ ID NO: 68 to SEQ ID NO: 83, and SEQ ID NO: 90 to SEQ ID NO: 93.

9. A nucleic acid encoding the fusion protein of claim 1.

10. A recombinant vector into which the nucleic acid of claim 9 has been introduced.

11. A recombinant cell into which the recombinant vector of claim 10 has been introduced.

12. The recombinant cell of claim 11, wherein the recombinant cell is an *E. coli* or mammalian cell.

13. A method for producing the fusion protein of claim 1 comprising steps of:

(a) expressing the fusion protein of claim 1 by culturing the recombinant vector of claim 11; and (b) recovering the expressed fusion protein.

14. A method of treating a tumor comprising administering the fusion protein of claim 1 as an active ingredient.

15. The method of claim 14, wherein the tumor is at least one selected from the group consisting of non-small cell lung cancer, colorectal cancer, pancreatic cancer, bladder cancer, kidney cancer, thyroid cancer, breast cancer, colon cancer, liver cancer, brain tumor, skin cancer, melanoma, colorectal cancer, prostate cancer, and blood cancer.

* * * * *

SEQUENCE LISTING

```
<160> NUMBER OF SEQ ID NOS: 98

<210> SEQ ID NO 1
<211> LENGTH: 271
<212> TYPE: PRT
<213> ORGANISM: Artificial Sequence
<220> FEATURE:
<223> OTHER INFORMATION: Synthetic construct

<400> SEQUENCE: 1

Met Ala Trp Val Trp Thr Leu Leu Phe Leu Met Ala Ala Ala Gln Ser
1               5                   10                  15

Ile Gln Ala Glu Trp Ile Lys Gln Arg Pro Gly Gln Gly Leu Glu Trp
            20                  25                  30

Ile Gly Val Ile His Pro Gly Asn Gly Gly Thr Asn Tyr Asn Glu Asn
        35                  40                  45

Phe Lys Gly Lys Ala Thr Leu Thr Ala Asp Lys Ser Ser Ser Thr Ala
    50                  55                  60

Tyr Met Gln Leu Ser Ser Leu Thr Ser Asp Asp Ser Ala Val Tyr Phe
65                  70                  75                  80

Cys Ala Ser Gly Asn Asp Gly Ser Tyr Trp Gly Gln Gly Thr Thr Val
                85                  90                  95

Thr Val Ser Ser Gly Gly Gly Gly Ser Gly Lys Gly Gly Ser Gly Gly
            100                 105                 110

Gly Gly Ser Gly Gly Gly Gly Ser Asp Ile Glu Leu Thr Gln Ser Pro
        115                 120                 125

Ser Ser Leu Thr Val Thr Ala Gly Glu Lys Val Thr Met Ser Cys Lys
    130                 135                 140

Ser Ser Gln Ser Leu Leu Asn Ser Gly Asp Gln Lys Ile Tyr Leu Thr
145                 150                 155                 160
```

```
Trp Tyr Gln Gln Lys Pro Gly Gln Pro Pro Lys Leu Leu Ile Tyr Trp
                165                 170                 175

Ala Ser Thr Arg Glu Ser Gly Val Pro Asp Arg Phe Thr Gly Ser Val
            180                 185                 190

Ser Gly Thr Asp Phe Thr Leu Thr Ile Ser Ser Val Gln Ala Glu Asp
        195                 200                 205

Leu Ala Val Tyr Tyr Cys Gln Asn Asp Tyr Asn Tyr Pro Tyr Thr Phe
    210                 215                 220

Gly Gly Gly Thr Lys Leu Glu Ile Lys Arg Gly Ser Glu Asn Leu Tyr
225                 230                 235                 240

Phe Gln Gly Gly Ser Gly Lys Pro Ile Pro Asn Pro Leu Leu Gly Leu
                245                 250                 255

Asp Ser Thr Gly Gly Ser Gly Gly Ser His His His His His His
            260                 265                 270


<210> SEQ ID NO 2
<211> LENGTH: 254
<212> TYPE: PRT
<213> ORGANISM: Artificial Sequence
<220> FEATURE:
<223> OTHER INFORMATION: Synthetic construct

<400> SEQUENCE: 2

Met Ala Gln Val Lys Leu Gln Glu Ser Gly Pro Glu Leu Val Arg Pro
1               5                   10                  15

Gly Thr Ser Val Lys Val Ser Cys Lys Ala Ser Gly Tyr Ala Phe Thr
            20                  25                  30

Asn Tyr Leu Ile Glu Trp Ile Lys Gln Arg Pro Gly Gln Gly Leu Glu
        35                  40                  45

Trp Ile Gly Val Ile His Pro Gly Asn Gly Gly Thr Asn Tyr Asn Glu
    50                  55                  60

Asn Phe Lys Gly Lys Ala Thr Leu Thr Ala Asp Lys Ser Ser Ser Thr
65                  70                  75                  80

Ala Tyr Met Gln Leu Ser Ser Leu Thr Ser Asp Asp Ser Ala Val Tyr
                85                  90                  95

Phe Cys Ala Ser Gly Asn Asp Gly Ser Tyr Trp Gly Gln Gly Thr Thr
            100                 105                 110

Val Thr Val Ser Ser Gly Gly Gly Gly Ser Gly Gly Gly Gly Ser Gly
        115                 120                 125

Gly Gly Gly Ser Asp Ile Glu Leu Thr Gln Ser Pro Ser Ser Leu Thr
    130                 135                 140

Val Thr Ala Gly Glu Lys Val Thr Met Ser Cys Lys Ser Ser Gln Ser
145                 150                 155                 160

Leu Leu Asn Ser Gly Asp Gln Lys Ile Tyr Leu Thr Trp Tyr Gln Gln
                165                 170                 175

Lys Pro Gly Gln Pro Pro Lys Leu Leu Ile Tyr Trp Ala Ser Thr Arg
            180                 185                 190

Glu Ser Gly Val Pro Asp Arg Phe Thr Gly Ser Val Ser Gly Thr Asp
        195                 200                 205

Phe Thr Leu Thr Ile Ser Ser Val Gln Ala Glu Asp Leu Ala Val Tyr
    210                 215                 220

Tyr Cys Gln Asn Asp Tyr Asn Tyr Pro Tyr Thr Phe Gly Gly Gly Thr
225                 230                 235                 240

Lys Leu Glu Ile Lys Arg Leu Glu His His His His His His
                245                 250
```

<210> SEQ ID NO 3
<211> LENGTH: 272
<212> TYPE: PRT
<213> ORGANISM: Artificial Sequence
<220> FEATURE:
<223> OTHER INFORMATION: Synthetic construct

<400> SEQUENCE: 3

```
Met Ala Trp Val Trp Thr Leu Leu Phe Leu Met Ala Ala Ala Gln Ser
1               5                   10                  15

Ile Gln Ala Glu Trp Ile Lys Gln Arg Pro Gly Gln Gly Leu Glu Trp
            20                  25                  30

Ile Gly Val Ile His Pro Gly Asn Gly Gly Thr Asn Tyr Asn Glu Asn
        35                  40                  45

Phe Lys Gly Lys Ala Thr Leu Thr Ala Asp Lys Ser Ser Ser Thr Ala
    50                  55                  60

Tyr Met Gln Leu Ser Ser Leu Thr Ser Asp Asp Ser Ala Val Tyr Phe
65                  70                  75                  80

Cys Ala Ser Gly Asn Asp Gly Ser Tyr Trp Gly Gln Gly Thr Thr Val
                85                  90                  95

Thr Val Ser Ser Gly Gly Gly Gly Ser Gly Lys Gly Gly Ser Gly Gly
            100                 105                 110

Gly Gly Ser Gly Gly Gly Gly Ser Asp Ile Glu Leu Thr Gln Ser Pro
        115                 120                 125

Ser Ser Leu Thr Val Thr Ala Gly Glu Lys Val Thr Met Ser Cys Lys
    130                 135                 140

Ser Ser Gln Ser Leu Leu Asn Ser Gly Asp Gln Lys Ile Tyr Leu Thr
145                 150                 155                 160

Trp Tyr Gln Gln Lys Pro Gly Gln Pro Pro Lys Leu Leu Ile Tyr Trp
                165                 170                 175

Ala Ser Thr Arg Glu Ser Gly Val Pro Asp Arg Phe Thr Gly Ser Val
            180                 185                 190

Ser Gly Thr Asp Phe Thr Leu Thr Ile Ser Ser Val Gln Ala Glu Asp
        195                 200                 205

Leu Ala Val Tyr Tyr Cys Gln Asn Asp Tyr Asn Tyr Pro Tyr Thr Phe
    210                 215                 220

Gly Gly Gly Thr Lys Cys Leu Glu Ile Lys Arg Gly Ser Glu Asn Leu
225                 230                 235                 240

Tyr Phe Gln Gly Gly Ser Gly Lys Pro Ile Pro Asn Pro Leu Leu Gly
                245                 250                 255

Leu Asp Ser Thr Gly Gly Ser Gly Gly Ser His His His His His His
            260                 265                 270
```

<210> SEQ ID NO 4
<211> LENGTH: 16
<212> TYPE: PRT
<213> ORGANISM: Artificial Sequence
<220> FEATURE:
<223> OTHER INFORMATION: Synthetic construct

<400> SEQUENCE: 4

```
Gly Gly Gly Gly Ser His Arg Arg Cys Asn Lys Asn Asn Lys Lys Arg
1               5                   10                  15
```

<210> SEQ ID NO 5
<211> LENGTH: 16
<212> TYPE: PRT

-continued

<213> ORGANISM: Artificial Sequence
<220> FEATURE:
<223> OTHER INFORMATION: Synthetic construct

<400> SEQUENCE: 5

Gly Gly Gly Gly Ser His Arg Arg Cys Asn Pro Asn Asn Lys Lys Arg
1 5 10 15

<210> SEQ ID NO 6
<211> LENGTH: 19
<212> TYPE: PRT
<213> ORGANISM: Artificial Sequence
<220> FEATURE:
<223> OTHER INFORMATION: Synthetic construct

<400> SEQUENCE: 6

Gly Gly Gly Gly Ser Val Ser Arg Arg Arg Arg Arg Arg Gly Gly Arg
1 5 10 15

Arg Arg Arg

<210> SEQ ID NO 7
<211> LENGTH: 20
<212> TYPE: PRT
<213> ORGANISM: Artificial Sequence
<220> FEATURE:
<223> OTHER INFORMATION: Synthetic construct

<400> SEQUENCE: 7

Gly Gly Gly Gly Ser Gly Lys Cys Ser Thr Arg Gly Arg Lys Cys Cys
1 5 10 15

Arg Arg Lys Lys
20

<210> SEQ ID NO 8
<211> LENGTH: 16
<212> TYPE: PRT
<213> ORGANISM: Artificial Sequence
<220> FEATURE:
<223> OTHER INFORMATION: Synthetic construct

<400> SEQUENCE: 8

His Arg Arg Cys Asn Lys Asn Asn Lys Lys Arg Gly Gly Gly Gly Ser
1 5 10 15

<210> SEQ ID NO 9
<211> LENGTH: 16
<212> TYPE: PRT
<213> ORGANISM: Artificial Sequence
<220> FEATURE:
<223> OTHER INFORMATION: Synthetic construct

<400> SEQUENCE: 9

His Arg Arg Cys Asn Pro Asn Asn Lys Lys Arg Gly Gly Gly Gly Ser
1 5 10 15

<210> SEQ ID NO 10
<211> LENGTH: 19
<212> TYPE: PRT
<213> ORGANISM: Artificial Sequence
<220> FEATURE:
<223> OTHER INFORMATION: Synthetic construct

<400> SEQUENCE: 10

Val Ser Arg Arg Arg Arg Arg Arg Gly Gly Arg Arg Arg Arg Gly Gly
1 5 10 15

Gly Gly Ser

<210> SEQ ID NO 11
<211> LENGTH: 20
<212> TYPE: PRT
<213> ORGANISM: Artificial Sequence
<220> FEATURE:
<223> OTHER INFORMATION: Synthetic construct

<400> SEQUENCE: 11

```
Gly Lys Cys Ser Thr Arg Gly Arg Lys Cys Cys Arg Arg Lys Lys Gly
1               5                   10                  15

Gly Gly Gly Ser
            20
```

<210> SEQ ID NO 12
<211> LENGTH: 287
<212> TYPE: PRT
<213> ORGANISM: Artificial Sequence
<220> FEATURE:
<223> OTHER INFORMATION: Synthetic construct

<400> SEQUENCE: 12

```
Met Ala Trp Val Trp Thr Leu Leu Phe Leu Met Ala Ala Ala Gln Ser
1               5                   10                  15

Ile Gln Ala Glu Trp Ile Lys Gln Arg Pro Gly Gln Gly Leu Glu Trp
            20                  25                  30

Ile Gly Val Ile His Pro Gly Asn Gly Gly Thr Asn Tyr Asn Glu Asn
        35                  40                  45

Phe Lys Gly Lys Ala Thr Leu Thr Ala Asp Lys Ser Ser Ser Thr Ala
    50                  55                  60

Tyr Met Gln Leu Ser Ser Leu Thr Ser Asp Asp Ser Ala Val Tyr Phe
65                  70                  75                  80

Cys Ala Ser Gly Asn Asp Gly Ser Tyr Trp Gly Gln Gly Thr Thr Val
                85                  90                  95

Thr Val Ser Ser Gly Gly Gly Gly Ser Gly Lys Gly Gly Ser Gly Gly
            100                 105                 110

Gly Gly Ser Gly Gly Gly Gly Ser Asp Ile Glu Leu Thr Gln Ser Pro
        115                 120                 125

Ser Ser Leu Thr Val Thr Ala Gly Glu Lys Val Thr Met Ser Cys Lys
    130                 135                 140

Ser Ser Gln Ser Leu Leu Asn Ser Gly Asp Gln Lys Ile Tyr Leu Thr
145                 150                 155                 160

Trp Tyr Gln Gln Lys Pro Gly Gln Pro Pro Lys Leu Leu Ile Tyr Trp
                165                 170                 175

Ala Ser Thr Arg Glu Ser Gly Val Pro Asp Arg Phe Thr Gly Ser Val
            180                 185                 190

Ser Gly Thr Asp Phe Thr Leu Thr Ile Ser Ser Val Gln Ala Glu Asp
        195                 200                 205

Leu Ala Val Tyr Tyr Cys Gln Asn Asp Tyr Asn Tyr Pro Tyr Thr Phe
    210                 215                 220

Gly Gly Gly Thr Lys Gly Gly Gly Gly Ser His Arg Arg Cys Asn Lys
225                 230                 235                 240

Asn Asn Lys Lys Arg Leu Glu Ile Lys Arg Gly Ser Glu Asn Leu Tyr
                245                 250                 255

Phe Gln Gly Gly Ser Gly Lys Pro Ile Pro Asn Pro Leu Leu Gly Leu
            260                 265                 270
```

```
Asp Ser Thr Gly Gly Ser Gly Gly Ser His His His His His His
        275                 280                 285


<210> SEQ ID NO 13
<211> LENGTH: 287
<212> TYPE: PRT
<213> ORGANISM: Artificial Sequence
<220> FEATURE:
<223> OTHER INFORMATION: Synthetic construct

<400> SEQUENCE: 13

Met Ala Trp Val Trp Thr Leu Leu Phe Leu Met Ala Ala Ala Gln Ser
1               5                   10                  15

Ile Gln Ala Glu Trp Ile Lys Gln Arg Pro Gly Gln Gly Leu Glu Trp
            20                  25                  30

Ile Gly Val Ile His Pro Gly Asn Gly Gly Thr Asn Tyr Asn Glu Asn
        35                  40                  45

Phe Lys Gly Lys Ala Thr Leu Thr Ala Asp Lys Ser Ser Ser Thr Ala
    50                  55                  60

Tyr Met Gln Leu Ser Ser Leu Thr Ser Asp Asp Ser Ala Val Tyr Phe
65                  70                  75                  80

Cys Ala Ser Gly Asn Asp Gly Ser Tyr Trp Gly Gln Gly Thr Thr Val
                85                  90                  95

Thr Val Ser Ser Gly Gly Gly Gly Ser Gly Lys Gly Gly Ser Gly Gly
            100                 105                 110

Gly Gly Ser Gly Gly Gly Gly Ser Asp Ile Glu Leu Thr Gln Ser Pro
        115                 120                 125

Ser Ser Leu Thr Val Thr Ala Gly Glu Lys Val Thr Met Ser Cys Lys
    130                 135                 140

Ser Ser Gln Ser Leu Leu Asn Ser Gly Asp Gln Lys Ile Tyr Leu Thr
145                 150                 155                 160

Trp Tyr Gln Gln Lys Pro Gly Gln Pro Pro Lys Leu Leu Ile Tyr Trp
                165                 170                 175

Ala Ser Thr Arg Glu Ser Gly Val Pro Asp Arg Phe Thr Gly Ser Val
            180                 185                 190

Ser Gly Thr Asp Phe Thr Leu Thr Ile Ser Ser Val Gln Ala Glu Asp
        195                 200                 205

Leu Ala Val Tyr Tyr Cys Gln Asn Asp Tyr Asn Tyr Pro Tyr Thr Phe
    210                 215                 220

Gly Gly Gly Thr Lys Gly Gly Gly Gly Ser His Arg Arg Cys Asn Pro
225                 230                 235                 240

Asn Asn Lys Lys Arg Leu Glu Ile Lys Arg Gly Ser Glu Asn Leu Tyr
                245                 250                 255

Phe Gln Gly Gly Ser Gly Lys Pro Ile Pro Asn Pro Leu Leu Gly Leu
            260                 265                 270

Asp Ser Thr Gly Gly Ser Gly Gly Ser His His His His His His
        275                 280                 285


<210> SEQ ID NO 14
<211> LENGTH: 290
<212> TYPE: PRT
<213> ORGANISM: Artificial Sequence
<220> FEATURE:
<223> OTHER INFORMATION: Synthetic construct

<400> SEQUENCE: 14

Met Ala Trp Val Trp Thr Leu Leu Phe Leu Met Ala Ala Ala Gln Ser
1               5                   10                  15
```

```
Ile Gln Ala Glu Trp Ile Lys Gln Arg Pro Gly Gln Gly Leu Glu Trp
            20                  25                  30

Ile Gly Val Ile His Pro Gly Asn Gly Gly Thr Asn Tyr Asn Glu Asn
        35                  40                  45

Phe Lys Gly Lys Ala Thr Leu Thr Ala Asp Lys Ser Ser Ser Thr Ala
    50                  55                  60

Tyr Met Gln Leu Ser Ser Leu Thr Ser Asp Asp Ser Ala Val Tyr Phe
65                  70                  75                  80

Cys Ala Ser Gly Asn Asp Gly Ser Tyr Trp Gly Gln Gly Thr Thr Val
                85                  90                  95

Thr Val Ser Ser Gly Gly Gly Gly Ser Gly Lys Gly Gly Ser Gly Gly
            100                 105                 110

Gly Gly Ser Gly Gly Gly Gly Ser Asp Ile Glu Leu Thr Gln Ser Pro
        115                 120                 125

Ser Ser Leu Thr Val Thr Ala Gly Glu Lys Val Thr Met Ser Cys Lys
    130                 135                 140

Ser Ser Gln Ser Leu Leu Asn Ser Gly Asp Gln Lys Ile Tyr Leu Thr
145                 150                 155                 160

Trp Tyr Gln Gln Lys Pro Gly Gln Pro Pro Lys Leu Leu Ile Tyr Trp
                165                 170                 175

Ala Ser Thr Arg Glu Ser Gly Val Pro Asp Arg Phe Thr Gly Ser Val
            180                 185                 190

Ser Gly Thr Asp Phe Thr Leu Thr Ile Ser Ser Val Gln Ala Glu Asp
        195                 200                 205

Leu Ala Val Tyr Tyr Cys Gln Asn Asp Tyr Asn Tyr Pro Tyr Thr Phe
    210                 215                 220

Gly Gly Gly Thr Lys Gly Gly Gly Gly Ser Val Ser Arg Arg Arg Arg
225                 230                 235                 240

Arg Arg Gly Gly Arg Arg Arg Arg Leu Glu Ile Lys Arg Gly Ser Glu
                245                 250                 255

Asn Leu Tyr Phe Gln Gly Gly Ser Gly Lys Pro Ile Pro Asn Pro Leu
            260                 265                 270

Leu Gly Leu Asp Ser Thr Gly Gly Ser Gly Gly Ser His His His His
        275                 280                 285

His His
    290


<210> SEQ ID NO 15
<211> LENGTH: 291
<212> TYPE: PRT
<213> ORGANISM: Artificial Sequence
<220> FEATURE:
<223> OTHER INFORMATION: Synthetic construct

<400> SEQUENCE: 15

Met Ala Trp Val Trp Thr Leu Leu Phe Leu Met Ala Ala Ala Gln Ser
1               5                   10                  15

Ile Gln Ala Glu Trp Ile Lys Gln Arg Pro Gly Gln Gly Leu Glu Trp
            20                  25                  30

Ile Gly Val Ile His Pro Gly Asn Gly Gly Thr Asn Tyr Asn Glu Asn
        35                  40                  45

Phe Lys Gly Lys Ala Thr Leu Thr Ala Asp Lys Ser Ser Ser Thr Ala
    50                  55                  60

Tyr Met Gln Leu Ser Ser Leu Thr Ser Asp Asp Ser Ala Val Tyr Phe
65                  70                  75                  80
```

```
Cys Ala Ser Gly Asn Asp Gly Ser Tyr Trp Gly Gln Gly Thr Thr Val
                85                  90                  95

Thr Val Ser Ser Gly Gly Gly Gly Ser Gly Lys Gly Gly Ser Gly Gly
            100                 105                 110

Gly Gly Ser Gly Gly Gly Gly Ser Asp Ile Glu Leu Thr Gln Ser Pro
        115                 120                 125

Ser Ser Leu Thr Val Thr Ala Gly Glu Lys Val Thr Met Ser Cys Lys
    130                 135                 140

Ser Ser Gln Ser Leu Leu Asn Ser Gly Asp Gln Lys Ile Tyr Leu Thr
145                 150                 155                 160

Trp Tyr Gln Gln Lys Pro Gly Gln Pro Pro Lys Leu Leu Ile Tyr Trp
                165                 170                 175

Ala Ser Thr Arg Glu Ser Gly Val Pro Asp Arg Phe Thr Gly Ser Val
            180                 185                 190

Ser Gly Thr Asp Phe Thr Leu Thr Ile Ser Ser Val Gln Ala Glu Asp
        195                 200                 205

Leu Ala Val Tyr Tyr Cys Gln Asn Asp Tyr Asn Tyr Pro Tyr Thr Phe
    210                 215                 220

Gly Gly Gly Thr Lys Gly Gly Gly Gly Ser Gly Lys Cys Ser Thr Arg
225                 230                 235                 240

Gly Arg Lys Cys Cys Arg Arg Lys Lys Leu Glu Ile Lys Arg Gly Ser
                245                 250                 255

Glu Asn Leu Tyr Phe Gln Gly Gly Ser Gly Lys Pro Ile Pro Asn Pro
            260                 265                 270

Leu Leu Gly Leu Asp Ser Thr Gly Gly Ser Gly Gly Ser His His His
        275                 280                 285

His His His
    290
```

<210> SEQ ID NO 16
<211> LENGTH: 287
<212> TYPE: PRT
<213> ORGANISM: Artificial Sequence
<220> FEATURE:
<223> OTHER INFORMATION: Synthetic construct

<400> SEQUENCE: 16

```
Met Ala Trp Val Trp Thr Leu Leu Phe Leu Met Ala Ala Ala Gln Ser
1               5                   10                  15

Ile Gln Ala His Arg Arg Cys Asn Lys Asn Asn Lys Lys Arg Gly Gly
            20                  25                  30

Gly Gly Ser Glu Trp Ile Lys Gln Arg Pro Gly Gln Gly Leu Glu Trp
        35                  40                  45

Ile Gly Val Ile His Pro Gly Asn Gly Gly Thr Asn Tyr Asn Glu Asn
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Ser Asp Asp Ser Ala Val Tyr Phe
                85                  90                  95

Cys Ala Ser Gly Asn Asp Gly Ser Tyr Trp Gly Gln Gly Thr Thr Val
            100                 105                 110

Thr Val Ser Ser Gly Gly Gly Gly Ser Gly Lys Gly Gly Ser Gly Gly
        115                 120                 125

Gly Gly Ser Gly Gly Gly Gly Ser Asp Ile Glu Leu Thr Gln Ser Pro
    130                 135                 140
```

```
Ser Ser Leu Thr Val Thr Ala Gly Glu Lys Val Thr Met Ser Cys Lys
145                 150                 155                 160

Ser Ser Gln Ser Leu Leu Asn Ser Gly Asp Gln Lys Ile Tyr Leu Thr
                165                 170                 175

Trp Tyr Gln Gln Lys Pro Gly Gln Pro Pro Lys Leu Leu Ile Tyr Trp
            180                 185                 190

Ala Ser Thr Arg Glu Ser Gly Val Pro Asp Arg Phe Thr Gly Ser Val
        195                 200                 205

Ser Gly Thr Asp Phe Thr Leu Thr Ile Ser Ser Val Gln Ala Glu Asp
    210                 215                 220

Leu Ala Val Tyr Tyr Cys Gln Asn Asp Tyr Asn Tyr Pro Tyr Thr Phe
225                 230                 235                 240

Gly Gly Gly Thr Lys Leu Glu Ile Lys Arg Gly Ser Glu Asn Leu Tyr
                245                 250                 255

Phe Gln Gly Gly Ser Gly Lys Pro Ile Pro Asn Pro Leu Leu Gly Leu
            260                 265                 270

Asp Ser Thr Gly Gly Ser Gly Gly Ser His His His His His His
        275                 280                 285


<210> SEQ ID NO 17
<211> LENGTH: 287
<212> TYPE: PRT
<213> ORGANISM: Artificial Sequence
<220> FEATURE:
<223> OTHER INFORMATION: Synthetic construct

<400> SEQUENCE: 17

Met Ala Trp Val Trp Thr Leu Leu Phe Leu Met Ala Ala Ala Gln Ser
1               5                   10                  15

Ile Gln Ala His Arg Arg Cys Asn Pro Asn Asn Lys Lys Arg Gly Gly
            20                  25                  30

Gly Gly Ser Glu Trp Ile Lys Gln Arg Pro Gly Gln Gly Leu Glu Trp
        35                  40                  45

Ile Gly Val Ile His Pro Gly Asn Gly Gly Thr Asn Tyr Asn Glu Asn
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Ser Asp Asp Ser Ala Val Tyr Phe
                85                  90                  95

Cys Ala Ser Gly Asn Asp Gly Ser Tyr Trp Gly Gln Gly Thr Thr Val
            100                 105                 110

Thr Val Ser Ser Gly Gly Gly Gly Ser Gly Lys Gly Gly Ser Gly Gly
        115                 120                 125

Gly Gly Ser Gly Gly Gly Gly Ser Asp Ile Glu Leu Thr Gln Ser Pro
    130                 135                 140

Ser Ser Leu Thr Val Thr Ala Gly Glu Lys Val Thr Met Ser Cys Lys
145                 150                 155                 160

Ser Ser Gln Ser Leu Leu Asn Ser Gly Asp Gln Lys Ile Tyr Leu Thr
                165                 170                 175

Trp Tyr Gln Gln Lys Pro Gly Gln Pro Pro Lys Leu Leu Ile Tyr Trp
            180                 185                 190

Ala Ser Thr Arg Glu Ser Gly Val Pro Asp Arg Phe Thr Gly Ser Val
        195                 200                 205

Ser Gly Thr Asp Phe Thr Leu Thr Ile Ser Ser Val Gln Ala Glu Asp
    210                 215                 220
```

```
Leu Ala Val Tyr Tyr Cys Gln Asn Asp Tyr Asn Tyr Pro Tyr Thr Phe
225                 230                 235                 240

Gly Gly Gly Thr Lys Leu Glu Ile Lys Arg Gly Ser Glu Asn Leu Tyr
                245                 250                 255

Phe Gln Gly Gly Ser Gly Lys Pro Ile Pro Asn Pro Leu Leu Gly Leu
            260                 265                 270

Asp Ser Thr Gly Gly Ser Gly Gly Ser His His His His His His
        275                 280                 285


<210> SEQ ID NO 18
<211> LENGTH: 290
<212> TYPE: PRT
<213> ORGANISM: Artificial Sequence
<220> FEATURE:
<223> OTHER INFORMATION: Synthetic construct

<400> SEQUENCE: 18

Met Ala Trp Val Trp Thr Leu Leu Phe Leu Met Ala Ala Ala Gln Ser
1               5                   10                  15

Ile Gln Ala Val Ser Arg Arg Arg Arg Arg Arg Gly Gly Arg Arg Arg
            20                  25                  30

Arg Gly Gly Gly Gly Ser Glu Trp Ile Lys Gln Arg Pro Gly Gln Gly
        35                  40                  45

Leu Glu Trp Ile Gly Val Ile His Pro Gly Asn Gly Gly Thr Asn Tyr
    50                  55                  60

Asn Glu Asn Phe Lys Gly Lys Ala Thr Leu Thr Ala Asp Lys Ser Ser
65                  70                  75                  80

Ser Thr Ala Tyr Met Gln Leu Ser Ser Leu Thr Ser Asp Asp Ser Ala
                85                  90                  95

Val Tyr Phe Cys Ala Ser Gly Asn Asp Gly Ser Tyr Trp Gly Gln Gly
            100                 105                 110

Thr Thr Val Thr Val Ser Ser Gly Gly Gly Gly Ser Gly Lys Gly Gly
        115                 120                 125

Ser Gly Gly Gly Gly Ser Gly Gly Gly Gly Ser Asp Ile Glu Leu Thr
    130                 135                 140

Gln Ser Pro Ser Ser Leu Thr Val Thr Ala Gly Glu Lys Val Thr Met
145                 150                 155                 160

Ser Cys Lys Ser Ser Gln Ser Leu Leu Asn Ser Gly Asp Gln Lys Ile
                165                 170                 175

Tyr Leu Thr Trp Tyr Gln Gln Lys Pro Gly Gln Pro Pro Lys Leu Leu
            180                 185                 190

Ile Tyr Trp Ala Ser Thr Arg Glu Ser Gly Val Pro Asp Arg Phe Thr
        195                 200                 205

Gly Ser Val Ser Gly Thr Asp Phe Thr Leu Thr Ile Ser Ser Val Gln
    210                 215                 220

Ala Glu Asp Leu Ala Val Tyr Tyr Cys Gln Asn Asp Tyr Asn Tyr Pro
225                 230                 235                 240

Tyr Thr Phe Gly Gly Gly Thr Lys Leu Glu Ile Lys Arg Gly Ser Glu
                245                 250                 255

Asn Leu Tyr Phe Gln Gly Gly Ser Gly Lys Pro Ile Pro Asn Pro Leu
            260                 265                 270

Leu Gly Leu Asp Ser Thr Gly Gly Ser Gly Gly Ser His His His His
        275                 280                 285

His His
    290
```

<210> SEQ ID NO 19
<211> LENGTH: 291
<212> TYPE: PRT
<213> ORGANISM: Artificial Sequence
<220> FEATURE:
<223> OTHER INFORMATION: Synthetic construct

<400> SEQUENCE: 19

```
Met Ala Trp Val Trp Thr Leu Leu Phe Leu Met Ala Ala Ala Gln Ser
1               5                   10                  15

Ile Gln Ala Gly Lys Cys Ser Thr Arg Gly Arg Lys Cys Cys Arg Arg
            20                  25                  30

Lys Lys Gly Gly Gly Gly Ser Glu Trp Ile Lys Gln Arg Pro Gly Gln
        35                  40                  45

Gly Leu Glu Trp Ile Gly Val Ile His Pro Gly Asn Gly Gly Thr Asn
    50                  55                  60

Tyr Asn Glu Asn Phe Lys Gly Lys Ala Thr Leu Thr Ala Asp Lys Ser
65                  70                  75                  80

Ser Ser Thr Ala Tyr Met Gln Leu Ser Ser Leu Thr Ser Asp Asp Ser
                85                  90                  95

Ala Val Tyr Phe Cys Ala Ser Gly Asn Asp Gly Ser Tyr Trp Gly Gln
            100                 105                 110

Gly Thr Thr Val Thr Val Ser Ser Gly Gly Gly Gly Ser Gly Lys Gly
        115                 120                 125

Gly Ser Gly Gly Gly Gly Ser Gly Gly Gly Gly Ser Asp Ile Glu Leu
    130                 135                 140

Thr Gln Ser Pro Ser Ser Leu Thr Val Thr Ala Gly Glu Lys Val Thr
145                 150                 155                 160

Met Ser Cys Lys Ser Ser Gln Ser Leu Leu Asn Ser Gly Asp Gln Lys
                165                 170                 175

Ile Tyr Leu Thr Trp Tyr Gln Gln Lys Pro Gly Gln Pro Pro Lys Leu
            180                 185                 190

Leu Ile Tyr Trp Ala Ser Thr Arg Glu Ser Gly Val Pro Asp Arg Phe
        195                 200                 205

Thr Gly Ser Val Ser Gly Thr Asp Phe Thr Leu Thr Ile Ser Ser Val
    210                 215                 220

Gln Ala Glu Asp Leu Ala Val Tyr Tyr Cys Gln Asn Asp Tyr Asn Tyr
225                 230                 235                 240

Pro Tyr Thr Phe Gly Gly Gly Thr Lys Leu Glu Ile Lys Arg Gly Ser
                245                 250                 255

Glu Asn Leu Tyr Phe Gln Gly Gly Ser Gly Lys Pro Ile Pro Asn Pro
            260                 265                 270

Leu Leu Gly Leu Asp Ser Thr Gly Gly Ser Gly Gly Ser His His His
        275                 280                 285

His His His
    290
```

<210> SEQ ID NO 20
<211> LENGTH: 270
<212> TYPE: PRT
<213> ORGANISM: Artificial Sequence
<220> FEATURE:
<223> OTHER INFORMATION: Synthetic construct

<400> SEQUENCE: 20

```
Met Ala Gln Val Lys Leu Gln Glu Ser Gly Pro Glu Leu Val Arg Pro
```

-continued

```
1               5                   10                  15

Gly Thr Ser Val Lys Val Ser Cys Lys Ala Ser Gly Tyr Ala Phe Thr
            20                  25                  30

Asn Tyr Leu Ile Glu Trp Ile Lys Gln Arg Pro Gly Gln Gly Leu Glu
        35                  40                  45

Trp Ile Gly Val Ile His Pro Gly Asn Gly Gly Thr Asn Tyr Asn Glu
    50                  55                  60

Asn Phe Lys Gly Lys Ala Thr Leu Thr Ala Asp Lys Ser Ser Ser Thr
65                  70                  75                  80

Ala Tyr Met Gln Leu Ser Ser Leu Thr Ser Asp Asp Ser Ala Val Tyr
                85                  90                  95

Phe Cys Ala Ser Gly Asn Asp Gly Ser Tyr Trp Gly Gln Gly Thr Thr
            100                 105                 110

Val Thr Val Ser Ser Gly Gly Gly Gly Ser Gly Gly Gly Gly Ser Gly
        115                 120                 125

Gly Gly Gly Ser Asp Ile Glu Leu Thr Gln Ser Pro Ser Ser Leu Thr
    130                 135                 140

Val Thr Ala Gly Glu Lys Val Thr Met Ser Cys Lys Ser Ser Gln Ser
145                 150                 155                 160

Leu Leu Asn Ser Gly Asp Gln Lys Ile Tyr Leu Thr Trp Tyr Gln Gln
                165                 170                 175

Lys Pro Gly Gln Pro Pro Lys Leu Leu Ile Tyr Trp Ala Ser Thr Arg
            180                 185                 190

Glu Ser Gly Val Pro Asp Arg Phe Thr Gly Ser Val Ser Gly Thr Asp
        195                 200                 205

Phe Thr Leu Thr Ile Ser Ser Val Gln Ala Glu Asp Leu Ala Val Tyr
    210                 215                 220

Tyr Cys Gln Asn Asp Tyr Asn Tyr Pro Tyr Thr Phe Gly Gly Gly Thr
225                 230                 235                 240

Lys Gly Gly Gly Gly Ser His Arg Arg Cys Asn Lys Asn Asn Lys Lys
                245                 250                 255

Arg Leu Glu Ile Lys Arg Leu Glu His His His His His His
            260                 265                 270


<210> SEQ ID NO 21
<211> LENGTH: 270
<212> TYPE: PRT
<213> ORGANISM: Artificial Sequence
<220> FEATURE:
<223> OTHER INFORMATION: Synthetic construct

<400> SEQUENCE: 21

Met Ala Gln Val Lys Leu Gln Glu Ser Gly Pro Glu Leu Val Arg Pro
1               5                   10                  15

Gly Thr Ser Val Lys Val Ser Cys Lys Ala Ser Gly Tyr Ala Phe Thr
            20                  25                  30

Asn Tyr Leu Ile Glu Trp Ile Lys Gln Arg Pro Gly Gln Gly Leu Glu
        35                  40                  45

Trp Ile Gly Val Ile His Pro Gly Asn Gly Gly Thr Asn Tyr Asn Glu
    50                  55                  60

Asn Phe Lys Gly Lys Ala Thr Leu Thr Ala Asp Lys Ser Ser Ser Thr
65                  70                  75                  80

Ala Tyr Met Gln Leu Ser Ser Leu Thr Ser Asp Asp Ser Ala Val Tyr
                85                  90                  95

Phe Cys Ala Ser Gly Asn Asp Gly Ser Tyr Trp Gly Gln Gly Thr Thr
```

-continued

```
            100                 105                 110

Val Thr Val Ser Ser Gly Gly Gly Gly Ser Gly Gly Gly Gly Ser Gly
        115                 120                 125

Gly Gly Gly Ser Asp Ile Glu Leu Thr Gln Ser Pro Ser Ser Leu Thr
    130                 135                 140

Val Thr Ala Gly Glu Lys Val Thr Met Ser Cys Lys Ser Ser Gln Ser
145                 150                 155                 160

Leu Leu Asn Ser Gly Asp Gln Lys Ile Tyr Leu Thr Trp Tyr Gln Gln
                165                 170                 175

Lys Pro Gly Gln Pro Pro Lys Leu Leu Ile Tyr Trp Ala Ser Thr Arg
            180                 185                 190

Glu Ser Gly Val Pro Asp Arg Phe Thr Gly Ser Val Ser Gly Thr Asp
        195                 200                 205

Phe Thr Leu Thr Ile Ser Ser Val Gln Ala Glu Asp Leu Ala Val Tyr
    210                 215                 220

Tyr Cys Gln Asn Asp Tyr Asn Tyr Pro Tyr Thr Phe Gly Gly Gly Thr
225                 230                 235                 240

Lys Gly Gly Gly Gly Ser His Arg Arg Cys Asn Pro Asn Asn Lys Lys
                245                 250                 255

Arg Leu Glu Ile Lys Arg Leu Glu His His His His His His
            260                 265                 270


<210> SEQ ID NO 22
<211> LENGTH: 273
<212> TYPE: PRT
<213> ORGANISM: Artificial Sequence
<220> FEATURE:
<223> OTHER INFORMATION: Synthetic construct

<400> SEQUENCE: 22

Met Ala Gln Val Lys Leu Gln Glu Ser Gly Pro Glu Leu Val Arg Pro
1               5                   10                  15

Gly Thr Ser Val Lys Val Ser Cys Lys Ala Ser Gly Tyr Ala Phe Thr
            20                  25                  30

Asn Tyr Leu Ile Glu Trp Ile Lys Gln Arg Pro Gly Gln Gly Leu Glu
        35                  40                  45

Trp Ile Gly Val Ile His Pro Gly Asn Gly Gly Thr Asn Tyr Asn Glu
    50                  55                  60

Asn Phe Lys Gly Lys Ala Thr Leu Thr Ala Asp Lys Ser Ser Ser Thr
65                  70                  75                  80

Ala Tyr Met Gln Leu Ser Ser Leu Thr Ser Asp Asp Ser Ala Val Tyr
                85                  90                  95

Phe Cys Ala Ser Gly Asn Asp Gly Ser Tyr Trp Gly Gln Gly Thr Thr
            100                 105                 110

Val Thr Val Ser Ser Gly Gly Gly Gly Ser Gly Gly Gly Gly Ser Gly
        115                 120                 125

Gly Gly Gly Ser Asp Ile Glu Leu Thr Gln Ser Pro Ser Ser Leu Thr
    130                 135                 140

Val Thr Ala Gly Glu Lys Val Thr Met Ser Cys Lys Ser Ser Gln Ser
145                 150                 155                 160

Leu Leu Asn Ser Gly Asp Gln Lys Ile Tyr Leu Thr Trp Tyr Gln Gln
                165                 170                 175

Lys Pro Gly Gln Pro Pro Lys Leu Leu Ile Tyr Trp Ala Ser Thr Arg
            180                 185                 190

Glu Ser Gly Val Pro Asp Arg Phe Thr Gly Ser Val Ser Gly Thr Asp
```

```
        195                 200                 205

Phe Thr Leu Thr Ile Ser Ser Val Gln Ala Glu Asp Leu Ala Val Tyr
    210                 215                 220

Tyr Cys Gln Asn Asp Tyr Asn Tyr Pro Tyr Thr Phe Gly Gly Gly Thr
225                 230                 235                 240

Lys Gly Gly Gly Gly Ser Val Ser Arg Arg Arg Arg Arg Arg Gly Gly
                245                 250                 255

Arg Arg Arg Arg Leu Glu Ile Lys Arg Leu Glu His His His His His
            260                 265                 270

His


<210> SEQ ID NO 23
<211> LENGTH: 274
<212> TYPE: PRT
<213> ORGANISM: Artificial Sequence
<220> FEATURE:
<223> OTHER INFORMATION: Synthetic construct

<400> SEQUENCE: 23

Met Ala Gln Val Lys Leu Gln Glu Ser Gly Pro Glu Leu Val Arg Pro
1               5                   10                  15

Gly Thr Ser Val Lys Val Ser Cys Lys Ala Ser Gly Tyr Ala Phe Thr
            20                  25                  30

Asn Tyr Leu Ile Glu Trp Ile Lys Gln Arg Pro Gly Gln Gly Leu Glu
        35                  40                  45

Trp Ile Gly Val Ile His Pro Gly Asn Gly Gly Thr Asn Tyr Asn Glu
    50                  55                  60

Asn Phe Lys Gly Lys Ala Thr Leu Thr Ala Asp Lys Ser Ser Ser Thr
65                  70                  75                  80

Ala Tyr Met Gln Leu Ser Ser Leu Thr Ser Asp Asp Ser Ala Val Tyr
                85                  90                  95

Phe Cys Ala Ser Gly Asn Asp Gly Ser Tyr Trp Gly Gln Gly Thr Thr
            100                 105                 110

Val Thr Val Ser Ser Gly Gly Gly Gly Ser Gly Gly Gly Gly Ser Gly
        115                 120                 125

Gly Gly Gly Ser Asp Ile Glu Leu Thr Gln Ser Pro Ser Ser Leu Thr
    130                 135                 140

Val Thr Ala Gly Glu Lys Val Thr Met Ser Cys Lys Ser Ser Gln Ser
145                 150                 155                 160

Leu Leu Asn Ser Gly Asp Gln Lys Ile Tyr Leu Thr Trp Tyr Gln Gln
                165                 170                 175

Lys Pro Gly Gln Pro Pro Lys Leu Leu Ile Tyr Trp Ala Ser Thr Arg
            180                 185                 190

Glu Ser Gly Val Pro Asp Arg Phe Thr Gly Ser Val Ser Gly Thr Asp
        195                 200                 205

Phe Thr Leu Thr Ile Ser Ser Val Gln Ala Glu Asp Leu Ala Val Tyr
    210                 215                 220

Tyr Cys Gln Asn Asp Tyr Asn Tyr Pro Tyr Thr Phe Gly Gly Gly Thr
225                 230                 235                 240

Lys Gly Gly Gly Gly Ser Gly Lys Cys Ser Thr Arg Gly Arg Lys Cys
                245                 250                 255

Cys Arg Arg Lys Lys Leu Glu Ile Lys Arg Leu Glu His His His His
            260                 265                 270

His His
```

<210> SEQ ID NO 24
<211> LENGTH: 275
<212> TYPE: PRT
<213> ORGANISM: Artificial Sequence
<220> FEATURE:
<223> OTHER INFORMATION: Synthetic construct

<400> SEQUENCE: 24

Met Ala Gln Val Lys Leu Gln Glu Ser Gly Pro Glu Leu Val Arg Pro
1 5 10 15

Gly Thr Ser Val Lys Val Ser Cys Lys Ala Ser Gly Tyr Ala Phe Thr
20 25 30

Asn Tyr Leu Ile His Arg Arg Cys Asn Lys Asn Asn Lys Lys Arg Gly
35 40 45

Gly Gly Gly Ser Glu Trp Ile Lys Gln Arg Pro Gly Gln Gly Leu Glu
50 55 60

Trp Ile Gly Val Ile His Pro Gly Asn Gly Gly Thr Asn Tyr Asn Glu
65 70 75 80

Asn Phe Lys Gly Lys Ala Thr Leu Thr Ala Asp Lys Ser Ser Ser Thr
85 90 95

Ala Tyr Met Gln Leu Ser Ser Leu Thr Ser Asp Asp Ser Ala Val Tyr
100 105 110

Phe Cys Ala Ser Gly Asn Asp Gly Ser Tyr Trp Gly Gln Gly Thr Thr
115 120 125

Val Thr Val Ser Ser Gly Gly Gly Gly Ser Gly Lys Gly Gly Ser Gly
130 135 140

Gly Gly Gly Ser Gly Gly Gly Gly Ser Asp Ile Glu Leu Thr Gln Ser
145 150 155 160

Pro Ser Ser Leu Thr Val Thr Ala Gly Glu Lys Val Thr Met Ser Cys
165 170 175

Lys Ser Ser Gln Ser Leu Leu Asn Ser Gly Asp Gln Lys Ile Tyr Leu
180 185 190

Thr Trp Tyr Gln Gln Lys Pro Gly Gln Pro Pro Lys Leu Leu Ile Tyr
195 200 205

Trp Ala Ser Thr Arg Glu Ser Gly Val Pro Asp Arg Phe Thr Gly Ser
210 215 220

Val Ser Gly Thr Asp Phe Thr Leu Thr Ile Ser Ser Val Gln Ala Glu
225 230 235 240

Asp Leu Ala Val Tyr Tyr Cys Gln Asn Asp Tyr Asn Tyr Pro Tyr Thr
245 250 255

Phe Gly Gly Gly Thr Lys Leu Glu Ile Lys Arg Leu Glu His His His
260 265 270

His His His
275

<210> SEQ ID NO 25
<211> LENGTH: 275
<212> TYPE: PRT
<213> ORGANISM: Artificial Sequence
<220> FEATURE:
<223> OTHER INFORMATION: Synthetic construct

<400> SEQUENCE: 25

Met Ala Gln Val Lys Leu Gln Glu Ser Gly Pro Glu Leu Val Arg Pro
1 5 10 15

Gly Thr Ser Val Lys Val Ser Cys Lys Ala Ser Gly Tyr Ala Phe Thr
20 25 30

Asn Tyr Leu Ile His Arg Arg Cys Asn Pro Asn Asn Lys Lys Arg Gly
35 40 45

Gly Gly Gly Ser Glu Trp Ile Lys Gln Arg Pro Gly Gln Gly Leu Glu
50 55 60

Trp Ile Gly Val Ile His Pro Gly Asn Gly Gly Thr Asn Tyr Asn Glu
65 70 75 80

Asn Phe Lys Gly Lys Ala Thr Leu Thr Ala Asp Lys Ser Ser Ser Thr
85 90 95

Ala Tyr Met Gln Leu Ser Ser Leu Thr Ser Asp Asp Ser Ala Val Tyr
100 105 110

Phe Cys Ala Ser Gly Asn Asp Gly Ser Tyr Trp Gly Gln Gly Thr Thr
115 120 125

Val Thr Val Ser Ser Gly Gly Gly Gly Ser Gly Lys Gly Gly Ser Gly
130 135 140

Gly Gly Gly Ser Gly Gly Gly Gly Ser Asp Ile Glu Leu Thr Gln Ser
145 150 155 160

Pro Ser Ser Leu Thr Val Thr Ala Gly Glu Lys Val Thr Met Ser Cys
165 170 175

Lys Ser Ser Gln Ser Leu Leu Asn Ser Gly Asp Gln Lys Ile Tyr Leu
180 185 190

Thr Trp Tyr Gln Gln Lys Pro Gly Gln Pro Pro Lys Leu Leu Ile Tyr
195 200 205

Trp Ala Ser Thr Arg Glu Ser Gly Val Pro Asp Arg Phe Thr Gly Ser
210 215 220

Val Ser Gly Thr Asp Phe Thr Leu Thr Ile Ser Ser Val Gln Ala Glu
225 230 235 240

Asp Leu Ala Val Tyr Tyr Cys Gln Asn Asp Tyr Asn Tyr Pro Tyr Thr
245 250 255

Phe Gly Gly Gly Thr Lys Leu Glu Ile Lys Arg Leu Glu His His His
260 265 270

His His His
275

<210> SEQ ID NO 26
<211> LENGTH: 278
<212> TYPE: PRT
<213> ORGANISM: Artificial Sequence
<220> FEATURE:
<223> OTHER INFORMATION: Synthetic construct

<400> SEQUENCE: 26

Met Ala Gln Val Lys Leu Gln Glu Ser Gly Pro Glu Leu Val Arg Pro
1 5 10 15

Gly Thr Ser Val Lys Val Ser Cys Lys Ala Ser Gly Tyr Ala Phe Thr
20 25 30

Asn Tyr Leu Ile Val Ser Arg Arg Arg Arg Arg Arg Gly Gly Arg Arg
35 40 45

Arg Arg Gly Gly Gly Gly Ser Glu Trp Ile Lys Gln Arg Pro Gly Gln
50 55 60

Gly Leu Glu Trp Ile Gly Val Ile His Pro Gly Asn Gly Gly Thr Asn
65 70 75 80

Tyr Asn Glu Asn Phe Lys Gly Lys Ala Thr Leu Thr Ala Asp Lys Ser
85 90 95

Ser Ser Thr Ala Tyr Met Gln Leu Ser Ser Leu Thr Ser Asp Asp Ser
100 105 110

-continued

Ala Val Tyr Phe Cys Ala Ser Gly Asn Asp Gly Ser Tyr Trp Gly Gln
115 120 125

Gly Thr Thr Val Thr Val Ser Ser Gly Gly Gly Gly Ser Gly Lys Gly
130 135 140

Gly Ser Gly Gly Gly Gly Ser Gly Gly Gly Gly Ser Asp Ile Glu Leu
145 150 155 160

Thr Gln Ser Pro Ser Ser Leu Thr Val Thr Ala Gly Glu Lys Val Thr
165 170 175

Met Ser Cys Lys Ser Ser Gln Ser Leu Leu Asn Ser Gly Asp Gln Lys
180 185 190

Ile Tyr Leu Thr Trp Tyr Gln Gln Lys Pro Gly Gln Pro Pro Lys Leu
195 200 205

Leu Ile Tyr Trp Ala Ser Thr Arg Glu Ser Gly Val Pro Asp Arg Phe
210 215 220

Thr Gly Ser Val Ser Gly Thr Asp Phe Thr Leu Thr Ile Ser Ser Val
225 230 235 240

Gln Ala Glu Asp Leu Ala Val Tyr Tyr Cys Gln Asn Asp Tyr Asn Tyr
245 250 255

Pro Tyr Thr Phe Gly Gly Gly Thr Lys Leu Glu Ile Lys Arg Leu Glu
260 265 270

His His His His His His
275

<210> SEQ ID NO 27
<211> LENGTH: 280
<212> TYPE: PRT
<213> ORGANISM: Artificial Sequence
<220> FEATURE:
<223> OTHER INFORMATION: Synthetic construct

<400> SEQUENCE: 27

Met Ala Gln Val Lys Leu Gln Glu Ser Gly Pro Glu Leu Val Arg Pro
1 5 10 15

Gly Thr Ser Val Lys Val Ser Cys Lys Ala Ser Gly Tyr Ala Phe Thr
20 25 30

Asn Tyr Leu Ile Gly Lys Cys Ser Thr Arg Gly Arg Lys Cys Cys Arg
35 40 45

Arg Lys Lys Gly Gly Gly Gly Ser Glu Trp Ile Lys Gln Arg Pro Gly
50 55 60

Gln Gly Leu Glu Trp Ile Gly Val Ile His Pro Gly Asn Gly Gly Thr
65 70 75 80

Asn Tyr Asn Glu Asn Phe Lys Gly Lys Ala Thr Leu Thr Ala Asp Lys
85 90 95

Ser Ser Ser Thr Ala Tyr Met Gln Leu Ser Ser Leu Thr Ser Asp Asp
100 105 110

Ser Ala Val Tyr Phe Cys Ala Ser Gly Asn Asp Gly Ser Tyr Trp Gly
115 120 125

Gln Gly Thr Thr Val Thr Val Ser Ser Gly Gly Gly Gly Ser Gly Lys
130 135 140

Gly Gly Ser Gly Gly Gly Gly Ser Gly Gly Gly Gly Ser Asp Ile Glu
145 150 155 160

Leu Thr Gln Ser Pro Ser Ser Leu Thr Val Thr Ala Gly Glu Lys Val
165 170 175

Thr Met Ser Cys Lys Ser Ser Gln Ser Leu Leu Asn Ser Gly Asp Gln
180 185 190

-continued

```
Lys Ile Tyr Leu Thr Trp Tyr Gln Gln Lys Pro Gly Gln Pro Pro Lys
        195                 200                 205

Leu Leu Ile Tyr Trp Ala Ser Thr Arg Glu Ser Gly Val Pro Asp Arg
    210                 215                 220

Phe Thr Gly Ser Val Ser Gly Thr Asp Phe Thr Leu Thr Ile Ser Ser
225                 230                 235                 240

Val Gln Ala Glu Asp Leu Ala Val Tyr Tyr Cys Gln Asn Asp Tyr Asn
                245                 250                 255

Tyr Pro Tyr Thr Phe Gly Gly Gly Thr Lys Leu Glu Ile Lys Arg Leu
            260                 265                 270

Glu His His His His His His His
        275                 280


<210> SEQ ID NO 28
<211> LENGTH: 287
<212> TYPE: PRT
<213> ORGANISM: Artificial Sequence
<220> FEATURE:
<223> OTHER INFORMATION: Synthetic construct

<400> SEQUENCE: 28

Met Ala Trp Val Trp Thr Leu Leu Phe Leu Met Ala Ala Ala Gln Ser
1               5                   10                  15

Ile Gln Ala Glu Trp Ile Lys Gln Arg Pro Gly Gln Gly Leu Glu Trp
            20                  25                  30

Ile Gly Val Ile His Pro Gly Asn Gly Gly Thr Asn Tyr Asn Glu Asn
        35                  40                  45

Phe Lys Gly Lys Ala Thr Leu Thr Ala Asp Lys Ser Ser Ser Thr Ala
    50                  55                  60

Tyr Met Gln Leu Ser Ser Leu Thr Ser Asp Asp Ser Ala Val Tyr Phe
65                  70                  75                  80

Cys Ala Ser Gly Asn Asp Gly Ser Tyr Trp Gly Gln Gly Thr Thr Val
                85                  90                  95

Thr Val Ser Ser Gly Gly Gly Gly Ser Gly Lys Gly Gly Ser Gly Gly
            100                 105                 110

Gly Gly Ser Gly Gly Gly Gly Ser Asp Ile Glu Leu Thr Gln Ser Pro
        115                 120                 125

Ser Ser Leu Thr Val Thr Ala Gly Glu Lys Val Thr Met Ser Cys Lys
    130                 135                 140

Ser Ser Gln Ser Leu Leu Asn Ser Gly Asp Gln Lys Ile Tyr Leu Thr
145                 150                 155                 160

Trp Tyr Gln Gln Lys Pro Gly Gln Pro Pro Lys Leu Leu Ile Tyr Trp
                165                 170                 175

Ala Ser Thr Arg Glu Ser Gly Val Pro Asp Arg Phe Thr Gly Ser Val
            180                 185                 190

Ser Gly Thr Asp Phe Thr Leu Thr Ile Ser Ser Val Gln Ala Glu Asp
        195                 200                 205

Leu Ala Val Tyr Tyr Cys Gln Asn Asp Tyr Asn Tyr Pro Tyr Thr Phe
    210                 215                 220

Gly Gly Gly Thr Lys Gly Gly Gly Gly Ser His Arg Arg Cys Asn Lys
225                 230                 235                 240

Asn Asn Lys Lys Arg Leu Glu Ile Lys Arg Gly Ser Glu Asn Leu Tyr
                245                 250                 255

Phe Gln Gly Gly Ser Gly Lys Pro Ile Pro Asn Pro Leu Leu Gly Leu
            260                 265                 270
```

```
Asp Ser Thr Gly Gly Ser Gly Gly Ser His His His His His His
        275                 280                 285


<210> SEQ ID NO 29
<211> LENGTH: 287
<212> TYPE: PRT
<213> ORGANISM: Artificial Sequence
<220> FEATURE:
<223> OTHER INFORMATION: Synthetic construct

<400> SEQUENCE: 29

Met Ala Trp Val Trp Thr Leu Leu Phe Leu Met Ala Ala Ala Gln Ser
1               5                   10                  15

Ile Gln Ala Glu Trp Ile Lys Gln Arg Pro Gly Gln Gly Leu Glu Trp
            20                  25                  30

Ile Gly Val Ile His Pro Gly Asn Gly Gly Thr Asn Tyr Asn Glu Asn
        35                  40                  45

Phe Lys Gly Lys Ala Thr Leu Thr Ala Asp Lys Ser Ser Ser Thr Ala
    50                  55                  60

Tyr Met Gln Leu Ser Ser Leu Thr Ser Asp Asp Ser Ala Val Tyr Phe
65                  70                  75                  80

Cys Ala Ser Gly Asn Asp Gly Ser Tyr Trp Gly Gln Gly Thr Thr Val
                85                  90                  95

Thr Val Ser Ser Gly Gly Gly Gly Ser Gly Lys Gly Gly Ser Gly Gly
            100                 105                 110

Gly Gly Ser Gly Gly Gly Gly Ser Asp Ile Glu Leu Thr Gln Ser Pro
        115                 120                 125

Ser Ser Leu Thr Val Thr Ala Gly Glu Lys Val Thr Met Ser Cys Lys
    130                 135                 140

Ser Ser Gln Ser Leu Leu Asn Ser Gly Asp Gln Lys Ile Tyr Leu Thr
145                 150                 155                 160

Trp Tyr Gln Gln Lys Pro Gly Gln Pro Pro Lys Leu Leu Ile Tyr Trp
                165                 170                 175

Ala Ser Thr Arg Glu Ser Gly Val Pro Asp Arg Phe Thr Gly Ser Val
            180                 185                 190

Ser Gly Thr Asp Phe Thr Leu Thr Ile Ser Ser Val Gln Ala Glu Asp
        195                 200                 205

Leu Ala Val Tyr Tyr Cys Gln Asn Asp Tyr Asn Tyr Pro Tyr Thr Phe
    210                 215                 220

Gly Gly Gly Thr Lys Gly Gly Gly Gly Ser His Arg Arg Cys Asn Pro
225                 230                 235                 240

Asn Asn Lys Lys Arg Leu Glu Ile Lys Arg Gly Ser Glu Asn Leu Tyr
                245                 250                 255

Phe Gln Gly Gly Ser Gly Lys Pro Ile Pro Asn Pro Leu Leu Gly Leu
            260                 265                 270

Asp Ser Thr Gly Gly Ser Gly Gly Ser His His His His His His
        275                 280                 285


<210> SEQ ID NO 30
<211> LENGTH: 290
<212> TYPE: PRT
<213> ORGANISM: Artificial Sequence
<220> FEATURE:
<223> OTHER INFORMATION: Synthetic construct

<400> SEQUENCE: 30

Met Ala Trp Val Trp Thr Leu Leu Phe Leu Met Ala Ala Ala Gln Ser
```

-continued

```
1               5                   10                  15

Ile Gln Ala Glu Trp Ile Lys Gln Arg Pro Gly Gln Gly Leu Glu Trp
            20                  25                  30

Ile Gly Val Ile His Pro Gly Asn Gly Gly Thr Asn Tyr Asn Glu Asn
        35                  40                  45

Phe Lys Gly Lys Ala Thr Leu Thr Ala Asp Lys Ser Ser Ser Thr Ala
    50                  55                  60

Tyr Met Gln Leu Ser Ser Leu Thr Ser Asp Asp Ser Ala Val Tyr Phe
65                  70                  75                  80

Cys Ala Ser Gly Asn Asp Gly Ser Tyr Trp Gly Gln Gly Thr Thr Val
                85                  90                  95

Thr Val Ser Ser Gly Gly Gly Gly Ser Gly Lys Gly Gly Ser Gly Gly
            100                 105                 110

Gly Gly Ser Gly Gly Gly Gly Ser Asp Ile Glu Leu Thr Gln Ser Pro
        115                 120                 125

Ser Ser Leu Thr Val Thr Ala Gly Glu Lys Val Thr Met Ser Cys Lys
    130                 135                 140

Ser Ser Gln Ser Leu Leu Asn Ser Gly Asp Gln Lys Ile Tyr Leu Thr
145                 150                 155                 160

Trp Tyr Gln Gln Lys Pro Gly Gln Pro Pro Lys Leu Leu Ile Tyr Trp
                165                 170                 175

Ala Ser Thr Arg Glu Ser Gly Val Pro Asp Arg Phe Thr Gly Ser Val
            180                 185                 190

Ser Gly Thr Asp Phe Thr Leu Thr Ile Ser Ser Val Gln Ala Glu Asp
        195                 200                 205

Leu Ala Val Tyr Tyr Cys Gln Asn Asp Tyr Asn Tyr Pro Tyr Thr Phe
    210                 215                 220

Gly Gly Gly Thr Lys Gly Gly Gly Gly Ser Val Ser Arg Arg Arg Arg
225                 230                 235                 240

Arg Arg Gly Gly Arg Arg Arg Arg Leu Glu Ile Lys Arg Gly Ser Glu
                245                 250                 255

Asn Leu Tyr Phe Gln Gly Gly Ser Gly Lys Pro Ile Pro Asn Pro Leu
            260                 265                 270

Leu Gly Leu Asp Ser Thr Gly Gly Ser Gly Gly Ser His His His His
        275                 280                 285

His His
    290
```

```
<210> SEQ ID NO 31
<211> LENGTH: 291
<212> TYPE: PRT
<213> ORGANISM: Artificial Sequence
<220> FEATURE:
<223> OTHER INFORMATION: Synthetic construct

<400> SEQUENCE: 31

Met Ala Trp Val Trp Thr Leu Leu Phe Leu Met Ala Ala Ala Gln Ser
1               5                   10                  15

Ile Gln Ala Glu Trp Ile Lys Gln Arg Pro Gly Gln Gly Leu Glu Trp
            20                  25                  30

Ile Gly Val Ile His Pro Gly Asn Gly Gly Thr Asn Tyr Asn Glu Asn
        35                  40                  45

Phe Lys Gly Lys Ala Thr Leu Thr Ala Asp Lys Ser Ser Ser Thr Ala
    50                  55                  60

Tyr Met Gln Leu Ser Ser Leu Thr Ser Asp Asp Ser Ala Val Tyr Phe
```

```
65                  70                  75                  80

Cys Ala Ser Gly Asn Asp Gly Ser Tyr Trp Gly Gln Gly Thr Thr Val
                85                  90                  95

Thr Val Ser Ser Gly Gly Gly Gly Ser Gly Lys Gly Gly Ser Gly Gly
            100                 105                 110

Gly Gly Ser Gly Gly Gly Gly Ser Asp Ile Glu Leu Thr Gln Ser Pro
        115                 120                 125

Ser Ser Leu Thr Val Thr Ala Gly Glu Lys Val Thr Met Ser Cys Lys
    130                 135                 140

Ser Ser Gln Ser Leu Leu Asn Ser Gly Asp Gln Lys Ile Tyr Leu Thr
145                 150                 155                 160

Trp Tyr Gln Gln Lys Pro Gly Gln Pro Pro Lys Leu Leu Ile Tyr Trp
                165                 170                 175

Ala Ser Thr Arg Glu Ser Gly Val Pro Asp Arg Phe Thr Gly Ser Val
            180                 185                 190

Ser Gly Thr Asp Phe Thr Leu Thr Ile Ser Ser Val Gln Ala Glu Asp
        195                 200                 205

Leu Ala Val Tyr Tyr Cys Gln Asn Asp Tyr Asn Tyr Pro Tyr Thr Phe
    210                 215                 220

Gly Gly Gly Thr Lys Gly Gly Gly Gly Ser Gly Lys Cys Ser Thr Arg
225                 230                 235                 240

Gly Arg Lys Cys Cys Arg Arg Lys Lys Leu Glu Ile Lys Arg Gly Ser
                245                 250                 255

Glu Asn Leu Tyr Phe Gln Gly Gly Ser Gly Lys Pro Ile Pro Asn Pro
            260                 265                 270

Leu Leu Gly Leu Asp Ser Thr Gly Gly Ser Gly Gly Ser His His His
        275                 280                 285

His His His
    290
```

<210> SEQ ID NO 32
<211> LENGTH: 287
<212> TYPE: PRT
<213> ORGANISM: Artificial Sequence
<220> FEATURE:
<223> OTHER INFORMATION: Synthetic construct

<400> SEQUENCE: 32

```
Met Ala Trp Val Trp Thr Leu Leu Phe Leu Met Ala Ala Ala Gln Ser
1               5                   10                  15

Ile Gln Ala His Arg Arg Cys Asn Lys Asn Asn Lys Lys Arg Gly Gly
            20                  25                  30

Gly Gly Ser Glu Trp Ile Lys Gln Arg Pro Gly Gln Gly Leu Glu Trp
        35                  40                  45

Ile Gly Val Ile His Pro Gly Asn Gly Gly Thr Asn Tyr Asn Glu Asn
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Ser Asp Asp Ser Ala Val Tyr Phe
                85                  90                  95

Cys Ala Ser Gly Asn Asp Gly Ser Tyr Trp Gly Gln Gly Thr Thr Val
            100                 105                 110

Thr Val Ser Ser Gly Gly Gly Gly Ser Gly Lys Gly Gly Ser Gly Gly
        115                 120                 125

Gly Gly Ser Gly Gly Gly Gly Ser Asp Ile Glu Leu Thr Gln Ser Pro
```

```
    130                 135                 140

Ser Ser Leu Thr Val Thr Ala Gly Glu Lys Val Thr Met Ser Cys Lys
145                 150                 155                 160

Ser Ser Gln Ser Leu Leu Asn Ser Gly Asp Gln Lys Ile Tyr Leu Thr
                165                 170                 175

Trp Tyr Gln Gln Lys Pro Gly Gln Pro Pro Lys Leu Leu Ile Tyr Trp
            180                 185                 190

Ala Ser Thr Arg Glu Ser Gly Val Pro Asp Arg Phe Thr Gly Ser Val
        195                 200                 205

Ser Gly Thr Asp Phe Thr Leu Thr Ile Ser Ser Val Gln Ala Glu Asp
    210                 215                 220

Leu Ala Val Tyr Tyr Cys Gln Asn Asp Tyr Asn Tyr Pro Tyr Thr Phe
225                 230                 235                 240

Gly Gly Gly Thr Lys Leu Glu Ile Lys Arg Gly Ser Glu Asn Leu Tyr
                245                 250                 255

Phe Gln Gly Gly Ser Gly Lys Pro Ile Pro Asn Pro Leu Leu Gly Leu
            260                 265                 270

Asp Ser Thr Gly Gly Ser Gly Gly Ser His His His His His His
        275                 280                 285


<210> SEQ ID NO 33
<211> LENGTH: 287
<212> TYPE: PRT
<213> ORGANISM: Artificial Sequence
<220> FEATURE:
<223> OTHER INFORMATION: Synthetic construct

<400> SEQUENCE: 33

Met Ala Trp Val Trp Thr Leu Leu Phe Leu Met Ala Ala Ala Gln Ser
1               5                   10                  15

Ile Gln Ala His Arg Arg Cys Asn Pro Asn Asn Lys Lys Arg Gly Gly
            20                  25                  30

Gly Gly Ser Glu Trp Ile Lys Gln Arg Pro Gly Gln Gly Leu Glu Trp
        35                  40                  45

Ile Gly Val Ile His Pro Gly Asn Gly Gly Thr Asn Tyr Asn Glu Asn
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Ser Asp Asp Ser Ala Val Tyr Phe
                85                  90                  95

Cys Ala Ser Gly Asn Asp Gly Ser Tyr Trp Gly Gln Gly Thr Thr Val
            100                 105                 110

Thr Val Ser Ser Gly Gly Gly Gly Ser Gly Lys Gly Gly Ser Gly Gly
        115                 120                 125

Gly Gly Ser Gly Gly Gly Gly Ser Asp Ile Glu Leu Thr Gln Ser Pro
    130                 135                 140

Ser Ser Leu Thr Val Thr Ala Gly Glu Lys Val Thr Met Ser Cys Lys
145                 150                 155                 160

Ser Ser Gln Ser Leu Leu Asn Ser Gly Asp Gln Lys Ile Tyr Leu Thr
                165                 170                 175

Trp Tyr Gln Gln Lys Pro Gly Gln Pro Pro Lys Leu Leu Ile Tyr Trp
            180                 185                 190

Ala Ser Thr Arg Glu Ser Gly Val Pro Asp Arg Phe Thr Gly Ser Val
        195                 200                 205

Ser Gly Thr Asp Phe Thr Leu Thr Ile Ser Ser Val Gln Ala Glu Asp
```

-continued

```
    210                 215                 220

Leu Ala Val Tyr Tyr Cys Gln Asn Asp Tyr Asn Tyr Pro Tyr Thr Phe
225                 230                 235                 240

Gly Gly Gly Thr Lys Leu Glu Ile Lys Arg Gly Ser Glu Asn Leu Tyr
                245                 250                 255

Phe Gln Gly Gly Ser Gly Lys Pro Ile Pro Asn Pro Leu Leu Gly Leu
            260                 265                 270

Asp Ser Thr Gly Gly Ser Gly Gly Ser His His His His His His
        275                 280                 285


<210> SEQ ID NO 34
<211> LENGTH: 290
<212> TYPE: PRT
<213> ORGANISM: Artificial Sequence
<220> FEATURE:
<223> OTHER INFORMATION: Synthetic construct

<400> SEQUENCE: 34

Met Ala Trp Val Trp Thr Leu Leu Phe Leu Met Ala Ala Ala Gln Ser
1               5                   10                  15

Ile Gln Ala Val Ser Arg Arg Arg Arg Arg Arg Gly Gly Arg Arg Arg
            20                  25                  30

Arg Gly Gly Gly Gly Ser Glu Trp Ile Lys Gln Arg Pro Gly Gln Gly
        35                  40                  45

Leu Glu Trp Ile Gly Val Ile His Pro Gly Asn Gly Gly Thr Asn Tyr
    50                  55                  60

Asn Glu Asn Phe Lys Gly Lys Ala Thr Leu Thr Ala Asp Lys Ser Ser
65                  70                  75                  80

Ser Thr Ala Tyr Met Gln Leu Ser Ser Leu Thr Ser Asp Asp Ser Ala
                85                  90                  95

Val Tyr Phe Cys Ala Ser Gly Asn Asp Gly Ser Tyr Trp Gly Gln Gly
            100                 105                 110

Thr Thr Val Thr Val Ser Ser Gly Gly Gly Gly Ser Gly Lys Gly Gly
        115                 120                 125

Ser Gly Gly Gly Gly Ser Gly Gly Gly Gly Ser Asp Ile Glu Leu Thr
    130                 135                 140

Gln Ser Pro Ser Ser Leu Thr Val Thr Ala Gly Glu Lys Val Thr Met
145                 150                 155                 160

Ser Cys Lys Ser Ser Gln Ser Leu Leu Asn Ser Gly Asp Gln Lys Ile
                165                 170                 175

Tyr Leu Thr Trp Tyr Gln Gln Lys Pro Gly Gln Pro Pro Lys Leu Leu
            180                 185                 190

Ile Tyr Trp Ala Ser Thr Arg Glu Ser Gly Val Pro Asp Arg Phe Thr
        195                 200                 205

Gly Ser Val Ser Gly Thr Asp Phe Thr Leu Thr Ile Ser Ser Val Gln
    210                 215                 220

Ala Glu Asp Leu Ala Val Tyr Tyr Cys Gln Asn Asp Tyr Asn Tyr Pro
225                 230                 235                 240

Tyr Thr Phe Gly Gly Gly Thr Lys Leu Glu Ile Lys Arg Gly Ser Glu
                245                 250                 255

Asn Leu Tyr Phe Gln Gly Gly Ser Gly Lys Pro Ile Pro Asn Pro Leu
            260                 265                 270

Leu Gly Leu Asp Ser Thr Gly Gly Ser Gly Gly Ser His His His His
        275                 280                 285

His His
```

290

<210> SEQ ID NO 35
<211> LENGTH: 291
<212> TYPE: PRT
<213> ORGANISM: Artificial Sequence
<220> FEATURE:
<223> OTHER INFORMATION: Synthetic construct

<400> SEQUENCE: 35

```
Met Ala Trp Val Trp Thr Leu Leu Phe Leu Met Ala Ala Ala Gln Ser
1               5                   10                  15

Ile Gln Ala Gly Lys Cys Ser Thr Arg Gly Arg Lys Cys Cys Arg Arg
            20                  25                  30

Lys Lys Gly Gly Gly Gly Ser Glu Trp Ile Lys Gln Arg Pro Gly Gln
        35                  40                  45

Gly Leu Glu Trp Ile Gly Val Ile His Pro Gly Asn Gly Gly Thr Asn
    50                  55                  60

Tyr Asn Glu Asn Phe Lys Gly Lys Ala Thr Leu Thr Ala Asp Lys Ser
65                  70                  75                  80

Ser Ser Thr Ala Tyr Met Gln Leu Ser Ser Leu Thr Ser Asp Asp Ser
                85                  90                  95

Ala Val Tyr Phe Cys Ala Ser Gly Asn Asp Gly Ser Tyr Trp Gly Gln
            100                 105                 110

Gly Thr Thr Val Thr Val Ser Ser Gly Gly Gly Gly Ser Gly Lys Gly
        115                 120                 125

Gly Ser Gly Gly Gly Gly Ser Gly Gly Gly Gly Ser Asp Ile Glu Leu
    130                 135                 140

Thr Gln Ser Pro Ser Ser Leu Thr Val Thr Ala Gly Glu Lys Val Thr
145                 150                 155                 160

Met Ser Cys Lys Ser Ser Gln Ser Leu Leu Asn Ser Gly Asp Gln Lys
                165                 170                 175

Ile Tyr Leu Thr Trp Tyr Gln Gln Lys Pro Gly Gln Pro Pro Lys Leu
            180                 185                 190

Leu Ile Tyr Trp Ala Ser Thr Arg Glu Ser Gly Val Pro Asp Arg Phe
        195                 200                 205

Thr Gly Ser Val Ser Gly Thr Asp Phe Thr Leu Thr Ile Ser Ser Val
    210                 215                 220

Gln Ala Glu Asp Leu Ala Val Tyr Tyr Cys Gln Asn Asp Tyr Asn Tyr
225                 230                 235                 240

Pro Tyr Thr Phe Gly Gly Gly Thr Lys Leu Glu Ile Lys Arg Gly Ser
                245                 250                 255

Glu Asn Leu Tyr Phe Gln Gly Gly Ser Gly Lys Pro Ile Pro Asn Pro
            260                 265                 270

Leu Leu Gly Leu Asp Ser Thr Gly Gly Ser Gly Gly Ser His His His
        275                 280                 285

His His His
    290
```

<210> SEQ ID NO 36
<211> LENGTH: 270
<212> TYPE: PRT
<213> ORGANISM: Artificial Sequence
<220> FEATURE:
<223> OTHER INFORMATION: Synthetic construct

<400> SEQUENCE: 36

```
Met Ala Gln Val Lys Leu Gln Glu Ser Gly Pro Glu Leu Val Arg Pro
1               5                   10                  15

Gly Thr Ser Val Lys Val Ser Cys Lys Ala Ser Gly Tyr Ala Phe Thr
            20                  25                  30

Asn Tyr Leu Ile Glu Trp Ile Lys Gln Arg Pro Gly Gln Gly Leu Glu
        35                  40                  45

Trp Ile Gly Val Ile His Pro Gly Asn Gly Gly Thr Asn Tyr Asn Glu
    50                  55                  60

Asn Phe Lys Gly Lys Ala Thr Leu Thr Ala Asp Lys Ser Ser Ser Thr
65                  70                  75                  80

Ala Tyr Met Gln Leu Ser Ser Leu Thr Ser Asp Asp Ser Ala Val Tyr
                85                  90                  95

Phe Cys Ala Ser Gly Asn Asp Gly Ser Tyr Trp Gly Gln Gly Thr Thr
            100                 105                 110

Val Thr Val Ser Ser Gly Gly Gly Gly Ser Gly Gly Gly Gly Ser Gly
        115                 120                 125

Gly Gly Gly Ser Asp Ile Glu Leu Thr Gln Ser Pro Ser Ser Leu Thr
    130                 135                 140

Val Thr Ala Gly Glu Lys Val Thr Met Ser Cys Lys Ser Ser Gln Ser
145                 150                 155                 160

Leu Leu Asn Ser Gly Asp Gln Lys Ile Tyr Leu Thr Trp Tyr Gln Gln
                165                 170                 175

Lys Pro Gly Gln Pro Pro Lys Leu Leu Ile Tyr Trp Ala Ser Thr Arg
            180                 185                 190

Glu Ser Gly Val Pro Asp Arg Phe Thr Gly Ser Val Ser Gly Thr Asp
        195                 200                 205

Phe Thr Leu Thr Ile Ser Ser Val Gln Ala Glu Asp Leu Ala Val Tyr
    210                 215                 220

Tyr Cys Gln Asn Asp Tyr Asn Tyr Pro Tyr Thr Phe Gly Gly Gly Thr
225                 230                 235                 240

Lys Gly Gly Gly Gly Ser His Arg Arg Cys Asn Lys Asn Asn Lys Lys
                245                 250                 255

Arg Leu Glu Ile Lys Arg Leu Glu His His His His His His
            260                 265                 270
```

<210> SEQ ID NO 37
<211> LENGTH: 270
<212> TYPE: PRT
<213> ORGANISM: Artificial Sequence
<220> FEATURE:
<223> OTHER INFORMATION: Synthetic construct

<400> SEQUENCE: 37

```
Met Ala Gln Val Lys Leu Gln Glu Ser Gly Pro Glu Leu Val Arg Pro
1               5                   10                  15

Gly Thr Ser Val Lys Val Ser Cys Lys Ala Ser Gly Tyr Ala Phe Thr
            20                  25                  30

Asn Tyr Leu Ile Glu Trp Ile Lys Gln Arg Pro Gly Gln Gly Leu Glu
        35                  40                  45

Trp Ile Gly Val Ile His Pro Gly Asn Gly Gly Thr Asn Tyr Asn Glu
    50                  55                  60

Asn Phe Lys Gly Lys Ala Thr Leu Thr Ala Asp Lys Ser Ser Ser Thr
65                  70                  75                  80

Ala Tyr Met Gln Leu Ser Ser Leu Thr Ser Asp Asp Ser Ala Val Tyr
                85                  90                  95
```

```
Phe Cys Ala Ser Gly Asn Asp Gly Ser Tyr Trp Gly Gln Gly Thr Thr
            100                 105                 110

Val Thr Val Ser Ser Gly Gly Gly Gly Ser Gly Gly Gly Gly Ser Gly
        115                 120                 125

Gly Gly Gly Ser Asp Ile Glu Leu Thr Gln Ser Pro Ser Ser Leu Thr
    130                 135                 140

Val Thr Ala Gly Glu Lys Val Thr Met Ser Cys Lys Ser Ser Gln Ser
145                 150                 155                 160

Leu Leu Asn Ser Gly Asp Gln Lys Ile Tyr Leu Thr Trp Tyr Gln Gln
                165                 170                 175

Lys Pro Gly Gln Pro Pro Lys Leu Leu Ile Tyr Trp Ala Ser Thr Arg
            180                 185                 190

Glu Ser Gly Val Pro Asp Arg Phe Thr Gly Ser Val Ser Gly Thr Asp
        195                 200                 205

Phe Thr Leu Thr Ile Ser Ser Val Gln Ala Glu Asp Leu Ala Val Tyr
    210                 215                 220

Tyr Cys Gln Asn Asp Tyr Asn Tyr Pro Tyr Thr Phe Gly Gly Gly Thr
225                 230                 235                 240

Lys Gly Gly Gly Gly Ser His Arg Arg Cys Asn Pro Asn Asn Lys Lys
                245                 250                 255

Arg Leu Glu Ile Lys Arg Leu Glu His His His His His His
            260                 265                 270


<210> SEQ ID NO 38
<211> LENGTH: 273
<212> TYPE: PRT
<213> ORGANISM: Artificial Sequence
<220> FEATURE:
<223> OTHER INFORMATION: Synthetic construct

<400> SEQUENCE: 38

Met Ala Gln Val Lys Leu Gln Glu Ser Gly Pro Glu Leu Val Arg Pro
1               5                   10                  15

Gly Thr Ser Val Lys Val Ser Cys Lys Ala Ser Gly Tyr Ala Phe Thr
            20                  25                  30

Asn Tyr Leu Ile Glu Trp Ile Lys Gln Arg Pro Gly Gln Gly Leu Glu
        35                  40                  45

Trp Ile Gly Val Ile His Pro Gly Asn Gly Gly Thr Asn Tyr Asn Glu
    50                  55                  60

Asn Phe Lys Gly Lys Ala Thr Leu Thr Ala Asp Lys Ser Ser Ser Thr
65                  70                  75                  80

Ala Tyr Met Gln Leu Ser Ser Leu Thr Ser Asp Asp Ser Ala Val Tyr
                85                  90                  95

Phe Cys Ala Ser Gly Asn Asp Gly Ser Tyr Trp Gly Gln Gly Thr Thr
            100                 105                 110

Val Thr Val Ser Ser Gly Gly Gly Gly Ser Gly Gly Gly Gly Ser Gly
        115                 120                 125

Gly Gly Gly Ser Asp Ile Glu Leu Thr Gln Ser Pro Ser Ser Leu Thr
    130                 135                 140

Val Thr Ala Gly Glu Lys Val Thr Met Ser Cys Lys Ser Ser Gln Ser
145                 150                 155                 160

Leu Leu Asn Ser Gly Asp Gln Lys Ile Tyr Leu Thr Trp Tyr Gln Gln
                165                 170                 175

Lys Pro Gly Gln Pro Pro Lys Leu Leu Ile Tyr Trp Ala Ser Thr Arg
            180                 185                 190
```

```
Glu Ser Gly Val Pro Asp Arg Phe Thr Gly Ser Val Ser Gly Thr Asp
        195                 200                 205

Phe Thr Leu Thr Ile Ser Ser Val Gln Ala Glu Asp Leu Ala Val Tyr
    210                 215                 220

Tyr Cys Gln Asn Asp Tyr Asn Tyr Pro Tyr Thr Phe Gly Gly Gly Thr
225                 230                 235                 240

Lys Gly Gly Gly Gly Ser Val Ser Arg Arg Arg Arg Arg Arg Gly Gly
                245                 250                 255

Arg Arg Arg Arg Leu Glu Ile Lys Arg Leu Glu His His His His His
            260                 265                 270

His


<210> SEQ ID NO 39
<211> LENGTH: 274
<212> TYPE: PRT
<213> ORGANISM: Artificial Sequence
<220> FEATURE:
<223> OTHER INFORMATION: Synthetic construct

<400> SEQUENCE: 39

Met Ala Gln Val Lys Leu Gln Glu Ser Gly Pro Glu Leu Val Arg Pro
1               5                   10                  15

Gly Thr Ser Val Lys Val Ser Cys Lys Ala Ser Gly Tyr Ala Phe Thr
            20                  25                  30

Asn Tyr Leu Ile Glu Trp Ile Lys Gln Arg Pro Gly Gln Gly Leu Glu
        35                  40                  45

Trp Ile Gly Val Ile His Pro Gly Asn Gly Gly Thr Asn Tyr Asn Glu
    50                  55                  60

Asn Phe Lys Gly Lys Ala Thr Leu Thr Ala Asp Lys Ser Ser Ser Thr
65                  70                  75                  80

Ala Tyr Met Gln Leu Ser Ser Leu Thr Ser Asp Asp Ser Ala Val Tyr
                85                  90                  95

Phe Cys Ala Ser Gly Asn Asp Gly Ser Tyr Trp Gly Gln Gly Thr Thr
            100                 105                 110

Val Thr Val Ser Ser Gly Gly Gly Gly Ser Gly Gly Gly Gly Ser Gly
        115                 120                 125

Gly Gly Gly Ser Asp Ile Glu Leu Thr Gln Ser Pro Ser Ser Leu Thr
    130                 135                 140

Val Thr Ala Gly Glu Lys Val Thr Met Ser Cys Lys Ser Ser Gln Ser
145                 150                 155                 160

Leu Leu Asn Ser Gly Asp Gln Lys Ile Tyr Leu Thr Trp Tyr Gln Gln
                165                 170                 175

Lys Pro Gly Gln Pro Pro Lys Leu Leu Ile Tyr Trp Ala Ser Thr Arg
            180                 185                 190

Glu Ser Gly Val Pro Asp Arg Phe Thr Gly Ser Val Ser Gly Thr Asp
        195                 200                 205

Phe Thr Leu Thr Ile Ser Ser Val Gln Ala Glu Asp Leu Ala Val Tyr
    210                 215                 220

Tyr Cys Gln Asn Asp Tyr Asn Tyr Pro Tyr Thr Phe Gly Gly Gly Thr
225                 230                 235                 240

Lys Gly Gly Gly Gly Ser Gly Lys Cys Ser Thr Arg Gly Arg Lys Cys
                245                 250                 255

Cys Arg Arg Lys Lys Leu Glu Ile Lys Arg Leu Glu His His His His
            260                 265                 270

His His
```

<210> SEQ ID NO 40
<211> LENGTH: 275
<212> TYPE: PRT
<213> ORGANISM: Artificial Sequence
<220> FEATURE:
<223> OTHER INFORMATION: Synthetic construct

<400> SEQUENCE: 40

```
Met Ala Gln Val Lys Leu Gln Glu Ser Gly Pro Glu Leu Val Arg Pro
1               5                   10                  15

Gly Thr Ser Val Lys Val Ser Cys Lys Ala Ser Gly Tyr Ala Phe Thr
            20                  25                  30

Asn Tyr Leu Ile His Arg Arg Cys Asn Lys Asn Asn Lys Lys Arg Gly
        35                  40                  45

Gly Gly Gly Ser Glu Trp Ile Lys Gln Arg Pro Gly Gln Gly Leu Glu
    50                  55                  60

Trp Ile Gly Val Ile His Pro Gly Asn Gly Gly Thr Asn Tyr Asn Glu
65                  70                  75                  80

Asn Phe Lys Gly Lys Ala Thr Leu Thr Ala Asp Lys Ser Ser Ser Thr
                85                  90                  95

Ala Tyr Met Gln Leu Ser Ser Leu Thr Ser Asp Asp Ser Ala Val Tyr
            100                 105                 110

Phe Cys Ala Ser Gly Asn Asp Gly Ser Tyr Trp Gly Gln Gly Thr Thr
        115                 120                 125

Val Thr Val Ser Ser Gly Gly Gly Gly Ser Gly Lys Gly Gly Ser Gly
    130                 135                 140

Gly Gly Gly Ser Gly Gly Gly Gly Ser Asp Ile Glu Leu Thr Gln Ser
145                 150                 155                 160

Pro Ser Ser Leu Thr Val Thr Ala Gly Glu Lys Val Thr Met Ser Cys
                165                 170                 175

Lys Ser Ser Gln Ser Leu Leu Asn Ser Gly Asp Gln Lys Ile Tyr Leu
            180                 185                 190

Thr Trp Tyr Gln Gln Lys Pro Gly Gln Pro Pro Lys Leu Leu Ile Tyr
        195                 200                 205

Trp Ala Ser Thr Arg Glu Ser Gly Val Pro Asp Arg Phe Thr Gly Ser
    210                 215                 220

Val Ser Gly Thr Asp Phe Thr Leu Thr Ile Ser Ser Val Gln Ala Glu
225                 230                 235                 240

Asp Leu Ala Val Tyr Tyr Cys Gln Asn Asp Tyr Asn Tyr Pro Tyr Thr
                245                 250                 255

Phe Gly Gly Gly Thr Lys Leu Glu Ile Lys Arg Leu Glu His His His
            260                 265                 270

His His His
        275
```

<210> SEQ ID NO 41
<211> LENGTH: 275
<212> TYPE: PRT
<213> ORGANISM: Artificial Sequence
<220> FEATURE:
<223> OTHER INFORMATION: Synthetic construct

<400> SEQUENCE: 41

```
Met Ala Gln Val Lys Leu Gln Glu Ser Gly Pro Glu Leu Val Arg Pro
1               5                   10                  15

Gly Thr Ser Val Lys Val Ser Cys Lys Ala Ser Gly Tyr Ala Phe Thr
```

-continued

```
            20                  25                  30

Asn Tyr Leu Ile His Arg Arg Cys Asn Pro Asn Asn Lys Lys Arg Gly
        35                  40                  45

Gly Gly Gly Ser Glu Trp Ile Lys Gln Arg Pro Gly Gln Gly Leu Glu
    50                  55                  60

Trp Ile Gly Val Ile His Pro Gly Asn Gly Gly Thr Asn Tyr Asn Glu
65                  70                  75                  80

Asn Phe Lys Gly Lys Ala Thr Leu Thr Ala Asp Lys Ser Ser Ser Thr
                85                  90                  95

Ala Tyr Met Gln Leu Ser Ser Leu Thr Ser Asp Asp Ser Ala Val Tyr
            100                 105                 110

Phe Cys Ala Ser Gly Asn Asp Gly Ser Tyr Trp Gly Gln Gly Thr Thr
        115                 120                 125

Val Thr Val Ser Ser Gly Gly Gly Gly Ser Gly Lys Gly Gly Ser Gly
    130                 135                 140

Gly Gly Gly Ser Gly Gly Gly Gly Ser Asp Ile Glu Leu Thr Gln Ser
145                 150                 155                 160

Pro Ser Ser Leu Thr Val Thr Ala Gly Glu Lys Val Thr Met Ser Cys
                165                 170                 175

Lys Ser Ser Gln Ser Leu Leu Asn Ser Gly Asp Gln Lys Ile Tyr Leu
            180                 185                 190

Thr Trp Tyr Gln Gln Lys Pro Gly Gln Pro Pro Lys Leu Leu Ile Tyr
        195                 200                 205

Trp Ala Ser Thr Arg Glu Ser Gly Val Pro Asp Arg Phe Thr Gly Ser
    210                 215                 220

Val Ser Gly Thr Asp Phe Thr Leu Thr Ile Ser Ser Val Gln Ala Glu
225                 230                 235                 240

Asp Leu Ala Val Tyr Tyr Cys Gln Asn Asp Tyr Asn Tyr Pro Tyr Thr
                245                 250                 255

Phe Gly Gly Gly Thr Lys Leu Glu Ile Lys Arg Leu Glu His His His
            260                 265                 270

His His His
        275
```

<210> SEQ ID NO 42
<211> LENGTH: 278
<212> TYPE: PRT
<213> ORGANISM: Artificial Sequence
<220> FEATURE:
<223> OTHER INFORMATION: Synthetic construct

<400> SEQUENCE: 42

```
Met Ala Gln Val Lys Leu Gln Glu Ser Gly Pro Glu Leu Val Arg Pro
1               5                   10                  15

Gly Thr Ser Val Lys Val Ser Cys Lys Ala Ser Gly Tyr Ala Phe Thr
            20                  25                  30

Asn Tyr Leu Ile Val Ser Arg Arg Arg Arg Arg Arg Gly Gly Arg Arg
        35                  40                  45

Arg Arg Gly Gly Gly Gly Ser Glu Trp Ile Lys Gln Arg Pro Gly Gln
    50                  55                  60

Gly Leu Glu Trp Ile Gly Val Ile His Pro Gly Asn Gly Gly Thr Asn
65                  70                  75                  80

Tyr Asn Glu Asn Phe Lys Gly Lys Ala Thr Leu Thr Ala Asp Lys Ser
                85                  90                  95

Ser Ser Thr Ala Tyr Met Gln Leu Ser Ser Leu Thr Ser Asp Asp Ser
```

-continued 100 105 110

Ala Val Tyr Phe Cys Ala Ser Gly Asn Asp Gly Ser Tyr Trp Gly Gln
115 120 125

Gly Thr Thr Val Thr Val Ser Ser Gly Gly Gly Gly Ser Gly Lys Gly
130 135 140

Gly Ser Gly Gly Gly Gly Ser Gly Gly Gly Gly Ser Asp Ile Glu Leu
145 150 155 160

Thr Gln Ser Pro Ser Ser Leu Thr Val Thr Ala Gly Glu Lys Val Thr
165 170 175

Met Ser Cys Lys Ser Ser Gln Ser Leu Leu Asn Ser Gly Asp Gln Lys
180 185 190

Ile Tyr Leu Thr Trp Tyr Gln Gln Lys Pro Gly Gln Pro Pro Lys Leu
195 200 205

Leu Ile Tyr Trp Ala Ser Thr Arg Glu Ser Gly Val Pro Asp Arg Phe
210 215 220

Thr Gly Ser Val Ser Gly Thr Asp Phe Thr Leu Thr Ile Ser Ser Val
225 230 235 240

Gln Ala Glu Asp Leu Ala Val Tyr Tyr Cys Gln Asn Asp Tyr Asn Tyr
245 250 255

Pro Tyr Thr Phe Gly Gly Gly Thr Lys Leu Glu Ile Lys Arg Leu Glu
260 265 270

His His His His His His
275

<210> SEQ ID NO 43
<211> LENGTH: 280
<212> TYPE: PRT
<213> ORGANISM: Artificial Sequence
<220> FEATURE:
<223> OTHER INFORMATION: Synthetic construct

<400> SEQUENCE: 43

Met Ala Gln Val Lys Leu Gln Glu Ser Gly Pro Glu Leu Val Arg Pro
1 5 10 15

Gly Thr Ser Val Lys Val Ser Cys Lys Ala Ser Gly Tyr Ala Phe Thr
20 25 30

Asn Tyr Leu Ile Gly Lys Cys Ser Thr Arg Gly Arg Lys Cys Cys Arg
35 40 45

Arg Lys Lys Gly Gly Gly Gly Ser Glu Trp Ile Lys Gln Arg Pro Gly
50 55 60

Gln Gly Leu Glu Trp Ile Gly Val Ile His Pro Gly Asn Gly Gly Thr
65 70 75 80

Asn Tyr Asn Glu Asn Phe Lys Gly Lys Ala Thr Leu Thr Ala Asp Lys
85 90 95

Ser Ser Ser Thr Ala Tyr Met Gln Leu Ser Ser Leu Thr Ser Asp Asp
100 105 110

Ser Ala Val Tyr Phe Cys Ala Ser Gly Asn Asp Gly Ser Tyr Trp Gly
115 120 125

Gln Gly Thr Thr Val Thr Val Ser Ser Gly Gly Gly Gly Ser Gly Lys
130 135 140

Gly Gly Ser Gly Gly Gly Gly Ser Gly Gly Gly Gly Ser Asp Ile Glu
145 150 155 160

Leu Thr Gln Ser Pro Ser Ser Leu Thr Val Thr Ala Gly Glu Lys Val
165 170 175

Thr Met Ser Cys Lys Ser Ser Gln Ser Leu Leu Asn Ser Gly Asp Gln

```
            180                 185                 190

Lys Ile Tyr Leu Thr Trp Tyr Gln Gln Lys Pro Gly Gln Pro Pro Lys
        195                 200                 205

Leu Leu Ile Tyr Trp Ala Ser Thr Arg Glu Ser Gly Val Pro Asp Arg
    210                 215                 220

Phe Thr Gly Ser Val Ser Gly Thr Asp Phe Thr Leu Thr Ile Ser Ser
225                 230                 235                 240

Val Gln Ala Glu Asp Leu Ala Val Tyr Tyr Cys Gln Asn Asp Tyr Asn
                245                 250                 255

Tyr Pro Tyr Thr Phe Gly Gly Gly Thr Lys Leu Glu Ile Lys Arg Leu
            260                 265                 270

Glu His His His His His His His
        275                 280
```

<210> SEQ ID NO 44
<211> LENGTH: 287
<212> TYPE: PRT
<213> ORGANISM: Artificial Sequence
<220> FEATURE:
<223> OTHER INFORMATION: Synthetic construct

<400> SEQUENCE: 44

```
Met Ala Trp Val Trp Thr Leu Leu Phe Leu Met Ala Ala Ala Gln Ser
1               5                   10                  15

Ile Gln Ala Glu Trp Ile Lys Gln Arg Pro Gly Gln Gly Leu Glu Trp
            20                  25                  30

Ile Gly Val Ile His Pro Gly Asn Gly Gly Thr Asn Tyr Asn Glu Asn
        35                  40                  45

Phe Lys Gly Lys Ala Thr Leu Thr Ala Asp Lys Ser Ser Ser Thr Ala
    50                  55                  60

Tyr Met Gln Leu Ser Ser Leu Thr Ser Asp Asp Ser Ala Val Tyr Phe
65                  70                  75                  80

Cys Ala Ser Gly Asn Asp Gly Ser Tyr Trp Gly Gln Gly Thr Thr Val
                85                  90                  95

Thr Val Ser Ser Gly Gly Gly Gly Ser Gly Lys Gly Gly Ser Gly Gly
            100                 105                 110

Gly Gly Ser Gly Gly Gly Gly Ser Asp Ile Glu Leu Thr Gln Ser Pro
        115                 120                 125

Ser Ser Leu Thr Val Thr Ala Gly Glu Lys Val Thr Met Ser Cys Lys
    130                 135                 140

Ser Ser Gln Ser Leu Leu Asn Ser Gly Asp Gln Lys Ile Tyr Leu Thr
145                 150                 155                 160

Trp Tyr Gln Gln Lys Pro Gly Gln Pro Pro Lys Leu Leu Ile Tyr Trp
                165                 170                 175

Ala Ser Thr Arg Glu Ser Gly Val Pro Asp Arg Phe Thr Gly Ser Val
            180                 185                 190

Ser Gly Thr Asp Phe Thr Leu Thr Ile Ser Ser Val Gln Ala Glu Asp
        195                 200                 205

Leu Ala Val Tyr Tyr Cys Gln Asn Asp Tyr Asn Tyr Pro Tyr Thr Phe
    210                 215                 220

Gly Gly Gly Thr Lys Gly Gly Gly Gly Ser His Arg Arg Cys Asn Lys
225                 230                 235                 240

Asn Asn Lys Lys Arg Leu Glu Ile Lys Arg Gly Ser Glu Asn Leu Tyr
                245                 250                 255

Phe Gln Gly Gly Ser Gly Lys Pro Ile Pro Asn Pro Leu Leu Gly Leu
```

```
            260                 265                 270

Asp Ser Thr Gly Gly Ser Gly Gly Ser His His His His His His
        275                 280                 285


<210> SEQ ID NO 45
<211> LENGTH: 287
<212> TYPE: PRT
<213> ORGANISM: Artificial Sequence
<220> FEATURE:
<223> OTHER INFORMATION: Synthetic construct

<400> SEQUENCE: 45

Met Ala Trp Val Trp Thr Leu Leu Phe Leu Met Ala Ala Ala Gln Ser
1               5                   10                  15

Ile Gln Ala Glu Trp Ile Lys Gln Arg Pro Gly Gln Gly Leu Glu Trp
            20                  25                  30

Ile Gly Val Ile His Pro Gly Asn Gly Gly Thr Asn Tyr Asn Glu Asn
        35                  40                  45

Phe Lys Gly Lys Ala Thr Leu Thr Ala Asp Lys Ser Ser Ser Thr Ala
    50                  55                  60

Tyr Met Gln Leu Ser Ser Leu Thr Ser Asp Asp Ser Ala Val Tyr Phe
65                  70                  75                  80

Cys Ala Ser Gly Asn Asp Gly Ser Tyr Trp Gly Gln Gly Thr Thr Val
                85                  90                  95

Thr Val Ser Ser Gly Gly Gly Gly Ser Gly Lys Gly Gly Ser Gly Gly
            100                 105                 110

Gly Gly Ser Gly Gly Gly Gly Ser Asp Ile Glu Leu Thr Gln Ser Pro
        115                 120                 125

Ser Ser Leu Thr Val Thr Ala Gly Glu Lys Val Thr Met Ser Cys Lys
    130                 135                 140

Ser Ser Gln Ser Leu Leu Asn Ser Gly Asp Gln Lys Ile Tyr Leu Thr
145                 150                 155                 160

Trp Tyr Gln Gln Lys Pro Gly Gln Pro Pro Lys Leu Leu Ile Tyr Trp
                165                 170                 175

Ala Ser Thr Arg Glu Ser Gly Val Pro Asp Arg Phe Thr Gly Ser Val
            180                 185                 190

Ser Gly Thr Asp Phe Thr Leu Thr Ile Ser Ser Val Gln Ala Glu Asp
        195                 200                 205

Leu Ala Val Tyr Tyr Cys Gln Asn Asp Tyr Asn Tyr Pro Tyr Thr Phe
    210                 215                 220

Gly Gly Gly Thr Lys Gly Gly Gly Gly Ser His Arg Arg Cys Asn Pro
225                 230                 235                 240

Asn Asn Lys Lys Arg Leu Glu Ile Lys Arg Gly Ser Glu Asn Leu Tyr
                245                 250                 255

Phe Gln Gly Gly Ser Gly Lys Pro Ile Pro Asn Pro Leu Leu Gly Leu
            260                 265                 270

Asp Ser Thr Gly Gly Ser Gly Gly Ser His His His His His His
        275                 280                 285


<210> SEQ ID NO 46
<211> LENGTH: 290
<212> TYPE: PRT
<213> ORGANISM: Artificial Sequence
<220> FEATURE:
<223> OTHER INFORMATION: Synthetic construct

<400> SEQUENCE: 46
```

-continued

Met Ala Trp Val Trp Thr Leu Leu Phe Leu Met Ala Ala Ala Gln Ser
1 5 10 15

Ile Gln Ala Glu Trp Ile Lys Gln Arg Pro Gly Gln Gly Leu Glu Trp
20 25 30

Ile Gly Val Ile His Pro Gly Asn Gly Gly Thr Asn Tyr Asn Glu Asn
35 40 45

Phe Lys Gly Lys Ala Thr Leu Thr Ala Asp Lys Ser Ser Ser Thr Ala
50 55 60

Tyr Met Gln Leu Ser Ser Leu Thr Ser Asp Asp Ser Ala Val Tyr Phe
65 70 75 80

Cys Ala Ser Gly Asn Asp Gly Ser Tyr Trp Gly Gln Gly Thr Thr Val
85 90 95

Thr Val Ser Ser Gly Gly Gly Gly Ser Gly Lys Gly Gly Ser Gly Gly
100 105 110

Gly Gly Ser Gly Gly Gly Gly Ser Asp Ile Glu Leu Thr Gln Ser Pro
115 120 125

Ser Ser Leu Thr Val Thr Ala Gly Glu Lys Val Thr Met Ser Cys Lys
130 135 140

Ser Ser Gln Ser Leu Leu Asn Ser Gly Asp Gln Lys Ile Tyr Leu Thr
145 150 155 160

Trp Tyr Gln Gln Lys Pro Gly Gln Pro Pro Lys Leu Leu Ile Tyr Trp
165 170 175

Ala Ser Thr Arg Glu Ser Gly Val Pro Asp Arg Phe Thr Gly Ser Val
180 185 190

Ser Gly Thr Asp Phe Thr Leu Thr Ile Ser Ser Val Gln Ala Glu Asp
195 200 205

Leu Ala Val Tyr Tyr Cys Gln Asn Asp Tyr Asn Tyr Pro Tyr Thr Phe
210 215 220

Gly Gly Gly Thr Lys Gly Gly Gly Gly Ser Val Ser Arg Arg Arg Arg
225 230 235 240

Arg Arg Gly Gly Arg Arg Arg Arg Leu Glu Ile Lys Arg Gly Ser Glu
245 250 255

Asn Leu Tyr Phe Gln Gly Gly Ser Gly Lys Pro Ile Pro Asn Pro Leu
260 265 270

Leu Gly Leu Asp Ser Thr Gly Gly Ser Gly Gly Ser His His His His
275 280 285

His His
290

<210> SEQ ID NO 47
<211> LENGTH: 291
<212> TYPE: PRT
<213> ORGANISM: Artificial Sequence
<220> FEATURE:
<223> OTHER INFORMATION: Synthetic construct

<400> SEQUENCE: 47

Met Ala Trp Val Trp Thr Leu Leu Phe Leu Met Ala Ala Ala Gln Ser
1 5 10 15

Ile Gln Ala Glu Trp Ile Lys Gln Arg Pro Gly Gln Gly Leu Glu Trp
20 25 30

Ile Gly Val Ile His Pro Gly Asn Gly Gly Thr Asn Tyr Asn Glu Asn
35 40 45

Phe Lys Gly Lys Ala Thr Leu Thr Ala Asp Lys Ser Ser Ser Thr Ala
50 55 60

-continued

```
Tyr Met Gln Leu Ser Ser Leu Thr Ser Asp Asp Ser Ala Val Tyr Phe
65                  70                  75                  80

Cys Ala Ser Gly Asn Asp Gly Ser Tyr Trp Gly Gln Gly Thr Thr Val
                85                  90                  95

Thr Val Ser Ser Gly Gly Gly Gly Ser Gly Lys Gly Gly Ser Gly Gly
            100                 105                 110

Gly Gly Ser Gly Gly Gly Gly Ser Asp Ile Glu Leu Thr Gln Ser Pro
        115                 120                 125

Ser Ser Leu Thr Val Thr Ala Gly Glu Lys Val Thr Met Ser Cys Lys
    130                 135                 140

Ser Ser Gln Ser Leu Leu Asn Ser Gly Asp Gln Lys Ile Tyr Leu Thr
145                 150                 155                 160

Trp Tyr Gln Gln Lys Pro Gly Gln Pro Pro Lys Leu Leu Ile Tyr Trp
                165                 170                 175

Ala Ser Thr Arg Glu Ser Gly Val Pro Asp Arg Phe Thr Gly Ser Val
            180                 185                 190

Ser Gly Thr Asp Phe Thr Leu Thr Ile Ser Ser Val Gln Ala Glu Asp
        195                 200                 205

Leu Ala Val Tyr Tyr Cys Gln Asn Asp Tyr Asn Tyr Pro Tyr Thr Phe
    210                 215                 220

Gly Gly Gly Thr Lys Gly Gly Gly Gly Ser Gly Lys Cys Ser Thr Arg
225                 230                 235                 240

Gly Arg Lys Cys Cys Arg Arg Lys Lys Leu Glu Ile Lys Arg Gly Ser
                245                 250                 255

Glu Asn Leu Tyr Phe Gln Gly Gly Ser Gly Lys Pro Ile Pro Asn Pro
            260                 265                 270

Leu Leu Gly Leu Asp Ser Thr Gly Gly Ser Gly Gly Ser His His His
        275                 280                 285

His His His
    290
```

<210> SEQ ID NO 48
<211> LENGTH: 287
<212> TYPE: PRT
<213> ORGANISM: Artificial Sequence
<220> FEATURE:
<223> OTHER INFORMATION: Synthetic construct

<400> SEQUENCE: 48

```
Met Ala Trp Val Trp Thr Leu Leu Phe Leu Met Ala Ala Ala Gln Ser
1               5                   10                  15

Ile Gln Ala His Arg Arg Cys Asn Lys Asn Asn Lys Lys Arg Gly Gly
            20                  25                  30

Gly Gly Ser Glu Trp Ile Lys Gln Arg Pro Gly Gln Gly Leu Glu Trp
        35                  40                  45

Ile Gly Val Ile His Pro Gly Asn Gly Gly Thr Asn Tyr Asn Glu Asn
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Ser Asp Asp Ser Ala Val Tyr Phe
                85                  90                  95

Cys Ala Ser Gly Asn Asp Gly Ser Tyr Trp Gly Gln Gly Thr Thr Val
            100                 105                 110

Thr Val Ser Ser Gly Gly Gly Gly Ser Gly Lys Gly Gly Ser Gly Gly
        115                 120                 125
```

-continued

```
Gly Gly Ser Gly Gly Gly Gly Ser Asp Ile Glu Leu Thr Gln Ser Pro
    130                 135                 140

Ser Ser Leu Thr Val Thr Ala Gly Glu Lys Val Thr Met Ser Cys Lys
145                 150                 155                 160

Ser Ser Gln Ser Leu Leu Asn Ser Gly Asp Gln Lys Ile Tyr Leu Thr
                165                 170                 175

Trp Tyr Gln Gln Lys Pro Gly Gln Pro Pro Lys Leu Leu Ile Tyr Trp
            180                 185                 190

Ala Ser Thr Arg Glu Ser Gly Val Pro Asp Arg Phe Thr Gly Ser Val
        195                 200                 205

Ser Gly Thr Asp Phe Thr Leu Thr Ile Ser Ser Val Gln Ala Glu Asp
    210                 215                 220

Leu Ala Val Tyr Tyr Cys Gln Asn Asp Tyr Asn Tyr Pro Tyr Thr Phe
225                 230                 235                 240

Gly Gly Gly Thr Lys Leu Glu Ile Lys Arg Gly Ser Glu Asn Leu Tyr
                245                 250                 255

Phe Gln Gly Gly Ser Gly Lys Pro Ile Pro Asn Pro Leu Leu Gly Leu
            260                 265                 270

Asp Ser Thr Gly Gly Ser Gly Gly Ser His His His His His His
        275                 280                 285
```

<210> SEQ ID NO 49
<211> LENGTH: 287
<212> TYPE: PRT
<213> ORGANISM: Artificial Sequence
<220> FEATURE:
<223> OTHER INFORMATION: Synthetic construct

<400> SEQUENCE: 49

```
Met Ala Trp Val Trp Thr Leu Leu Phe Leu Met Ala Ala Ala Gln Ser
1               5                   10                  15

Ile Gln Ala His Arg Arg Cys Asn Pro Asn Asn Lys Lys Arg Gly Gly
            20                  25                  30

Gly Gly Ser Glu Trp Ile Lys Gln Arg Pro Gly Gln Gly Leu Glu Trp
        35                  40                  45

Ile Gly Val Ile His Pro Gly Asn Gly Gly Thr Asn Tyr Asn Glu Asn
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Ser Asp Asp Ser Ala Val Tyr Phe
                85                  90                  95

Cys Ala Ser Gly Asn Asp Gly Ser Tyr Trp Gly Gln Gly Thr Thr Val
            100                 105                 110

Thr Val Ser Ser Gly Gly Gly Gly Ser Gly Lys Gly Gly Ser Gly Gly
        115                 120                 125

Gly Gly Ser Gly Gly Gly Gly Ser Asp Ile Glu Leu Thr Gln Ser Pro
    130                 135                 140

Ser Ser Leu Thr Val Thr Ala Gly Glu Lys Val Thr Met Ser Cys Lys
145                 150                 155                 160

Ser Ser Gln Ser Leu Leu Asn Ser Gly Asp Gln Lys Ile Tyr Leu Thr
                165                 170                 175

Trp Tyr Gln Gln Lys Pro Gly Gln Pro Pro Lys Leu Leu Ile Tyr Trp
            180                 185                 190

Ala Ser Thr Arg Glu Ser Gly Val Pro Asp Arg Phe Thr Gly Ser Val
        195                 200                 205
```

Ser Gly Thr Asp Phe Thr Leu Thr Ile Ser Ser Val Gln Ala Glu Asp
    210                 215                 220

Leu Ala Val Tyr Tyr Cys Gln Asn Asp Tyr Asn Tyr Pro Tyr Thr Phe
225                 230                 235                 240

Gly Gly Gly Thr Lys Leu Glu Ile Lys Arg Gly Ser Glu Asn Leu Tyr
                245                 250                 255

Phe Gln Gly Gly Ser Gly Lys Pro Ile Pro Asn Pro Leu Leu Gly Leu
            260                 265                 270

Asp Ser Thr Gly Gly Ser Gly Gly Ser His His His His His His
        275                 280                 285

<210> SEQ ID NO 50
<211> LENGTH: 290
<212> TYPE: PRT
<213> ORGANISM: Artificial Sequence
<220> FEATURE:
<223> OTHER INFORMATION: Synthetic construct

<400> SEQUENCE: 50

Met Ala Trp Val Trp Thr Leu Leu Phe Leu Met Ala Ala Ala Gln Ser
1               5                   10                  15

Ile Gln Ala Val Ser Arg Arg Arg Arg Arg Arg Gly Gly Arg Arg Arg
            20                  25                  30

Arg Gly Gly Gly Gly Ser Glu Trp Ile Lys Gln Arg Pro Gly Gln Gly
        35                  40                  45

Leu Glu Trp Ile Gly Val Ile His Pro Gly Asn Gly Gly Thr Asn Tyr
    50                  55                  60

Asn Glu Asn Phe Lys Gly Lys Ala Thr Leu Thr Ala Asp Lys Ser Ser
65                  70                  75                  80

Ser Thr Ala Tyr Met Gln Leu Ser Ser Leu Thr Ser Asp Asp Ser Ala
                85                  90                  95

Val Tyr Phe Cys Ala Ser Gly Asn Asp Gly Ser Tyr Trp Gly Gln Gly
            100                 105                 110

Thr Thr Val Thr Val Ser Ser Gly Gly Gly Gly Ser Gly Lys Gly Gly
        115                 120                 125

Ser Gly Gly Gly Gly Ser Gly Gly Gly Gly Ser Asp Ile Glu Leu Thr
    130                 135                 140

Gln Ser Pro Ser Ser Leu Thr Val Thr Ala Gly Glu Lys Val Thr Met
145                 150                 155                 160

Ser Cys Lys Ser Ser Gln Ser Leu Leu Asn Ser Gly Asp Gln Lys Ile
                165                 170                 175

Tyr Leu Thr Trp Tyr Gln Gln Lys Pro Gly Gln Pro Pro Lys Leu Leu
            180                 185                 190

Ile Tyr Trp Ala Ser Thr Arg Glu Ser Gly Val Pro Asp Arg Phe Thr
        195                 200                 205

Gly Ser Val Ser Gly Thr Asp Phe Thr Leu Thr Ile Ser Ser Val Gln
    210                 215                 220

Ala Glu Asp Leu Ala Val Tyr Tyr Cys Gln Asn Asp Tyr Asn Tyr Pro
225                 230                 235                 240

Tyr Thr Phe Gly Gly Gly Thr Lys Leu Glu Ile Lys Arg Gly Ser Glu
                245                 250                 255

Asn Leu Tyr Phe Gln Gly Gly Ser Gly Lys Pro Ile Pro Asn Pro Leu
            260                 265                 270

Leu Gly Leu Asp Ser Thr Gly Gly Ser Gly Gly Ser His His His His
        275                 280                 285

His His
290

<210> SEQ ID NO 51
<211> LENGTH: 291
<212> TYPE: PRT
<213> ORGANISM: Artificial Sequence
<220> FEATURE:
<223> OTHER INFORMATION: Synthetic construct

<400> SEQUENCE: 51

Met Ala Trp Val Trp Thr Leu Leu Phe Leu Met Ala Ala Ala Gln Ser
1 5 10 15

Ile Gln Ala Gly Lys Cys Ser Thr Arg Gly Arg Lys Cys Cys Arg Arg
20 25 30

Lys Lys Gly Gly Gly Gly Ser Glu Trp Ile Lys Gln Arg Pro Gly Gln
35 40 45

Gly Leu Glu Trp Ile Gly Val Ile His Pro Gly Asn Gly Gly Thr Asn
50 55 60

Tyr Asn Glu Asn Phe Lys Gly Lys Ala Thr Leu Thr Ala Asp Lys Ser
65 70 75 80

Ser Ser Thr Ala Tyr Met Gln Leu Ser Ser Leu Thr Ser Asp Asp Ser
85 90 95

Ala Val Tyr Phe Cys Ala Ser Gly Asn Asp Gly Ser Tyr Trp Gly Gln
100 105 110

Gly Thr Thr Val Thr Val Ser Ser Gly Gly Gly Gly Ser Gly Lys Gly
115 120 125

Gly Ser Gly Gly Gly Gly Ser Gly Gly Gly Gly Ser Asp Ile Glu Leu
130 135 140

Thr Gln Ser Pro Ser Ser Leu Thr Val Thr Ala Gly Glu Lys Val Thr
145 150 155 160

Met Ser Cys Lys Ser Ser Gln Ser Leu Leu Asn Ser Gly Asp Gln Lys
165 170 175

Ile Tyr Leu Thr Trp Tyr Gln Gln Lys Pro Gly Gln Pro Pro Lys Leu
180 185 190

Leu Ile Tyr Trp Ala Ser Thr Arg Glu Ser Gly Val Pro Asp Arg Phe
195 200 205

Thr Gly Ser Val Ser Gly Thr Asp Phe Thr Leu Thr Ile Ser Ser Val
210 215 220

Gln Ala Glu Asp Leu Ala Val Tyr Tyr Cys Gln Asn Asp Tyr Asn Tyr
225 230 235 240

Pro Tyr Thr Phe Gly Gly Gly Thr Lys Leu Glu Ile Lys Arg Gly Ser
245 250 255

Glu Asn Leu Tyr Phe Gln Gly Gly Ser Gly Lys Pro Ile Pro Asn Pro
260 265 270

Leu Leu Gly Leu Asp Ser Thr Gly Gly Ser Gly Gly Ser His His His
275 280 285

His His His
290

<210> SEQ ID NO 52
<211> LENGTH: 270
<212> TYPE: PRT
<213> ORGANISM: Artificial Sequence
<220> FEATURE:
<223> OTHER INFORMATION: Synthetic construct

<400> SEQUENCE: 52

Met Ala Gln Val Lys Leu Gln Glu Ser Gly Pro Glu Leu Val Arg Pro
1 5 10 15

Gly Thr Ser Val Lys Val Ser Cys Lys Ala Ser Gly Tyr Ala Phe Thr
20 25 30

Asn Tyr Leu Ile Glu Trp Ile Lys Gln Arg Pro Gly Gln Gly Leu Glu
35 40 45

Trp Ile Gly Val Ile His Pro Gly Asn Gly Gly Thr Asn Tyr Asn Glu
50 55 60

Asn Phe Lys Gly Lys Ala Thr Leu Thr Ala Asp Lys Ser Ser Ser Thr
65 70 75 80

Ala Tyr Met Gln Leu Ser Ser Leu Thr Ser Asp Asp Ser Ala Val Tyr
85 90 95

Phe Cys Ala Ser Gly Asn Asp Gly Ser Tyr Trp Gly Gln Gly Thr Thr
100 105 110

Val Thr Val Ser Ser Gly Gly Gly Gly Ser Gly Gly Gly Gly Ser Gly
115 120 125

Gly Gly Gly Ser Asp Ile Glu Leu Thr Gln Ser Pro Ser Ser Leu Thr
130 135 140

Val Thr Ala Gly Glu Lys Val Thr Met Ser Cys Lys Ser Ser Gln Ser
145 150 155 160

Leu Leu Asn Ser Gly Asp Gln Lys Ile Tyr Leu Thr Trp Tyr Gln Gln
165 170 175

Lys Pro Gly Gln Pro Pro Lys Leu Leu Ile Tyr Trp Ala Ser Thr Arg
180 185 190

Glu Ser Gly Val Pro Asp Arg Phe Thr Gly Ser Val Ser Gly Thr Asp
195 200 205

Phe Thr Leu Thr Ile Ser Ser Val Gln Ala Glu Asp Leu Ala Val Tyr
210 215 220

Tyr Cys Gln Asn Asp Tyr Asn Tyr Pro Tyr Thr Phe Gly Gly Gly Thr
225 230 235 240

Lys Gly Gly Gly Gly Ser His Arg Arg Cys Asn Lys Asn Asn Lys Lys
245 250 255

Arg Leu Glu Ile Lys Arg Leu Glu His His His His His His
260 265 270

<210> SEQ ID NO 53
<211> LENGTH: 270
<212> TYPE: PRT
<213> ORGANISM: Artificial Sequence
<220> FEATURE:
<223> OTHER INFORMATION: Synthetic construct

<400> SEQUENCE: 53

Met Ala Gln Val Lys Leu Gln Glu Ser Gly Pro Glu Leu Val Arg Pro
1 5 10 15

Gly Thr Ser Val Lys Val Ser Cys Lys Ala Ser Gly Tyr Ala Phe Thr
20 25 30

Asn Tyr Leu Ile Glu Trp Ile Lys Gln Arg Pro Gly Gln Gly Leu Glu
35 40 45

Trp Ile Gly Val Ile His Pro Gly Asn Gly Gly Thr Asn Tyr Asn Glu
50 55 60

Asn Phe Lys Gly Lys Ala Thr Leu Thr Ala Asp Lys Ser Ser Ser Thr
65 70 75 80

Ala Tyr Met Gln Leu Ser Ser Leu Thr Ser Asp Asp Ser Ala Val Tyr
85 90 95

```
Phe Cys Ala Ser Gly Asn Asp Gly Ser Tyr Trp Gly Gln Gly Thr Thr
            100                 105                 110

Val Thr Val Ser Ser Gly Gly Gly Gly Ser Gly Gly Gly Gly Ser Gly
        115                 120                 125

Gly Gly Gly Ser Asp Ile Glu Leu Thr Gln Ser Pro Ser Ser Leu Thr
    130                 135                 140

Val Thr Ala Gly Glu Lys Val Thr Met Ser Cys Lys Ser Ser Gln Ser
145                 150                 155                 160

Leu Leu Asn Ser Gly Asp Gln Lys Ile Tyr Leu Thr Trp Tyr Gln Gln
                165                 170                 175

Lys Pro Gly Gln Pro Pro Lys Leu Leu Ile Tyr Trp Ala Ser Thr Arg
            180                 185                 190

Glu Ser Gly Val Pro Asp Arg Phe Thr Gly Ser Val Ser Gly Thr Asp
        195                 200                 205

Phe Thr Leu Thr Ile Ser Ser Val Gln Ala Glu Asp Leu Ala Val Tyr
    210                 215                 220

Tyr Cys Gln Asn Asp Tyr Asn Tyr Pro Tyr Thr Phe Gly Gly Gly Thr
225                 230                 235                 240

Lys Gly Gly Gly Gly Ser His Arg Arg Cys Asn Pro Asn Asn Lys Lys
                245                 250                 255

Arg Leu Glu Ile Lys Arg Leu Glu His His His His His His
            260                 265                 270


<210> SEQ ID NO 54
<211> LENGTH: 273
<212> TYPE: PRT
<213> ORGANISM: Artificial Sequence
<220> FEATURE:
<223> OTHER INFORMATION: Synthetic construct

<400> SEQUENCE: 54

Met Ala Gln Val Lys Leu Gln Glu Ser Gly Pro Glu Leu Val Arg Pro
1               5                   10                  15

Gly Thr Ser Val Lys Val Ser Cys Lys Ala Ser Gly Tyr Ala Phe Thr
            20                  25                  30

Asn Tyr Leu Ile Glu Trp Ile Lys Gln Arg Pro Gly Gln Gly Leu Glu
        35                  40                  45

Trp Ile Gly Val Ile His Pro Gly Asn Gly Gly Thr Asn Tyr Asn Glu
    50                  55                  60

Asn Phe Lys Gly Lys Ala Thr Leu Thr Ala Asp Lys Ser Ser Ser Thr
65                  70                  75                  80

Ala Tyr Met Gln Leu Ser Ser Leu Thr Ser Asp Asp Ser Ala Val Tyr
                85                  90                  95

Phe Cys Ala Ser Gly Asn Asp Gly Ser Tyr Trp Gly Gln Gly Thr Thr
            100                 105                 110

Val Thr Val Ser Ser Gly Gly Gly Gly Ser Gly Gly Gly Gly Ser Gly
        115                 120                 125

Gly Gly Gly Ser Asp Ile Glu Leu Thr Gln Ser Pro Ser Ser Leu Thr
    130                 135                 140

Val Thr Ala Gly Glu Lys Val Thr Met Ser Cys Lys Ser Ser Gln Ser
145                 150                 155                 160

Leu Leu Asn Ser Gly Asp Gln Lys Ile Tyr Leu Thr Trp Tyr Gln Gln
                165                 170                 175

Lys Pro Gly Gln Pro Pro Lys Leu Leu Ile Tyr Trp Ala Ser Thr Arg
            180                 185                 190
```

```
Glu Ser Gly Val Pro Asp Arg Phe Thr Gly Ser Val Ser Gly Thr Asp
        195                 200                 205

Phe Thr Leu Thr Ile Ser Ser Val Gln Ala Glu Asp Leu Ala Val Tyr
    210                 215                 220

Tyr Cys Gln Asn Asp Tyr Asn Tyr Pro Tyr Thr Phe Gly Gly Gly Thr
225                 230                 235                 240

Lys Gly Gly Gly Gly Ser Val Ser Arg Arg Arg Arg Arg Arg Gly Gly
                245                 250                 255

Arg Arg Arg Arg Leu Glu Ile Lys Arg Leu Glu His His His His His
            260                 265                 270

His
```

<210> SEQ ID NO 55
<211> LENGTH: 274
<212> TYPE: PRT
<213> ORGANISM: Artificial Sequence
<220> FEATURE:
<223> OTHER INFORMATION: Synthetic construct

<400> SEQUENCE: 55

```
Met Ala Gln Val Lys Leu Gln Glu Ser Gly Pro Glu Leu Val Arg Pro
1               5                   10                  15

Gly Thr Ser Val Lys Val Ser Cys Lys Ala Ser Gly Tyr Ala Phe Thr
            20                  25                  30

Asn Tyr Leu Ile Glu Trp Ile Lys Gln Arg Pro Gly Gln Gly Leu Glu
        35                  40                  45

Trp Ile Gly Val Ile His Pro Gly Asn Gly Gly Thr Asn Tyr Asn Glu
    50                  55                  60

Asn Phe Lys Gly Lys Ala Thr Leu Thr Ala Asp Lys Ser Ser Ser Thr
65                  70                  75                  80

Ala Tyr Met Gln Leu Ser Ser Leu Thr Ser Asp Asp Ser Ala Val Tyr
                85                  90                  95

Phe Cys Ala Ser Gly Asn Asp Gly Ser Tyr Trp Gly Gln Gly Thr Thr
            100                 105                 110

Val Thr Val Ser Ser Gly Gly Gly Gly Ser Gly Gly Gly Gly Ser Gly
        115                 120                 125

Gly Gly Gly Ser Asp Ile Glu Leu Thr Gln Ser Pro Ser Ser Leu Thr
    130                 135                 140

Val Thr Ala Gly Glu Lys Val Thr Met Ser Cys Lys Ser Ser Gln Ser
145                 150                 155                 160

Leu Leu Asn Ser Gly Asp Gln Lys Ile Tyr Leu Thr Trp Tyr Gln Gln
                165                 170                 175

Lys Pro Gly Gln Pro Pro Lys Leu Leu Ile Tyr Trp Ala Ser Thr Arg
            180                 185                 190

Glu Ser Gly Val Pro Asp Arg Phe Thr Gly Ser Val Ser Gly Thr Asp
        195                 200                 205

Phe Thr Leu Thr Ile Ser Ser Val Gln Ala Glu Asp Leu Ala Val Tyr
    210                 215                 220

Tyr Cys Gln Asn Asp Tyr Asn Tyr Pro Tyr Thr Phe Gly Gly Gly Thr
225                 230                 235                 240

Lys Gly Gly Gly Gly Ser Gly Lys Cys Ser Thr Arg Gly Arg Lys Cys
                245                 250                 255

Cys Arg Arg Lys Lys Leu Glu Ile Lys Arg Leu Glu His His His His
            260                 265                 270
```

His His

<210> SEQ ID NO 56
<211> LENGTH: 275
<212> TYPE: PRT
<213> ORGANISM: Artificial Sequence
<220> FEATURE:
<223> OTHER INFORMATION: Synthetic construct

<400> SEQUENCE: 56

```
Met Ala Gln Val Lys Leu Gln Glu Ser Gly Pro Glu Leu Val Arg Pro
1               5                   10                  15

Gly Thr Ser Val Lys Val Ser Cys Lys Ala Ser Gly Tyr Ala Phe Thr
            20                  25                  30

Asn Tyr Leu Ile His Arg Arg Cys Asn Lys Asn Asn Lys Lys Arg Gly
        35                  40                  45

Gly Gly Gly Ser Glu Trp Ile Lys Gln Arg Pro Gly Gln Gly Leu Glu
    50                  55                  60

Trp Ile Gly Val Ile His Pro Gly Asn Gly Gly Thr Asn Tyr Asn Glu
65                  70                  75                  80

Asn Phe Lys Gly Lys Ala Thr Leu Thr Ala Asp Lys Ser Ser Ser Thr
                85                  90                  95

Ala Tyr Met Gln Leu Ser Ser Leu Thr Ser Asp Asp Ser Ala Val Tyr
            100                 105                 110

Phe Cys Ala Ser Gly Asn Asp Gly Ser Tyr Trp Gly Gln Gly Thr Thr
        115                 120                 125

Val Thr Val Ser Ser Gly Gly Gly Gly Ser Gly Lys Gly Gly Ser Gly
    130                 135                 140

Gly Gly Gly Ser Gly Gly Gly Gly Ser Asp Ile Glu Leu Thr Gln Ser
145                 150                 155                 160

Pro Ser Ser Leu Thr Val Thr Ala Gly Glu Lys Val Thr Met Ser Cys
                165                 170                 175

Lys Ser Ser Gln Ser Leu Leu Asn Ser Gly Asp Gln Lys Ile Tyr Leu
            180                 185                 190

Thr Trp Tyr Gln Gln Lys Pro Gly Gln Pro Pro Lys Leu Leu Ile Tyr
        195                 200                 205

Trp Ala Ser Thr Arg Glu Ser Gly Val Pro Asp Arg Phe Thr Gly Ser
    210                 215                 220

Val Ser Gly Thr Asp Phe Thr Leu Thr Ile Ser Ser Val Gln Ala Glu
225                 230                 235                 240

Asp Leu Ala Val Tyr Tyr Cys Gln Asn Asp Tyr Asn Tyr Pro Tyr Thr
                245                 250                 255

Phe Gly Gly Gly Thr Lys Leu Glu Ile Lys Arg Leu Glu His His His
            260                 265                 270

His His His
        275
```

<210> SEQ ID NO 57
<211> LENGTH: 275
<212> TYPE: PRT
<213> ORGANISM: Artificial Sequence
<220> FEATURE:
<223> OTHER INFORMATION: Synthetic construct

<400> SEQUENCE: 57

```
Met Ala Gln Val Lys Leu Gln Glu Ser Gly Pro Glu Leu Val Arg Pro
1               5                   10                  15
```

-continued

```
Gly Thr Ser Val Lys Val Ser Cys Lys Ala Ser Gly Tyr Ala Phe Thr
            20                  25                  30

Asn Tyr Leu Ile His Arg Arg Cys Asn Pro Asn Asn Lys Lys Arg Gly
        35                  40                  45

Gly Gly Gly Ser Glu Trp Ile Lys Gln Arg Pro Gly Gln Gly Leu Glu
    50                  55                  60

Trp Ile Gly Val Ile His Pro Gly Asn Gly Gly Thr Asn Tyr Asn Glu
65                  70                  75                  80

Asn Phe Lys Gly Lys Ala Thr Leu Thr Ala Asp Lys Ser Ser Ser Thr
                85                  90                  95

Ala Tyr Met Gln Leu Ser Ser Leu Thr Ser Asp Asp Ser Ala Val Tyr
            100                 105                 110

Phe Cys Ala Ser Gly Asn Asp Gly Ser Tyr Trp Gly Gln Gly Thr Thr
        115                 120                 125

Val Thr Val Ser Ser Gly Gly Gly Gly Ser Gly Lys Gly Gly Ser Gly
    130                 135                 140

Gly Gly Gly Ser Gly Gly Gly Gly Ser Asp Ile Glu Leu Thr Gln Ser
145                 150                 155                 160

Pro Ser Ser Leu Thr Val Thr Ala Gly Glu Lys Val Thr Met Ser Cys
                165                 170                 175

Lys Ser Ser Gln Ser Leu Leu Asn Ser Gly Asp Gln Lys Ile Tyr Leu
            180                 185                 190

Thr Trp Tyr Gln Gln Lys Pro Gly Gln Pro Pro Lys Leu Leu Ile Tyr
        195                 200                 205

Trp Ala Ser Thr Arg Glu Ser Gly Val Pro Asp Arg Phe Thr Gly Ser
    210                 215                 220

Val Ser Gly Thr Asp Phe Thr Leu Thr Ile Ser Ser Val Gln Ala Glu
225                 230                 235                 240

Asp Leu Ala Val Tyr Tyr Cys Gln Asn Asp Tyr Asn Tyr Pro Tyr Thr
                245                 250                 255

Phe Gly Gly Gly Thr Lys Leu Glu Ile Lys Arg Leu Glu His His His
            260                 265                 270

His His His
        275
```

<210> SEQ ID NO 58
<211> LENGTH: 278
<212> TYPE: PRT
<213> ORGANISM: Artificial Sequence
<220> FEATURE:
<223> OTHER INFORMATION: Synthetic construct

<400> SEQUENCE: 58

```
Met Ala Gln Val Lys Leu Gln Glu Ser Gly Pro Glu Leu Val Arg Pro
1               5                   10                  15

Gly Thr Ser Val Lys Val Ser Cys Lys Ala Ser Gly Tyr Ala Phe Thr
            20                  25                  30

Asn Tyr Leu Ile Val Ser Arg Arg Arg Arg Arg Arg Gly Gly Arg Arg
        35                  40                  45

Arg Arg Gly Gly Gly Gly Ser Glu Trp Ile Lys Gln Arg Pro Gly Gln
    50                  55                  60

Gly Leu Glu Trp Ile Gly Val Ile His Pro Gly Asn Gly Gly Thr Asn
65                  70                  75                  80

Tyr Asn Glu Asn Phe Lys Gly Lys Ala Thr Leu Thr Ala Asp Lys Ser
                85                  90                  95
```

-continued

Ser Ser Thr Ala Tyr Met Gln Leu Ser Ser Leu Thr Ser Asp Asp Ser
100 105 110

Ala Val Tyr Phe Cys Ala Ser Gly Asn Asp Gly Ser Tyr Trp Gly Gln
115 120 125

Gly Thr Thr Val Thr Val Ser Ser Gly Gly Gly Gly Ser Gly Lys Gly
130 135 140

Gly Ser Gly Gly Gly Gly Ser Gly Gly Gly Gly Ser Asp Ile Glu Leu
145 150 155 160

Thr Gln Ser Pro Ser Ser Leu Thr Val Thr Ala Gly Glu Lys Val Thr
165 170 175

Met Ser Cys Lys Ser Ser Gln Ser Leu Leu Asn Ser Gly Asp Gln Lys
180 185 190

Ile Tyr Leu Thr Trp Tyr Gln Gln Lys Pro Gly Gln Pro Pro Lys Leu
195 200 205

Leu Ile Tyr Trp Ala Ser Thr Arg Glu Ser Gly Val Pro Asp Arg Phe
210 215 220

Thr Gly Ser Val Ser Gly Thr Asp Phe Thr Leu Thr Ile Ser Ser Val
225 230 235 240

Gln Ala Glu Asp Leu Ala Val Tyr Tyr Cys Gln Asn Asp Tyr Asn Tyr
245 250 255

Pro Tyr Thr Phe Gly Gly Gly Thr Lys Leu Glu Ile Lys Arg Leu Glu
260 265 270

His His His His His His
275

<210> SEQ ID NO 59
<211> LENGTH: 280
<212> TYPE: PRT
<213> ORGANISM: Artificial Sequence
<220> FEATURE:
<223> OTHER INFORMATION: Synthetic construct

<400> SEQUENCE: 59

Met Ala Gln Val Lys Leu Gln Glu Ser Gly Pro Glu Leu Val Arg Pro
1 5 10 15

Gly Thr Ser Val Lys Val Ser Cys Lys Ala Ser Gly Tyr Ala Phe Thr
20 25 30

Asn Tyr Leu Ile Gly Lys Cys Ser Thr Arg Gly Arg Lys Cys Cys Arg
35 40 45

Arg Lys Lys Gly Gly Gly Gly Ser Glu Trp Ile Lys Gln Arg Pro Gly
50 55 60

Gln Gly Leu Glu Trp Ile Gly Val Ile His Pro Gly Asn Gly Gly Thr
65 70 75 80

Asn Tyr Asn Glu Asn Phe Lys Gly Lys Ala Thr Leu Thr Ala Asp Lys
85 90 95

Ser Ser Ser Thr Ala Tyr Met Gln Leu Ser Ser Leu Thr Ser Asp Asp
100 105 110

Ser Ala Val Tyr Phe Cys Ala Ser Gly Asn Asp Gly Ser Tyr Trp Gly
115 120 125

Gln Gly Thr Thr Val Thr Val Ser Ser Gly Gly Gly Gly Ser Gly Lys
130 135 140

Gly Gly Ser Gly Gly Gly Gly Ser Gly Gly Gly Gly Ser Asp Ile Glu
145 150 155 160

Leu Thr Gln Ser Pro Ser Ser Leu Thr Val Thr Ala Gly Glu Lys Val
165 170 175

-continued

```
Thr Met Ser Cys Lys Ser Ser Gln Ser Leu Leu Asn Ser Gly Asp Gln
            180                 185                 190

Lys Ile Tyr Leu Thr Trp Tyr Gln Gln Lys Pro Gly Gln Pro Pro Lys
        195                 200                 205

Leu Leu Ile Tyr Trp Ala Ser Thr Arg Glu Ser Gly Val Pro Asp Arg
    210                 215                 220

Phe Thr Gly Ser Val Ser Gly Thr Asp Phe Thr Leu Thr Ile Ser Ser
225                 230                 235                 240

Val Gln Ala Glu Asp Leu Ala Val Tyr Tyr Cys Gln Asn Asp Tyr Asn
                245                 250                 255

Tyr Pro Tyr Thr Phe Gly Gly Gly Thr Lys Leu Glu Ile Lys Arg Leu
            260                 265                 270

Glu His His His His His His His
        275                 280


<210> SEQ ID NO 60
<211> LENGTH: 17
<212> TYPE: PRT
<213> ORGANISM: Artificial Sequence
<220> FEATURE:
<223> OTHER INFORMATION: Synthetic construct

<400> SEQUENCE: 60

Cys Gly Gly Gly Gly Gly His Arg Arg Cys Asn Lys Asn Asn Lys Lys
1               5                   10                  15

Arg


<210> SEQ ID NO 61
<211> LENGTH: 17
<212> TYPE: PRT
<213> ORGANISM: Artificial Sequence
<220> FEATURE:
<223> OTHER INFORMATION: Synthetic construct

<400> SEQUENCE: 61

Cys Gly Gly Gly Gly Gly His Arg Arg Cys Asn Pro Asn Asn Lys Lys
1               5                   10                  15

Arg


<210> SEQ ID NO 62
<211> LENGTH: 20
<212> TYPE: PRT
<213> ORGANISM: Artificial Sequence
<220> FEATURE:
<223> OTHER INFORMATION: Synthetic construct

<400> SEQUENCE: 62

Cys Gly Gly Gly Gly Gly Val Ser Arg Arg Arg Arg Arg Arg Gly Gly
1               5                   10                  15

Arg Arg Arg Arg
            20


<210> SEQ ID NO 63
<211> LENGTH: 21
<212> TYPE: PRT
<213> ORGANISM: Artificial Sequence
<220> FEATURE:
<223> OTHER INFORMATION: Synthetic construct

<400> SEQUENCE: 63

Cys Gly Gly Gly Gly Gly Gly Lys Cys Ser Thr Arg Gly Arg Lys Cys
1               5                   10                  15
```

Cys Arg Arg Lys Lys
20

<210> SEQ ID NO 64
<211> LENGTH: 24
<212> TYPE: PRT
<213> ORGANISM: Artificial Sequence
<220> FEATURE:
<223> OTHER INFORMATION: Synthetic construct

<400> SEQUENCE: 64

Cys Gly Gly Gly Gly Gly Ser Ser Gly Gly Gly Gly Gly Arg Lys Lys
1 5 10 15

Asn Asn Lys Asn Cys Arg Arg His
20

<210> SEQ ID NO 65
<211> LENGTH: 24
<212> TYPE: PRT
<213> ORGANISM: Artificial Sequence
<220> FEATURE:
<223> OTHER INFORMATION: Synthetic construct

<400> SEQUENCE: 65

Cys Gly Gly Gly Gly Gly Ser Ser Gly Gly Gly Gly Gly Arg Lys Lys
1 5 10 15

Asn Asn Pro Asn Cys Arg Arg His
20

<210> SEQ ID NO 66
<211> LENGTH: 27
<212> TYPE: PRT
<213> ORGANISM: Artificial Sequence
<220> FEATURE:
<223> OTHER INFORMATION: Synthetic construct

<400> SEQUENCE: 66

Cys Gly Gly Gly Gly Gly Ser Ser Gly Gly Gly Gly Gly Arg Arg Arg
1 5 10 15

Arg Gly Gly Arg Arg Arg Arg Arg Arg Ser Val
20 25

<210> SEQ ID NO 67
<211> LENGTH: 28
<212> TYPE: PRT
<213> ORGANISM: Artificial Sequence
<220> FEATURE:
<223> OTHER INFORMATION: Synthetic construct

<400> SEQUENCE: 67

Cys Gly Gly Gly Gly Gly Ser Ser Gly Gly Gly Gly Gly Gly Lys Cys
1 5 10 15

Ser Thr Arg Gly Arg Lys Cys Cys Arg Arg Lys Lys
20 25

<210> SEQ ID NO 68
<211> LENGTH: 288
<212> TYPE: PRT
<213> ORGANISM: Artificial Sequence
<220> FEATURE:
<223> OTHER INFORMATION: Synthetic construct

<400> SEQUENCE: 68

Met Ala Trp Val Trp Thr Leu Leu Phe Leu Met Ala Ala Ala Gln Ser

-continued

```
1               5                   10                  15

Ile Gln Ala Glu Trp Ile Lys Gln Arg Pro Gly Gln Gly Leu Glu Trp
            20                  25                  30

Ile Gly Val Ile His Pro Gly Asn Gly Gly Thr Asn Tyr Asn Glu Asn
        35                  40                  45

Phe Lys Gly Lys Ala Thr Leu Thr Ala Asp Lys Ser Ser Ser Thr Ala
    50                  55                  60

Tyr Met Gln Leu Ser Ser Leu Thr Ser Asp Asp Ser Ala Val Tyr Phe
65                  70                  75                  80

Cys Ala Ser Gly Asn Asp Gly Ser Tyr Trp Gly Gln Gly Thr Thr Val
                85                  90                  95

Thr Val Ser Ser Gly Gly Gly Gly Ser Gly Lys Cys Gly Gly Gly Gly
            100                 105                 110

Gly His Arg Arg Cys Asn Lys Asn Asn Lys Lys Arg Gly Gly Ser Gly
        115                 120                 125

Gly Gly Gly Ser Gly Gly Gly Gly Ser Asp Ile Glu Leu Thr Gln Ser
    130                 135                 140

Pro Ser Ser Leu Thr Val Thr Ala Gly Glu Lys Val Thr Met Ser Cys
145                 150                 155                 160

Lys Ser Ser Gln Ser Leu Leu Asn Ser Gly Asp Gln Lys Ile Tyr Leu
                165                 170                 175

Thr Trp Tyr Gln Gln Lys Pro Gly Gln Pro Pro Lys Leu Leu Ile Tyr
            180                 185                 190

Trp Ala Ser Thr Arg Glu Ser Gly Val Pro Asp Arg Phe Thr Gly Ser
        195                 200                 205

Val Ser Gly Thr Asp Phe Thr Leu Thr Ile Ser Ser Val Gln Ala Glu
    210                 215                 220

Asp Leu Ala Val Tyr Tyr Cys Gln Asn Asp Tyr Asn Tyr Pro Tyr Thr
225                 230                 235                 240

Phe Gly Gly Gly Thr Lys Leu Glu Ile Lys Arg Gly Ser Glu Asn Leu
                245                 250                 255

Tyr Phe Gln Gly Gly Ser Gly Lys Pro Ile Pro Asn Pro Leu Leu Gly
            260                 265                 270

Leu Asp Ser Thr Gly Gly Ser Gly Gly Ser His His His His His His
        275                 280                 285


<210> SEQ ID NO 69
<211> LENGTH: 288
<212> TYPE: PRT
<213> ORGANISM: Artificial Sequence
<220> FEATURE:
<223> OTHER INFORMATION: Synthetic construct

<400> SEQUENCE: 69

Met Ala Trp Val Trp Thr Leu Leu Phe Leu Met Ala Ala Ala Gln Ser
1               5                   10                  15

Ile Gln Ala Glu Trp Ile Lys Gln Arg Pro Gly Gln Gly Leu Glu Trp
            20                  25                  30

Ile Gly Val Ile His Pro Gly Asn Gly Gly Thr Asn Tyr Asn Glu Asn
        35                  40                  45

Phe Lys Gly Lys Ala Thr Leu Thr Ala Asp Lys Ser Ser Ser Thr Ala
    50                  55                  60

Tyr Met Gln Leu Ser Ser Leu Thr Ser Asp Asp Ser Ala Val Tyr Phe
65                  70                  75                  80

Cys Ala Ser Gly Asn Asp Gly Ser Tyr Trp Gly Gln Gly Thr Thr Val
```

-continued 85 90 95

Thr Val Ser Ser Gly Gly Gly Gly Ser Gly Lys Cys Gly Gly Gly Gly
100 105 110

Gly His Arg Arg Cys Asn Pro Asn Asn Lys Lys Arg Gly Gly Ser Gly
115 120 125

Gly Gly Gly Ser Gly Gly Gly Gly Ser Asp Ile Glu Leu Thr Gln Ser
130 135 140

Pro Ser Ser Leu Thr Val Thr Ala Gly Glu Lys Val Thr Met Ser Cys
145 150 155 160

Lys Ser Ser Gln Ser Leu Leu Asn Ser Gly Asp Gln Lys Ile Tyr Leu
165 170 175

Thr Trp Tyr Gln Gln Lys Pro Gly Gln Pro Pro Lys Leu Leu Ile Tyr
180 185 190

Trp Ala Ser Thr Arg Glu Ser Gly Val Pro Asp Arg Phe Thr Gly Ser
195 200 205

Val Ser Gly Thr Asp Phe Thr Leu Thr Ile Ser Ser Val Gln Ala Glu
210 215 220

Asp Leu Ala Val Tyr Tyr Cys Gln Asn Asp Tyr Asn Tyr Pro Tyr Thr
225 230 235 240

Phe Gly Gly Gly Thr Lys Leu Glu Ile Lys Arg Gly Ser Glu Asn Leu
245 250 255

Tyr Phe Gln Gly Gly Ser Gly Lys Pro Ile Pro Asn Pro Leu Leu Gly
260 265 270

Leu Asp Ser Thr Gly Gly Ser Gly Gly Ser His His His His His His
275 280 285

<210> SEQ ID NO 70
<211> LENGTH: 291
<212> TYPE: PRT
<213> ORGANISM: Artificial Sequence
<220> FEATURE:
<223> OTHER INFORMATION: Synthetic construct

<400> SEQUENCE: 70

Met Ala Trp Val Trp Thr Leu Leu Phe Leu Met Ala Ala Ala Gln Ser
1 5 10 15

Ile Gln Ala Glu Trp Ile Lys Gln Arg Pro Gly Gln Gly Leu Glu Trp
20 25 30

Ile Gly Val Ile His Pro Gly Asn Gly Gly Thr Asn Tyr Asn Glu Asn
35 40 45

Phe Lys Gly Lys Ala Thr Leu Thr Ala Asp Lys Ser Ser Ser Thr Ala
50 55 60

Tyr Met Gln Leu Ser Ser Leu Thr Ser Asp Asp Ser Ala Val Tyr Phe
65 70 75 80

Cys Ala Ser Gly Asn Asp Gly Ser Tyr Trp Gly Gln Gly Thr Thr Val
85 90 95

Thr Val Ser Ser Gly Gly Gly Gly Ser Gly Lys Cys Gly Gly Gly Gly
100 105 110

Gly Val Ser Arg Arg Arg Arg Arg Arg Gly Gly Arg Arg Arg Arg Gly
115 120 125

Gly Ser Gly Gly Gly Gly Ser Gly Gly Gly Gly Ser Asp Ile Glu Leu
130 135 140

Thr Gln Ser Pro Ser Ser Leu Thr Val Thr Ala Gly Glu Lys Val Thr
145 150 155 160

Met Ser Cys Lys Ser Ser Gln Ser Leu Leu Asn Ser Gly Asp Gln Lys

```
                165                 170                 175

Ile Tyr Leu Thr Trp Tyr Gln Gln Lys Pro Gly Gln Pro Pro Lys Leu
            180                 185                 190

Leu Ile Tyr Trp Ala Ser Thr Arg Glu Ser Gly Val Pro Asp Arg Phe
        195                 200                 205

Thr Gly Ser Val Ser Gly Thr Asp Phe Thr Leu Thr Ile Ser Ser Val
    210                 215                 220

Gln Ala Glu Asp Leu Ala Val Tyr Tyr Cys Gln Asn Asp Tyr Asn Tyr
225                 230                 235                 240

Pro Tyr Thr Phe Gly Gly Gly Thr Lys Leu Glu Ile Lys Arg Gly Ser
                245                 250                 255

Glu Asn Leu Tyr Phe Gln Gly Gly Ser Gly Lys Pro Ile Pro Asn Pro
            260                 265                 270

Leu Leu Gly Leu Asp Ser Thr Gly Gly Ser Gly Gly Ser His His His
        275                 280                 285

His His His
    290


<210> SEQ ID NO 71
<211> LENGTH: 292
<212> TYPE: PRT
<213> ORGANISM: Artificial Sequence
<220> FEATURE:
<223> OTHER INFORMATION: Synthetic construct

<400> SEQUENCE: 71

Met Ala Trp Val Trp Thr Leu Leu Phe Leu Met Ala Ala Ala Gln Ser
1               5                   10                  15

Ile Gln Ala Glu Trp Ile Lys Gln Arg Pro Gly Gln Gly Leu Glu Trp
            20                  25                  30

Ile Gly Val Ile His Pro Gly Asn Gly Gly Thr Asn Tyr Asn Glu Asn
        35                  40                  45

Phe Lys Gly Lys Ala Thr Leu Thr Ala Asp Lys Ser Ser Ser Thr Ala
    50                  55                  60

Tyr Met Gln Leu Ser Ser Leu Thr Ser Asp Asp Ser Ala Val Tyr Phe
65                  70                  75                  80

Cys Ala Ser Gly Asn Asp Gly Ser Tyr Trp Gly Gln Gly Thr Thr Val
                85                  90                  95

Thr Val Ser Ser Gly Gly Gly Gly Ser Gly Lys Cys Gly Gly Gly Gly
            100                 105                 110

Gly Gly Lys Cys Ser Thr Arg Gly Arg Lys Cys Cys Arg Arg Lys Lys
        115                 120                 125

Gly Gly Ser Gly Gly Gly Gly Ser Gly Gly Gly Gly Ser Asp Ile Glu
    130                 135                 140

Leu Thr Gln Ser Pro Ser Ser Leu Thr Val Thr Ala Gly Glu Lys Val
145                 150                 155                 160

Thr Met Ser Cys Lys Ser Ser Gln Ser Leu Leu Asn Ser Gly Asp Gln
                165                 170                 175

Lys Ile Tyr Leu Thr Trp Tyr Gln Gln Lys Pro Gly Gln Pro Pro Lys
            180                 185                 190

Leu Leu Ile Tyr Trp Ala Ser Thr Arg Glu Ser Gly Val Pro Asp Arg
        195                 200                 205

Phe Thr Gly Ser Val Ser Gly Thr Asp Phe Thr Leu Thr Ile Ser Ser
    210                 215                 220

Val Gln Ala Glu Asp Leu Ala Val Tyr Tyr Cys Gln Asn Asp Tyr Asn
```

```
225                 230                 235                 240

Tyr Pro Tyr Thr Phe Gly Gly Gly Thr Lys Leu Glu Ile Lys Arg Gly
                245                 250                 255

Ser Glu Asn Leu Tyr Phe Gln Gly Gly Ser Gly Lys Pro Ile Pro Asn
            260                 265                 270

Pro Leu Leu Gly Leu Asp Ser Thr Gly Gly Ser Gly Gly Ser His His
        275                 280                 285

His His His His
    290


<210> SEQ ID NO 72
<211> LENGTH: 294
<212> TYPE: PRT
<213> ORGANISM: Artificial Sequence
<220> FEATURE:
<223> OTHER INFORMATION: Synthetic construct

<400> SEQUENCE: 72

Met Ala Trp Val Trp Thr Leu Leu Phe Leu Met Ala Ala Ala Gln Ser
1               5                   10                  15

Ile Gln Ala Glu Trp Ile Lys Gln Arg Pro Gly Gln Gly Leu Glu Trp
            20                  25                  30

Ile Gly Val Ile His Pro Gly Asn Gly Gly Thr Asn Tyr Asn Glu Asn
        35                  40                  45

Phe Lys Gly Lys Ala Thr Leu Thr Ala Asp Lys Ser Ser Ser Thr Ala
    50                  55                  60

Tyr Met Gln Leu Ser Ser Leu Thr Ser Asp Asp Ser Ala Val Tyr Phe
65                  70                  75                  80

Cys Ala Ser Gly Asn Asp Gly Ser Tyr Trp Gly Gln Gly Thr Thr Val
                85                  90                  95

Thr Val Ser Ser Gly Gly Gly Gly Ser Gly Lys Cys Gly Gly Gly Gly
            100                 105                 110

Gly Ser Ser Gly Gly Gly Gly His Arg Arg Cys Asn Lys Asn Asn Lys
        115                 120                 125

Lys Arg Gly Gly Ser Gly Gly Gly Gly Ser Gly Gly Gly Gly Ser Asp
    130                 135                 140

Ile Glu Leu Thr Gln Ser Pro Ser Ser Leu Thr Val Thr Ala Gly Glu
145                 150                 155                 160

Lys Val Thr Met Ser Cys Lys Ser Ser Gln Ser Leu Leu Asn Ser Gly
                165                 170                 175

Asp Gln Lys Ile Tyr Leu Thr Trp Tyr Gln Gln Lys Pro Gly Gln Pro
            180                 185                 190

Pro Lys Leu Leu Ile Tyr Trp Ala Ser Thr Arg Glu Ser Gly Val Pro
        195                 200                 205

Asp Arg Phe Thr Gly Ser Val Ser Gly Thr Asp Phe Thr Leu Thr Ile
    210                 215                 220

Ser Ser Val Gln Ala Glu Asp Leu Ala Val Tyr Tyr Cys Gln Asn Asp
225                 230                 235                 240

Tyr Asn Tyr Pro Tyr Thr Phe Gly Gly Gly Thr Lys Leu Glu Ile Lys
                245                 250                 255

Arg Gly Ser Glu Asn Leu Tyr Phe Gln Gly Gly Ser Gly Lys Pro Ile
            260                 265                 270

Pro Asn Pro Leu Leu Gly Leu Asp Ser Thr Gly Gly Ser Gly Gly Ser
        275                 280                 285

His His His His His His
```

290

<210> SEQ ID NO 73
<211> LENGTH: 295
<212> TYPE: PRT
<213> ORGANISM: Artificial Sequence
<220> FEATURE:
<223> OTHER INFORMATION: Synthetic construct

<400> SEQUENCE: 73

Met Ala Trp Val Trp Thr Leu Leu Phe Leu Met Ala Ala Ala Gln Ser
1               5                   10                  15

Ile Gln Ala Glu Trp Ile Lys Gln Arg Pro Gly Gln Gly Leu Glu Trp
            20                  25                  30

Ile Gly Val Ile His Pro Gly Asn Gly Gly Thr Asn Tyr Asn Glu Asn
        35                  40                  45

Phe Lys Gly Lys Ala Thr Leu Thr Ala Asp Lys Ser Ser Ser Thr Ala
    50                  55                  60

Tyr Met Gln Leu Ser Ser Leu Thr Ser Asp Asp Ser Ala Val Tyr Phe
65                  70                  75                  80

Cys Ala Ser Gly Asn Asp Gly Ser Tyr Trp Gly Gln Gly Thr Thr Val
                85                  90                  95

Thr Val Ser Ser Gly Gly Gly Gly Ser Gly Lys Cys Gly Gly Gly Gly
            100                 105                 110

Gly Ser Ser Gly Gly Gly Gly Gly Arg Lys Lys Asn Asn Pro Asn Cys
        115                 120                 125

Arg Arg His Gly Gly Ser Gly Gly Gly Gly Ser Gly Gly Gly Gly Ser
    130                 135                 140

Asp Ile Glu Leu Thr Gln Ser Pro Ser Ser Leu Thr Val Thr Ala Gly
145                 150                 155                 160

Glu Lys Val Thr Met Ser Cys Lys Ser Ser Gln Ser Leu Leu Asn Ser
                165                 170                 175

Gly Asp Gln Lys Ile Tyr Leu Thr Trp Tyr Gln Gln Lys Pro Gly Gln
            180                 185                 190

Pro Pro Lys Leu Leu Ile Tyr Trp Ala Ser Thr Arg Glu Ser Gly Val
        195                 200                 205

Pro Asp Arg Phe Thr Gly Ser Val Ser Gly Thr Asp Phe Thr Leu Thr
    210                 215                 220

Ile Ser Ser Val Gln Ala Glu Asp Leu Ala Val Tyr Tyr Cys Gln Asn
225                 230                 235                 240

Asp Tyr Asn Tyr Pro Tyr Thr Phe Gly Gly Gly Thr Lys Leu Glu Ile
                245                 250                 255

Lys Arg Gly Ser Glu Asn Leu Tyr Phe Gln Gly Gly Ser Gly Lys Pro
            260                 265                 270

Ile Pro Asn Pro Leu Leu Gly Leu Asp Ser Thr Gly Gly Ser Gly Gly
        275                 280                 285

Ser His His His His His His
    290                 295

<210> SEQ ID NO 74
<211> LENGTH: 298
<212> TYPE: PRT
<213> ORGANISM: Artificial Sequence
<220> FEATURE:
<223> OTHER INFORMATION: Synthetic construct

<400> SEQUENCE: 74

-continued

```
Met Ala Trp Val Trp Thr Leu Leu Phe Leu Met Ala Ala Ala Gln Ser
1               5                   10                  15

Ile Gln Ala Glu Trp Ile Lys Gln Arg Pro Gly Gln Gly Leu Glu Trp
            20                  25                  30

Ile Gly Val Ile His Pro Gly Asn Gly Gly Thr Asn Tyr Asn Glu Asn
        35                  40                  45

Phe Lys Gly Lys Ala Thr Leu Thr Ala Asp Lys Ser Ser Ser Thr Ala
    50                  55                  60

Tyr Met Gln Leu Ser Ser Leu Thr Ser Asp Asp Ser Ala Val Tyr Phe
65                  70                  75                  80

Cys Ala Ser Gly Asn Asp Gly Ser Tyr Trp Gly Gln Gly Thr Thr Val
                85                  90                  95

Thr Val Ser Ser Gly Gly Gly Gly Ser Gly Lys Cys Gly Gly Gly Gly
            100                 105                 110

Gly Ser Ser Gly Gly Gly Gly Gly Arg Arg Arg Arg Gly Gly Arg Arg
        115                 120                 125

Arg Arg Arg Arg Ser Val Gly Gly Ser Gly Gly Gly Gly Ser Gly Gly
    130                 135                 140

Gly Gly Ser Asp Ile Glu Leu Thr Gln Ser Pro Ser Ser Leu Thr Val
145                 150                 155                 160

Thr Ala Gly Glu Lys Val Thr Met Ser Cys Lys Ser Ser Gln Ser Leu
                165                 170                 175

Leu Asn Ser Gly Asp Gln Lys Ile Tyr Leu Thr Trp Tyr Gln Gln Lys
            180                 185                 190

Pro Gly Gln Pro Pro Lys Leu Leu Ile Tyr Trp Ala Ser Thr Arg Glu
        195                 200                 205

Ser Gly Val Pro Asp Arg Phe Thr Gly Ser Val Ser Gly Thr Asp Phe
    210                 215                 220

Thr Leu Thr Ile Ser Ser Val Gln Ala Glu Asp Leu Ala Val Tyr Tyr
225                 230                 235                 240

Cys Gln Asn Asp Tyr Asn Tyr Pro Tyr Thr Phe Gly Gly Gly Thr Lys
                245                 250                 255

Leu Glu Ile Lys Arg Gly Ser Glu Asn Leu Tyr Phe Gln Gly Gly Ser
            260                 265                 270

Gly Lys Pro Ile Pro Asn Pro Leu Leu Gly Leu Asp Ser Thr Gly Gly
        275                 280                 285

Ser Gly Gly Ser His His His His His His
    290                 295


<210> SEQ ID NO 75
<211> LENGTH: 299
<212> TYPE: PRT
<213> ORGANISM: Artificial Sequence
<220> FEATURE:
<223> OTHER INFORMATION: Synthetic construct

<400> SEQUENCE: 75

Met Ala Trp Val Trp Thr Leu Leu Phe Leu Met Ala Ala Ala Gln Ser
1               5                   10                  15

Ile Gln Ala Glu Trp Ile Lys Gln Arg Pro Gly Gln Gly Leu Glu Trp
            20                  25                  30

Ile Gly Val Ile His Pro Gly Asn Gly Gly Thr Asn Tyr Asn Glu Asn
        35                  40                  45

Phe Lys Gly Lys Ala Thr Leu Thr Ala Asp Lys Ser Ser Ser Thr Ala
    50                  55                  60
```

```
Tyr Met Gln Leu Ser Ser Leu Thr Ser Asp Asp Ser Ala Val Tyr Phe
65                  70                  75                  80

Cys Ala Ser Gly Asn Asp Gly Ser Tyr Trp Gly Gln Gly Thr Thr Val
                85                  90                  95

Thr Val Ser Ser Gly Gly Gly Gly Ser Gly Lys Cys Gly Gly Gly Gly
            100                 105                 110

Gly Ser Ser Gly Gly Gly Gly Gly Gly Lys Cys Ser Thr Arg Gly Arg
        115                 120                 125

Lys Cys Cys Arg Arg Lys Lys Gly Gly Ser Gly Gly Gly Gly Ser Gly
    130                 135                 140

Gly Gly Gly Ser Asp Ile Glu Leu Thr Gln Ser Pro Ser Ser Leu Thr
145                 150                 155                 160

Val Thr Ala Gly Glu Lys Val Thr Met Ser Cys Lys Ser Ser Gln Ser
                165                 170                 175

Leu Leu Asn Ser Gly Asp Gln Lys Ile Tyr Leu Thr Trp Tyr Gln Gln
            180                 185                 190

Lys Pro Gly Gln Pro Pro Lys Leu Leu Ile Tyr Trp Ala Ser Thr Arg
        195                 200                 205

Glu Ser Gly Val Pro Asp Arg Phe Thr Gly Ser Val Ser Gly Thr Asp
    210                 215                 220

Phe Thr Leu Thr Ile Ser Ser Val Gln Ala Glu Asp Leu Ala Val Tyr
225                 230                 235                 240

Tyr Cys Gln Asn Asp Tyr Asn Tyr Pro Tyr Thr Phe Gly Gly Gly Thr
                245                 250                 255

Lys Leu Glu Ile Lys Arg Gly Ser Glu Asn Leu Tyr Phe Gln Gly Gly
            260                 265                 270

Ser Gly Lys Pro Ile Pro Asn Pro Leu Leu Gly Leu Asp Ser Thr Gly
        275                 280                 285

Gly Ser Gly Gly Ser His His His His His His
    290                 295
```

<210> SEQ ID NO 76
<211> LENGTH: 289
<212> TYPE: PRT
<213> ORGANISM: Artificial Sequence
<220> FEATURE:
<223> OTHER INFORMATION: Synthetic construct

<400> SEQUENCE: 76

```
Met Ala Trp Val Trp Thr Leu Leu Phe Leu Met Ala Ala Ala Gln Ser
1               5                   10                  15

Ile Gln Ala Glu Trp Ile Lys Gln Arg Pro Gly Gln Gly Leu Glu Trp
            20                  25                  30

Ile Gly Val Ile His Pro Gly Asn Gly Gly Thr Asn Tyr Asn Glu Asn
        35                  40                  45

Phe Lys Gly Lys Ala Thr Leu Thr Ala Asp Lys Ser Ser Ser Thr Ala
    50                  55                  60

Tyr Met Gln Leu Ser Ser Leu Thr Ser Asp Asp Ser Ala Val Tyr Phe
65                  70                  75                  80

Cys Ala Ser Gly Asn Asp Gly Ser Tyr Trp Gly Gln Gly Thr Thr Val
                85                  90                  95

Thr Val Ser Ser Gly Gly Gly Gly Ser Gly Lys Gly Gly Ser Gly Gly
            100                 105                 110

Gly Gly Ser Gly Gly Gly Gly Ser Asp Ile Glu Leu Thr Gln Ser Pro
        115                 120                 125
```

-continued

Ser Ser Leu Thr Val Thr Ala Gly Glu Lys Val Thr Met Ser Cys Lys
    130                 135                 140

Ser Ser Gln Ser Leu Leu Asn Ser Gly Asp Gln Lys Ile Tyr Leu Thr
145                 150                 155                 160

Trp Tyr Gln Gln Lys Pro Gly Gln Pro Pro Lys Leu Leu Ile Tyr Trp
                165                 170                 175

Ala Ser Thr Arg Glu Ser Gly Val Pro Asp Arg Phe Thr Gly Ser Val
            180                 185                 190

Ser Gly Thr Asp Phe Thr Leu Thr Ile Ser Ser Val Gln Ala Glu Asp
        195                 200                 205

Leu Ala Val Tyr Tyr Cys Gln Asn Asp Tyr Asn Tyr Pro Tyr Thr Phe
    210                 215                 220

Gly Gly Gly Thr Lys Cys Cys Gly Gly Gly Gly Gly His Arg Arg Cys
225                 230                 235                 240

Asn Lys Asn Asn Lys Lys Arg Leu Glu Ile Lys Arg Gly Ser Glu Asn
                245                 250                 255

Leu Tyr Phe Gln Gly Gly Ser Gly Lys Pro Ile Pro Asn Pro Leu Leu
            260                 265                 270

Gly Leu Asp Ser Thr Gly Gly Ser Gly Gly Ser His His His His His
        275                 280                 285

His

<210> SEQ ID NO 77
<211> LENGTH: 289
<212> TYPE: PRT
<213> ORGANISM: Artificial Sequence
<220> FEATURE:
<223> OTHER INFORMATION: Synthetic construct

<400> SEQUENCE: 77

Met Ala Trp Val Trp Thr Leu Leu Phe Leu Met Ala Ala Ala Gln Ser
1               5                   10                  15

Ile Gln Ala Glu Trp Ile Lys Gln Arg Pro Gly Gln Gly Leu Glu Trp
            20                  25                  30

Ile Gly Val Ile His Pro Gly Asn Gly Gly Thr Asn Tyr Asn Glu Asn
        35                  40                  45

Phe Lys Gly Lys Ala Thr Leu Thr Ala Asp Lys Ser Ser Ser Thr Ala
    50                  55                  60

Tyr Met Gln Leu Ser Ser Leu Thr Ser Asp Asp Ser Ala Val Tyr Phe
65                  70                  75                  80

Cys Ala Ser Gly Asn Asp Gly Ser Tyr Trp Gly Gln Gly Thr Thr Val
                85                  90                  95

Thr Val Ser Ser Gly Gly Gly Gly Ser Gly Lys Gly Gly Ser Gly Gly
            100                 105                 110

Gly Gly Ser Gly Gly Gly Gly Ser Asp Ile Glu Leu Thr Gln Ser Pro
        115                 120                 125

Ser Ser Leu Thr Val Thr Ala Gly Glu Lys Val Thr Met Ser Cys Lys
    130                 135                 140

Ser Ser Gln Ser Leu Leu Asn Ser Gly Asp Gln Lys Ile Tyr Leu Thr
145                 150                 155                 160

Trp Tyr Gln Gln Lys Pro Gly Gln Pro Pro Lys Leu Leu Ile Tyr Trp
                165                 170                 175

Ala Ser Thr Arg Glu Ser Gly Val Pro Asp Arg Phe Thr Gly Ser Val
            180                 185                 190

Ser Gly Thr Asp Phe Thr Leu Thr Ile Ser Ser Val Gln Ala Glu Asp

```
        195                 200                 205

Leu Ala Val Tyr Tyr Cys Gln Asn Asp Tyr Asn Tyr Pro Tyr Thr Phe
    210                 215                 220

Gly Gly Gly Thr Lys Cys Cys Gly Gly Gly Gly Gly His Arg Arg Cys
225                 230                 235                 240

Asn Pro Asn Asn Lys Lys Arg Leu Glu Ile Lys Arg Gly Ser Glu Asn
                245                 250                 255

Leu Tyr Phe Gln Gly Gly Ser Gly Lys Pro Ile Pro Asn Pro Leu Leu
            260                 265                 270

Gly Leu Asp Ser Thr Gly Gly Ser Gly Gly Ser His His His His His
        275                 280                 285

His


<210> SEQ ID NO 78
<211> LENGTH: 292
<212> TYPE: PRT
<213> ORGANISM: Artificial Sequence
<220> FEATURE:
<223> OTHER INFORMATION: Synthetic construct

<400> SEQUENCE: 78

Met Ala Trp Val Trp Thr Leu Leu Phe Leu Met Ala Ala Ala Gln Ser
1               5                   10                  15

Ile Gln Ala Glu Trp Ile Lys Gln Arg Pro Gly Gln Gly Leu Glu Trp
            20                  25                  30

Ile Gly Val Ile His Pro Gly Asn Gly Gly Thr Asn Tyr Asn Glu Asn
        35                  40                  45

Phe Lys Gly Lys Ala Thr Leu Thr Ala Asp Lys Ser Ser Ser Thr Ala
    50                  55                  60

Tyr Met Gln Leu Ser Ser Leu Thr Ser Asp Asp Ser Ala Val Tyr Phe
65                  70                  75                  80

Cys Ala Ser Gly Asn Asp Gly Ser Tyr Trp Gly Gln Gly Thr Thr Val
                85                  90                  95

Thr Val Ser Ser Gly Gly Gly Gly Ser Gly Lys Gly Gly Ser Gly Gly
            100                 105                 110

Gly Gly Ser Gly Gly Gly Gly Ser Asp Ile Glu Leu Thr Gln Ser Pro
        115                 120                 125

Ser Ser Leu Thr Val Thr Ala Gly Glu Lys Val Thr Met Ser Cys Lys
    130                 135                 140

Ser Ser Gln Ser Leu Leu Asn Ser Gly Asp Gln Lys Ile Tyr Leu Thr
145                 150                 155                 160

Trp Tyr Gln Gln Lys Pro Gly Gln Pro Pro Lys Leu Leu Ile Tyr Trp
                165                 170                 175

Ala Ser Thr Arg Glu Ser Gly Val Pro Asp Arg Phe Thr Gly Ser Val
            180                 185                 190

Ser Gly Thr Asp Phe Thr Leu Thr Ile Ser Ser Val Gln Ala Glu Asp
        195                 200                 205

Leu Ala Val Tyr Tyr Cys Gln Asn Asp Tyr Asn Tyr Pro Tyr Thr Phe
    210                 215                 220

Gly Gly Gly Thr Lys Cys Cys Gly Gly Gly Gly Gly Val Ser Arg Arg
225                 230                 235                 240

Arg Arg Arg Arg Gly Gly Arg Arg Arg Arg Leu Glu Ile Lys Arg Gly
                245                 250                 255

Ser Glu Asn Leu Tyr Phe Gln Gly Gly Ser Gly Lys Pro Ile Pro Asn
            260                 265                 270
```

```
Pro Leu Leu Gly Leu Asp Ser Thr Gly Gly Ser Gly Gly Ser His His
        275                 280                 285

His His His His
    290


<210> SEQ ID NO 79
<211> LENGTH: 293
<212> TYPE: PRT
<213> ORGANISM: Artificial Sequence
<220> FEATURE:
<223> OTHER INFORMATION: Synthetic construct

<400> SEQUENCE: 79

Met Ala Trp Val Trp Thr Leu Leu Phe Leu Met Ala Ala Ala Gln Ser
1               5                   10                  15

Ile Gln Ala Glu Trp Ile Lys Gln Arg Pro Gly Gln Gly Leu Glu Trp
            20                  25                  30

Ile Gly Val Ile His Pro Gly Asn Gly Gly Thr Asn Tyr Asn Glu Asn
        35                  40                  45

Phe Lys Gly Lys Ala Thr Leu Thr Ala Asp Lys Ser Ser Ser Thr Ala
    50                  55                  60

Tyr Met Gln Leu Ser Ser Leu Thr Ser Asp Asp Ser Ala Val Tyr Phe
65                  70                  75                  80

Cys Ala Ser Gly Asn Asp Gly Ser Tyr Trp Gly Gln Gly Thr Thr Val
                85                  90                  95

Thr Val Ser Ser Gly Gly Gly Gly Ser Gly Lys Gly Gly Ser Gly Gly
            100                 105                 110

Gly Gly Ser Gly Gly Gly Gly Ser Asp Ile Glu Leu Thr Gln Ser Pro
        115                 120                 125

Ser Ser Leu Thr Val Thr Ala Gly Glu Lys Val Thr Met Ser Cys Lys
    130                 135                 140

Ser Ser Gln Ser Leu Leu Asn Ser Gly Asp Gln Lys Ile Tyr Leu Thr
145                 150                 155                 160

Trp Tyr Gln Gln Lys Pro Gly Gln Pro Pro Lys Leu Leu Ile Tyr Trp
                165                 170                 175

Ala Ser Thr Arg Glu Ser Gly Val Pro Asp Arg Phe Thr Gly Ser Val
            180                 185                 190

Ser Gly Thr Asp Phe Thr Leu Thr Ile Ser Ser Val Gln Ala Glu Asp
        195                 200                 205

Leu Ala Val Tyr Tyr Cys Gln Asn Asp Tyr Asn Tyr Pro Tyr Thr Phe
    210                 215                 220

Gly Gly Gly Thr Lys Cys Cys Gly Gly Gly Gly Gly Gly Lys Cys Ser
225                 230                 235                 240

Thr Arg Gly Arg Lys Cys Cys Arg Arg Lys Lys Leu Glu Ile Lys Arg
                245                 250                 255

Gly Ser Glu Asn Leu Tyr Phe Gln Gly Gly Ser Gly Lys Pro Ile Pro
            260                 265                 270

Asn Pro Leu Leu Gly Leu Asp Ser Thr Gly Gly Ser Gly Gly Ser His
        275                 280                 285

His His His His His
    290


<210> SEQ ID NO 80
<211> LENGTH: 295
<212> TYPE: PRT
<213> ORGANISM: Artificial Sequence
```

<220> FEATURE:
<223> OTHER INFORMATION: Synthetic construct

<400> SEQUENCE: 80

Met Ala Trp Val Trp Thr Leu Leu Phe Leu Met Ala Ala Ala Gln Ser
1 5 10 15

Ile Gln Ala Glu Trp Ile Lys Gln Arg Pro Gly Gln Gly Leu Glu Trp
20 25 30

Ile Gly Val Ile His Pro Gly Asn Gly Gly Thr Asn Tyr Asn Glu Asn
35 40 45

Phe Lys Gly Lys Ala Thr Leu Thr Ala Asp Lys Ser Ser Ser Thr Ala
50 55 60

Tyr Met Gln Leu Ser Ser Leu Thr Ser Asp Asp Ser Ala Val Tyr Phe
65 70 75 80

Cys Ala Ser Gly Asn Asp Gly Ser Tyr Trp Gly Gln Gly Thr Thr Val
85 90 95

Thr Val Ser Ser Gly Gly Gly Gly Ser Gly Lys Gly Gly Ser Gly Gly
100 105 110

Gly Gly Ser Gly Gly Gly Gly Ser Asp Ile Glu Leu Thr Gln Ser Pro
115 120 125

Ser Ser Leu Thr Val Thr Ala Gly Glu Lys Val Thr Met Ser Cys Lys
130 135 140

Ser Ser Gln Ser Leu Leu Asn Ser Gly Asp Gln Lys Ile Tyr Leu Thr
145 150 155 160

Trp Tyr Gln Gln Lys Pro Gly Gln Pro Pro Lys Leu Leu Ile Tyr Trp
165 170 175

Ala Ser Thr Arg Glu Ser Gly Val Pro Asp Arg Phe Thr Gly Ser Val
180 185 190

Ser Gly Thr Asp Phe Thr Leu Thr Ile Ser Ser Val Gln Ala Glu Asp
195 200 205

Leu Ala Val Tyr Tyr Cys Gln Asn Asp Tyr Asn Tyr Pro Tyr Thr Phe
210 215 220

Gly Gly Gly Thr Lys Cys Cys Gly Gly Gly Gly Gly Ser Ser Gly Gly
225 230 235 240

Gly Gly His Arg Arg Cys Asn Lys Asn Asn Lys Lys Arg Leu Glu Ile
245 250 255

Lys Arg Gly Ser Glu Asn Leu Tyr Phe Gln Gly Gly Ser Gly Lys Pro
260 265 270

Ile Pro Asn Pro Leu Leu Gly Leu Asp Ser Thr Gly Gly Ser Gly Gly
275 280 285

Ser His His His His His His
290 295

<210> SEQ ID NO 81
<211> LENGTH: 296
<212> TYPE: PRT
<213> ORGANISM: Artificial Sequence
<220> FEATURE:
<223> OTHER INFORMATION: Synthetic construct

<400> SEQUENCE: 81

Met Ala Trp Val Trp Thr Leu Leu Phe Leu Met Ala Ala Ala Gln Ser
1 5 10 15

Ile Gln Ala Glu Trp Ile Lys Gln Arg Pro Gly Gln Gly Leu Glu Trp
20 25 30

Ile Gly Val Ile His Pro Gly Asn Gly Gly Thr Asn Tyr Asn Glu Asn

```
        35                  40                  45

Phe Lys Gly Lys Ala Thr Leu Thr Ala Asp Lys Ser Ser Ser Thr Ala
    50                  55                  60

Tyr Met Gln Leu Ser Ser Leu Thr Ser Asp Asp Ser Ala Val Tyr Phe
65                  70                  75                  80

Cys Ala Ser Gly Asn Asp Gly Ser Tyr Trp Gly Gln Gly Thr Thr Val
                85                  90                  95

Thr Val Ser Ser Gly Gly Gly Gly Ser Gly Lys Gly Gly Ser Gly Gly
            100                 105                 110

Gly Gly Ser Gly Gly Gly Gly Ser Asp Ile Glu Leu Thr Gln Ser Pro
        115                 120                 125

Ser Ser Leu Thr Val Thr Ala Gly Glu Lys Val Thr Met Ser Cys Lys
    130                 135                 140

Ser Ser Gln Ser Leu Leu Asn Ser Gly Asp Gln Lys Ile Tyr Leu Thr
145                 150                 155                 160

Trp Tyr Gln Gln Lys Pro Gly Gln Pro Pro Lys Leu Leu Ile Tyr Trp
                165                 170                 175

Ala Ser Thr Arg Glu Ser Gly Val Pro Asp Arg Phe Thr Gly Ser Val
            180                 185                 190

Ser Gly Thr Asp Phe Thr Leu Thr Ile Ser Ser Val Gln Ala Glu Asp
        195                 200                 205

Leu Ala Val Tyr Tyr Cys Gln Asn Asp Tyr Asn Tyr Pro Tyr Thr Phe
    210                 215                 220

Gly Gly Gly Thr Lys Cys Cys Gly Gly Gly Gly Gly Ser Ser Gly Gly
225                 230                 235                 240

Gly Gly Gly Arg Lys Lys Asn Asn Pro Asn Cys Arg Arg His Leu Glu
                245                 250                 255

Ile Lys Arg Gly Ser Glu Asn Leu Tyr Phe Gln Gly Gly Ser Gly Lys
            260                 265                 270

Pro Ile Pro Asn Pro Leu Leu Gly Leu Asp Ser Thr Gly Gly Ser Gly
        275                 280                 285

Gly Ser His His His His His His
    290                 295
```

<210> SEQ ID NO 82
<211> LENGTH: 301
<212> TYPE: PRT
<213> ORGANISM: Artificial Sequence
<220> FEATURE:
<223> OTHER INFORMATION: Synthetic construct

<400> SEQUENCE: 82

```
Met Ala Trp Val Trp Thr Leu Leu Phe Leu Met Ala Ala Ala Gln Ser
1               5                   10                  15

Ile Gln Ala Glu Trp Ile Lys Gln Arg Pro Gly Gln Gly Leu Glu Trp
            20                  25                  30

Ile Gly Val Ile His Pro Gly Asn Gly Gly Thr Asn Tyr Asn Glu Asn
        35                  40                  45

Phe Lys Gly Lys Ala Thr Leu Thr Ala Asp Lys Ser Ser Ser Thr Ala
    50                  55                  60

Tyr Met Gln Leu Ser Ser Leu Thr Ser Asp Asp Ser Ala Val Tyr Phe
65                  70                  75                  80

Cys Ala Ser Gly Asn Asp Gly Ser Tyr Trp Gly Gln Gly Thr Thr Val
                85                  90                  95

Thr Val Ser Ser Gly Gly Gly Gly Ser Gly Lys Gly Gly Ser Gly Gly
```

```
            100                 105                 110

Gly Gly Ser Gly Gly Gly Gly Ser Asp Ile Glu Leu Thr Gln Ser Pro
        115                 120                 125

Ser Ser Leu Thr Val Thr Ala Gly Glu Lys Val Thr Met Ser Cys Lys
    130                 135                 140

Ser Ser Gln Ser Leu Leu Asn Ser Gly Asp Gln Lys Ile Tyr Leu Thr
145                 150                 155                 160

Trp Tyr Gln Gln Lys Pro Gly Gln Pro Pro Lys Leu Leu Ile Tyr Trp
                165                 170                 175

Ala Ser Thr Arg Glu Ser Gly Val Pro Asp Arg Phe Thr Gly Ser Val
            180                 185                 190

Ser Gly Thr Asp Phe Thr Leu Thr Ile Ser Ser Val Gln Ala Glu Asp
        195                 200                 205

Leu Ala Val Tyr Tyr Cys Gln Asn Asp Tyr Asn Tyr Pro Tyr Thr Phe
    210                 215                 220

Gly Gly Gly Thr Lys Cys Cys Gly Gly Gly Gly Gly Ser Ser Gly Gly
225                 230                 235                 240

Gly Gly Gly Val Ser Arg Arg Arg Arg Gly Gly Arg Arg Arg Arg Arg
                245                 250                 255

Arg Ser Val Leu Glu Ile Lys Arg Gly Ser Glu Asn Leu Tyr Phe Gln
            260                 265                 270

Gly Gly Ser Gly Lys Pro Ile Pro Asn Pro Leu Leu Gly Leu Asp Ser
        275                 280                 285

Thr Gly Gly Ser Gly Gly Ser His His His His His His
    290                 295                 300


<210> SEQ ID NO 83
<211> LENGTH: 300
<212> TYPE: PRT
<213> ORGANISM: Artificial Sequence
<220> FEATURE:
<223> OTHER INFORMATION: Synthetic construct

<400> SEQUENCE: 83

Met Ala Trp Val Trp Thr Leu Leu Phe Leu Met Ala Ala Ala Gln Ser
1               5                   10                  15

Ile Gln Ala Glu Trp Ile Lys Gln Arg Pro Gly Gln Gly Leu Glu Trp
            20                  25                  30

Ile Gly Val Ile His Pro Gly Asn Gly Gly Thr Asn Tyr Asn Glu Asn
        35                  40                  45

Phe Lys Gly Lys Ala Thr Leu Thr Ala Asp Lys Ser Ser Ser Thr Ala
    50                  55                  60

Tyr Met Gln Leu Ser Ser Leu Thr Ser Asp Asp Ser Ala Val Tyr Phe
65                  70                  75                  80

Cys Ala Ser Gly Asn Asp Gly Ser Tyr Trp Gly Gln Gly Thr Thr Val
                85                  90                  95

Thr Val Ser Ser Gly Gly Gly Gly Ser Gly Lys Gly Gly Ser Gly Gly
            100                 105                 110

Gly Gly Ser Gly Gly Gly Gly Ser Asp Ile Glu Leu Thr Gln Ser Pro
        115                 120                 125

Ser Ser Leu Thr Val Thr Ala Gly Glu Lys Val Thr Met Ser Cys Lys
    130                 135                 140

Ser Ser Gln Ser Leu Leu Asn Ser Gly Asp Gln Lys Ile Tyr Leu Thr
145                 150                 155                 160

Trp Tyr Gln Gln Lys Pro Gly Gln Pro Pro Lys Leu Leu Ile Tyr Trp
```

-continued

```
                165                 170                 175

Ala Ser Thr Arg Glu Ser Gly Val Pro Asp Arg Phe Thr Gly Ser Val
            180                 185                 190

Ser Gly Thr Asp Phe Thr Leu Thr Ile Ser Ser Val Gln Ala Glu Asp
        195                 200                 205

Leu Ala Val Tyr Tyr Cys Gln Asn Asp Tyr Asn Tyr Pro Tyr Thr Phe
    210                 215                 220

Gly Gly Gly Thr Lys Cys Cys Gly Gly Gly Gly Gly Ser Ser Gly Gly
225                 230                 235                 240

Gly Gly Gly Gly Lys Cys Ser Thr Arg Gly Arg Lys Cys Cys Arg Arg
                245                 250                 255

Lys Lys Leu Glu Ile Lys Arg Gly Ser Glu Asn Leu Tyr Phe Gln Gly
            260                 265                 270

Gly Ser Gly Lys Pro Ile Pro Asn Pro Leu Leu Gly Leu Asp Ser Thr
        275                 280                 285

Gly Gly Ser Gly Gly Ser His His His His His His
    290                 295                 300
```

<210> SEQ ID NO 84
<211> LENGTH: 34
<212> TYPE: DNA
<213> ORGANISM: Artificial Sequence
<220> FEATURE:
<223> OTHER INFORMATION: Synthetic construct

<400> SEQUENCE: 84
aaggagatat acatatgatg gcatgggttt ggac 34

<210> SEQ ID NO 85
<211> LENGTH: 46
<212> TYPE: DNA
<213> ORGANISM: Artificial Sequence
<220> FEATURE:
<223> OTHER INFORMATION: Synthetic construct

<400> SEQUENCE: 85
agcccgaagg gaattcattt gcagatacaa agtgttttta gagttg 46

<210> SEQ ID NO 86
<211> LENGTH: 11
<212> TYPE: PRT
<213> ORGANISM: Artificial Sequence
<220> FEATURE:
<223> OTHER INFORMATION: Synthetic construct

<400> SEQUENCE: 86

```
His Arg Arg Cys Asn Lys Asn Asn Lys Lys Arg
1               5                   10
```

<210> SEQ ID NO 87
<211> LENGTH: 11
<212> TYPE: PRT
<213> ORGANISM: Artificial Sequence
<220> FEATURE:
<223> OTHER INFORMATION: Synthetic construct

<400> SEQUENCE: 87

```
His Arg Arg Cys Asn Pro Asn Asn Lys Lys Arg
1               5                   10
```

<210> SEQ ID NO 88
<211> LENGTH: 14

-continued

<212> TYPE: PRT
<213> ORGANISM: Artificial Sequence
<220> FEATURE:
<223> OTHER INFORMATION: Synthetic construct

<400> SEQUENCE: 88

Val Ser Arg Arg Arg Arg Arg Arg Gly Gly Arg Arg Arg Arg
1 5 10

<210> SEQ ID NO 89
<211> LENGTH: 15
<212> TYPE: PRT
<213> ORGANISM: Artificial Sequence
<220> FEATURE:
<223> OTHER INFORMATION: Synthetic construct

<400> SEQUENCE: 89

Gly Lys Cys Ser Thr Arg Gly Arg Lys Cys Cys Arg Arg Lys Lys
1 5 10 15

<210> SEQ ID NO 90
<211> LENGTH: 280
<212> TYPE: PRT
<213> ORGANISM: Artificial Sequence
<220> FEATURE:
<223> OTHER INFORMATION: Synthetic construct

<400> SEQUENCE: 90

Met Ala Gln Val Lys Leu Gln Glu Ser Gly Pro Glu Leu Val Arg Pro
1 5 10 15

Gly Thr Ser Val Lys Val Ser Cys Lys Ala Ser Gly Tyr Ala Phe Thr
20 25 30

Asn Tyr Leu Ile Glu Trp Ile Lys Gln Arg Pro Gly Gln Gly Leu Glu
35 40 45

Trp Ile Gly Val Ile His Pro Gly Asn Gly Gly Thr Asn Tyr Asn Glu
50 55 60

Asn Phe Lys Gly Lys Ala Thr Leu Thr Ala Asp Lys Ser Ser Ser Thr
65 70 75 80

Ala Tyr Met Gln Leu Ser Ser Leu Thr Ser Asp Asp Ser Ala Val Tyr
85 90 95

Phe Cys Ala Ser Gly Asn Asp Gly Ser Tyr Trp Gly Gln Gly Thr Thr
100 105 110

Val Thr Val Ser Ser Gly Gly Gly Gly Ser Gly Gly Gly Gly Ser Gly
115 120 125

Gly Gly Gly Ser Asp Ile Glu Leu Thr Gln Ser Pro Ser Ser Leu Thr
130 135 140

Val Thr Ala Gly Glu Lys Val Thr Met Ser Cys Lys Ser Ser Gln Ser
145 150 155 160

Leu Leu Asn Ser Gly Asp Gln Lys Ile Tyr Leu Thr Trp Tyr Gln Gln
165 170 175

Lys Pro Gly Gln Pro Pro Lys Leu Leu Ile Tyr Trp Ala Ser Thr Arg
180 185 190

Glu Ser Gly Val Pro Asp Arg Phe Thr Gly Ser Val Ser Gly Thr Asp
195 200 205

Phe Thr Leu Thr Ile Ser Ser Val Gln Ala Glu Asp Leu Ala Val Tyr
210 215 220

Tyr Cys Gln Asn Asp Tyr Asn Tyr Pro Tyr Thr Phe Gly Gly Gly Thr
225 230 235 240

Lys Gly Gly Gly Gly Ser Gly Gly Gly Gly Ser Gly Gly Gly Gly Ser

```
                245                 250                 255

His Arg Arg Cys Asn Lys Asn Asn Lys Lys Arg Leu Glu Ile Lys Arg
            260                 265                 270

Leu Glu His His His His His His
        275                 280


<210> SEQ ID NO 91
<211> LENGTH: 280
<212> TYPE: PRT
<213> ORGANISM: Artificial Sequence
<220> FEATURE:
<223> OTHER INFORMATION: Synthetic construct

<400> SEQUENCE: 91

Met Ala Gln Val Lys Leu Gln Glu Ser Gly Pro Glu Leu Val Arg Pro
1               5                   10                  15

Gly Thr Ser Val Lys Val Ser Cys Lys Ala Ser Gly Tyr Ala Phe Thr
            20                  25                  30

Asn Tyr Leu Ile Glu Trp Ile Lys Gln Arg Pro Gly Gln Gly Leu Glu
        35                  40                  45

Trp Ile Gly Val Ile His Pro Gly Asn Gly Gly Thr Asn Tyr Asn Glu
    50                  55                  60

Asn Phe Lys Gly Lys Ala Thr Leu Thr Ala Asp Lys Ser Ser Ser Thr
65                  70                  75                  80

Ala Tyr Met Gln Leu Ser Ser Leu Thr Ser Asp Asp Ser Ala Val Tyr
                85                  90                  95

Phe Cys Ala Ser Gly Asn Asp Gly Ser Tyr Trp Gly Gln Gly Thr Thr
            100                 105                 110

Val Thr Val Ser Ser Gly Gly Gly Gly Ser Gly Gly Gly Gly Ser Gly
        115                 120                 125

Gly Gly Gly Ser Asp Ile Glu Leu Thr Gln Ser Pro Ser Ser Leu Thr
    130                 135                 140

Val Thr Ala Gly Glu Lys Val Thr Met Ser Cys Lys Ser Ser Gln Ser
145                 150                 155                 160

Leu Leu Asn Ser Gly Asp Gln Lys Ile Tyr Leu Thr Trp Tyr Gln Gln
                165                 170                 175

Lys Pro Gly Gln Pro Pro Lys Leu Leu Ile Tyr Trp Ala Ser Thr Arg
            180                 185                 190

Glu Ser Gly Val Pro Asp Arg Phe Thr Gly Ser Val Ser Gly Thr Asp
        195                 200                 205

Phe Thr Leu Thr Ile Ser Ser Val Gln Ala Glu Asp Leu Ala Val Tyr
    210                 215                 220

Tyr Cys Gln Asn Asp Tyr Asn Tyr Pro Tyr Thr Phe Gly Gly Gly Thr
225                 230                 235                 240

Lys Gly Gly Gly Gly Ser Gly Gly Gly Gly Ser Gly Gly Gly Gly Ser
                245                 250                 255

His Arg Arg Cys Asn Pro Asn Asn Lys Lys Arg Leu Glu Ile Lys Arg
            260                 265                 270

Leu Glu His His His His His His
        275                 280


<210> SEQ ID NO 92
<211> LENGTH: 283
<212> TYPE: PRT
<213> ORGANISM: Artificial Sequence
<220> FEATURE:
<223> OTHER INFORMATION: Synthetic construct
```

<400> SEQUENCE: 92

Met Ala Gln Val Lys Leu Gln Glu Ser Gly Pro Glu Leu Val Arg Pro
1 5 10 15

Gly Thr Ser Val Lys Val Ser Cys Lys Ala Ser Gly Tyr Ala Phe Thr
20 25 30

Asn Tyr Leu Ile Glu Trp Ile Lys Gln Arg Pro Gly Gln Gly Leu Glu
35 40 45

Trp Ile Gly Val Ile His Pro Gly Asn Gly Gly Thr Asn Tyr Asn Glu
50 55 60

Asn Phe Lys Gly Lys Ala Thr Leu Thr Ala Asp Lys Ser Ser Ser Thr
65 70 75 80

Ala Tyr Met Gln Leu Ser Ser Leu Thr Ser Asp Asp Ser Ala Val Tyr
85 90 95

Phe Cys Ala Ser Gly Asn Asp Gly Ser Tyr Trp Gly Gln Gly Thr Thr
100 105 110

Val Thr Val Ser Ser Gly Gly Gly Gly Ser Gly Gly Gly Gly Ser Gly
115 120 125

Gly Gly Gly Ser Asp Ile Glu Leu Thr Gln Ser Pro Ser Ser Leu Thr
130 135 140

Val Thr Ala Gly Glu Lys Val Thr Met Ser Cys Lys Ser Ser Gln Ser
145 150 155 160

Leu Leu Asn Ser Gly Asp Gln Lys Ile Tyr Leu Thr Trp Tyr Gln Gln
165 170 175

Lys Pro Gly Gln Pro Pro Lys Leu Leu Ile Tyr Trp Ala Ser Thr Arg
180 185 190

Glu Ser Gly Val Pro Asp Arg Phe Thr Gly Ser Val Ser Gly Thr Asp
195 200 205

Phe Thr Leu Thr Ile Ser Ser Val Gln Ala Glu Asp Leu Ala Val Tyr
210 215 220

Tyr Cys Gln Asn Asp Tyr Asn Tyr Pro Tyr Thr Phe Gly Gly Gly Thr
225 230 235 240

Lys Gly Gly Gly Gly Ser Gly Gly Gly Gly Ser Gly Gly Gly Gly Ser
245 250 255

Val Ser Arg Arg Arg Arg Arg Arg Gly Gly Arg Arg Arg Arg Leu Glu
260 265 270

Ile Lys Arg Leu Glu His His His His His His
275 280

<210> SEQ ID NO 93
<211> LENGTH: 284
<212> TYPE: PRT
<213> ORGANISM: Artificial Sequence
<220> FEATURE:
<223> OTHER INFORMATION: Synthetic construct

<400> SEQUENCE: 93

Met Ala Gln Val Lys Leu Gln Glu Ser Gly Pro Glu Leu Val Arg Pro
1 5 10 15

Gly Thr Ser Val Lys Val Ser Cys Lys Ala Ser Gly Tyr Ala Phe Thr
20 25 30

Asn Tyr Leu Ile Glu Trp Ile Lys Gln Arg Pro Gly Gln Gly Leu Glu
35 40 45

Trp Ile Gly Val Ile His Pro Gly Asn Gly Gly Thr Asn Tyr Asn Glu
50 55 60

-continued

Asn Phe Lys Gly Lys Ala Thr Leu Thr Ala Asp Lys Ser Ser Ser Thr
65 70 75 80

Ala Tyr Met Gln Leu Ser Ser Leu Thr Ser Asp Asp Ser Ala Val Tyr
85 90 95

Phe Cys Ala Ser Gly Asn Asp Gly Ser Tyr Trp Gly Gln Gly Thr Thr
100 105 110

Val Thr Val Ser Ser Gly Gly Gly Gly Ser Gly Gly Gly Gly Ser Gly
115 120 125

Gly Gly Gly Ser Asp Ile Glu Leu Thr Gln Ser Pro Ser Ser Leu Thr
130 135 140

Val Thr Ala Gly Glu Lys Val Thr Met Ser Cys Lys Ser Ser Gln Ser
145 150 155 160

Leu Leu Asn Ser Gly Asp Gln Lys Ile Tyr Leu Thr Trp Tyr Gln Gln
165 170 175

Lys Pro Gly Gln Pro Pro Lys Leu Leu Ile Tyr Trp Ala Ser Thr Arg
180 185 190

Glu Ser Gly Val Pro Asp Arg Phe Thr Gly Ser Val Ser Gly Thr Asp
195 200 205

Phe Thr Leu Thr Ile Ser Ser Val Gln Ala Glu Asp Leu Ala Val Tyr
210 215 220

Tyr Cys Gln Asn Asp Tyr Asn Tyr Pro Tyr Thr Phe Gly Gly Gly Thr
225 230 235 240

Lys Gly Gly Gly Gly Ser Gly Gly Gly Gly Ser Gly Gly Gly Gly Ser
245 250 255

Gly Lys Cys Ser Thr Arg Gly Arg Lys Cys Cys Arg Arg Lys Lys Leu
260 265 270

Glu Ile Lys Arg Leu Glu His His His His His His
275 280

<210> SEQ ID NO 94
<211> LENGTH: 5
<212> TYPE: PRT
<213> ORGANISM: Artificial Sequence
<220> FEATURE:
<223> OTHER INFORMATION: Synthetic construct

<400> SEQUENCE: 94

Gly Gly Gly Gly Ser
1 5

<210> SEQ ID NO 95
<211> LENGTH: 15
<212> TYPE: PRT
<213> ORGANISM: Artificial Sequence
<220> FEATURE:
<223> OTHER INFORMATION: Synthetic construct

<400> SEQUENCE: 95

Gly Gly Gly Gly Ser Gly Gly Gly Gly Ser Gly Gly Gly Gly Ser
1 5 10 15

<210> SEQ ID NO 96
<211> LENGTH: 6
<212> TYPE: PRT
<213> ORGANISM: Artificial Sequence
<220> FEATURE:
<223> OTHER INFORMATION: Synthetic construct

<400> SEQUENCE: 96

Cys Gly Gly Gly Gly Gly

-continued

```
1               5


<210> SEQ ID NO 97
<211> LENGTH: 13
<212> TYPE: PRT
<213> ORGANISM: Artificial Sequence
<220> FEATURE:
<223> OTHER INFORMATION: Synthetic construct

<400> SEQUENCE: 97

Cys Gly Gly Gly Gly Gly Ser Ser Gly Gly Gly Gly Gly
1               5                   10


<210> SEQ ID NO 98
<211> LENGTH: 20
<212> TYPE: PRT
<213> ORGANISM: Artificial Sequence
<220> FEATURE:
<223> OTHER INFORMATION: Synthetic construct

<400> SEQUENCE: 98

Gly Gly Gly Gly Ser Gly Lys Gly Gly Ser Gly Gly Gly Gly Ser Gly
1               5                   10                  15

Gly Gly Gly Ser
            20
```